United States Patent
Sastry-Dent et al.

(10) Patent No.: US 9,765,404 B2
(45) Date of Patent: Sep. 19, 2017

(54) RAPID ASSAY FOR IDENTIFYING TRANSFORMANTS HAVING TARGETED DONOR INSERTION

(71) Applicant: Dow AgroSciences LLC, Indianapolis, IN (US)

(72) Inventors: Lakshmi Sastry-Dent, Avon, IN (US); W. Michael Ainley, Carmel, IN (US); Jayakumar P. Samuel, Carmel, IN (US); Zehui Cao, Westfield, IN (US); Liu Y. Shen, Westfield, IN (US); Cristie M. Dewes, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 370 days.

(21) Appl. No.: 14/475,968

(22) Filed: Sep. 3, 2014

(65) Prior Publication Data
US 2015/0064708 A1   Mar. 5, 2015

Related U.S. Application Data

(60) Provisional application No. 61/873,719, filed on Sep. 4, 2013, provisional application No. 61/899,569, filed on Nov. 4, 2013.

(51) Int. Cl.
*C12P 19/34* (2006.01)
*C12Q 1/68* (2006.01)

(52) U.S. Cl.
CPC ............................... *C12Q 1/6895* (2013.01)

(58) Field of Classification Search
USPC ................................................ 435/6.12, 91.2
See application file for complete search history.

(56) References Cited

U.S. PATENT DOCUMENTS

| | | | |
|---|---|---|---|
| 6,391,544 B1 | 5/2002 | Salituro et al. | |
| 2001/0034028 A1* | 10/2001 | Link | C12N 15/1034 435/6.14 |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0188987 A1 | 8/2006 | Guschin et al. | |
| 2008/0182332 A1 | 7/2008 | Cai et al. | |
| 2009/0205083 A1 | 8/2009 | Gupta et al. | |
| 2011/0008833 A1 | 1/2011 | Petolino et al. | |
| 2011/0027235 A1* | 2/2011 | Gregory | C12N 9/22 424/93.7 |
| 2011/0281306 A1 | 11/2011 | Kim et al. | |

FOREIGN PATENT DOCUMENTS

| WO | WO 2007/014275 | 2/2007 |
| WO | WO 2008/148559 | 12/2008 |
| WO | WO 2010/077319 | 7/2010 |
| WO | WO 2011/091311 | 7/2011 |
| WO | WO 2011/091317 | 7/2011 |

OTHER PUBLICATIONS

PCT International Search Report for PCT/US2014/53832.
PCT International Written Opinion for PCT/US2014/53832 completed by the US Searching Authority on Jan. 7, 2015.

* cited by examiner

*Primary Examiner* — Kenneth Horlick
(74) *Attorney, Agent, or Firm* — Sean M. Russell; James Daly, IV; Barnes & Thornburg LLP

(57) ABSTRACT

The present disclosure provides methods for detecting and identifying plant events that contain donor sequences inserted precisely into targeted genomic loci, and plants and plant cells comprising such targeted genomic loci. The method comprises the steps of amplifying a genomic DNA with a first round of PCR to produce a first amplicon from donor sequences inserted in the reverse orientation, amplifying the first amplicon with a second round of PCR and detecting the presence of the second amplicon, wherein the production of the first and second amplicon indicates the presence of the site specific integration event.

17 Claims, 15 Drawing Sheets

BS: Binding Sites
RS: Restriction Sites

| ID | Name | Treatment | # Indels/1M HQ reads |
|---|---|---|---|
| optimal_loci_204637 | OGL1 | C | 115.1827783 |
| | | ZFN 111879 | 2458.971273 |
| optimal_loci_204726 | OGL2 | C | 10.86457474 |
| | | ZFN 111885 | 102.9851891 |
| optimal_loci_31710 | OGL 11 | C | 1359.364352 |
| | | ZFN 117402 | 8209.320688 |
| optimal_loci_156393 | OGL 12 | C | 368.6331485 |
| | | ZFN 117404 | 7748.53473 |
| optimal_loci_157315 | OGL 13 | C | 79.11178495 |
| | | ZFN 117429 | 453.3253803 |
| optimal_loci_197372 | OGL 14 | C | 48.99318995 |
| | | ZFN 117406 | 277.1403482 |
| optimal_loci_198387 | OGL 15 | C | 45.49262935 |
| | | ZFN 117408 | 622.2166624 |
| optimal_loci_232228 | OGL 16 | C | 163.1649867 |
| | | ZFN 117411 | 5980.912998 |
| optimal_loci_285621 | OGL 17 | C | 0 |
| | | ZFN 117413 | 4.815941547 |

Figure 20:

| | | |
|---|---|---|
| | AAD1 Gene Landing Pad | ZFN cleavage site          EXZACT |

| | |
|---|---|
| predicted | AGAGGCGCGCCGCCTTTTGCAGTTT –ATCCACTAGGGACAGGATTGCCACCCCACAG |
| A9-1 | AGAGGCGCGCCGCCTTTTGCAGTTT –ATCCACTAGGGACAGGATTGCCACCCCACAG |
| A9-2 | AGAGGCGCGCCGCCTTTTGCAGTT---------------AGGGACAGGATTGCCACCCCACAG |
| A9-5 | AGAGGCGCGCCGCCTTTTGCAGTTT –ATCCACTAGGGACAGGATTGCCACCCCACAG |
| A9-6 | AGAGGCGCGCCGCC----------------------------ACTAGGGACAGGATTGCCACCCCACAG |
| G8-1 | AGAGGCGCGCCGCCTTTTGCAGTTT –A ------CTAGGGACAGGATTGCCACCCCACAG |
| G8-2 | AGAGGCGCGCCGCCTTTTGCAGTTT----------CTAGGGACAGGATTGCCACCCCACAG |
| G8-5 | AGAGGCGCGCCGCCTTTTGCAGTTT –ATCCACTAGGGACAGGATTGCCACCCCACAG |
| G8-6 | AGAGGCGCGCCGCCTTTTGCAGTTT----------CTAGGGACAGGATTGCCACCCCACAG |
| G9-1 | AGAGGCGCGCCGCCTTTTGCA--------------------CTAGGGACAGGATTGCCACCCCACAG |
| G9-2 | AGAGGCGCGCCGCCTTTTGCAGTTT-A--------CTAGGGACAGGATTGCCACCCCACAG |
| G9-5 | AGAGGCGCGCCGCCTTTTGCAGTTT-A--------CTAGGGACAGGATTGCCACCCCACAG |
| G9-6 | AGAGGCGCGCCGCCTTTTGCAGTTT-A--------CTAGGGACAGGATTGCCACCCCACAG |
| H9-1 | AGAGGCGCGCCGCCTTTTGCAGTTTAATCCACTAGGGACAGGATTGCCACCCCACAG |
| H9-2 | AGAGGCGCGCCGCCTTTTGCAGTTT-A----------AGGGACAGGATTGCCACCCCACAG |
| H9-5 | AGAGGCGCGCCGCCTTTTGCAGTTTAATCCACTAGGGACAGGATTGCCACCCCACAG |
| H9-6 | AGAGGCGCGCCGCCTTTTGCAGTTTAATCCACTAGGGACAGGATTGCCACCCCACAG |

Figure 25.

| Name | SEQ ID NO: | FAD2 genomic sequence　　　　　inverted donor insert | Plasmid Clones with Similar Sequence |
|---|---|---|---|
| Reference | 236 | TTACTCTCTCTACCGTGTTGCAACCCTGAAATTTCAGGGTTGCAACACGGTAGAGAGAGTAA | -- |
| 1WT3 | 237 | TTACTCTCTCTACCGTGTTGCAACCCTGA___TCAGGGTTGCAACACGGTAGAGAGAGTAA | (1WT4,5) |
| 1WT6 | 238 | TTACTCTCTCTACCGTGTTGCAACCCTGAA___AGGGTTGCAACACGGTAGAGAGAGTAA | -- |
| 4WT1 | 239 | TTACTCTCTCTACCGTGTTGCAACCCTGA___GGTTGCAACACGGTAGAGAGAGTAA | (4WT2,3,4,5) |
| 4WT4 | 240 | TTACTCTCTCTACCGTGTTGCAACCCTGAA___ 60 bp deletion | (4WT6) |
| 1HF1 | 241 | TTACTCTCTCTACCGTGTTGCAACCCTGA___TTTCAGGGTTGCAACACGGTAGAGAGAGTAA | (1HF3,5,6) |
| 1HF2 | 242 | TTACTCTCTCTACCGTGTTGCAACCCTGA___TTCAGGGTTGCAACACGGTAGAGAGAGTAA | -- |
| 1HF4 | 243 | TTACTCTCTCTACCGTGTTGCAACCCTa___TTCAGGGTTGCAACACGGTAGAGAGAGTAA | -- |
| 6HF1 | 244 | TTACTCTCTCTACCGTGTTGCAACCCTGA___TTCAGGGTTGCAACACGGTAGAGAGAGTAA | -- |
| 6HF2 | 245 | TTACTCTCTCTACCGTGTTGCAACCCTGAA___TCAGGGTTGCAACACGGTAGAGAGAGTAA | -- |
| 6HF3 | 246 | TTACTCTCTCTACCGTGTTGCAACCCTGAA___AGGGTTGCAACACGGTAGAGAGAGTAA | (6HF5,6) |
| 6HF4 | 247 | TTACTCTCTCTACCGTGTTGCAACCCTc___TTTCAGGGTTGCAACACGGTAGAGAGAGTAA | -- |

SEQUENCE LISTING

<160> NUMBER OF SEQ ID NOS: 209

<210> SEQ ID NO 1
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 1

```
Gln Ser Gly Asp Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 2

Arg Lys Asp Gln Leu Val Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 3

Arg Ser Asp Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 4

Thr Ser Ser Asn Arg Lys Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 5

Arg Ser Asp Thr Leu Ser Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 6

Ala Arg Ser Thr Arg Thr Asn
1               5

<210> SEQ ID NO 7
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 7
```

Arg Ser Asp Ser Leu Ser Val
1               5

<210> SEQ ID NO 8
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 8

Asp Arg Ser Asn Arg Lys Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 9

Gln Ser Ser His Leu Thr Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 10

Arg Ser Asp Ala Leu Ala Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 11

Arg Ser Asp Asp Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 12

Asp Pro Ser Ala Leu Arg Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 13

Arg Ser Asp Asn Leu Ser Gln

```
1               5

<210> SEQ ID NO 14
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 14

Ala Ser Asn Asp Arg Lys Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 15

Glu Arg Gly Thr Leu Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 16

Arg Ser Asp His Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 17

Glu Arg Gly Thr Leu Ala Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 18

Gln Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 19

Arg Ser Ala Asn Leu Ala Arg
1               5
```

```
<210> SEQ ID NO 20
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 20

Asp Arg Ser Asp Leu Ser Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 21

Arg Ser Asp Thr Leu Ser Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 22

Arg Ser Ala Asp Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 23

Asp Arg Ser Asn Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 24

Asn Ser Arg Asn Leu Arg Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 25

Arg Ser Asp Ser Leu Ser Val
1               5
```

```
<210> SEQ ID NO 26
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 26

Asp Arg Ser His Leu Ala Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 27

Asp Arg Ser Asn Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 28

Arg Arg Ser Asp Leu Lys Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 29

Arg Ser Asp Thr Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 30

Gln Asn Ala Thr Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 31

Gln Ser Gly Ser Leu Thr Arg
1               5
```

```
<210> SEQ ID NO 32
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 32

Gln Ser Gly Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 33

Arg Ser Asp Val Leu Ser Glu
1               5

<210> SEQ ID NO 34
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 34

Thr Arg Asn Gly Leu Lys Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 35

Arg Ser Asp Asn Leu Ser Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 36

Asp Asn Ser Asn Arg Lys Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 37

Gln Asn Ala His Arg Lys Thr
1               5

<210> SEQ ID NO 38
```

```
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 38

Gln Lys Ala Thr Arg Ile Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 39

Asp Arg Ser His Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 40

Arg Ser Asp Asp Arg Lys Lys
1               5

<210> SEQ ID NO 41
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 41

Ala Ser Lys Thr Arg Thr Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 42

Gln Ser Gly Ser Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 43

Leu Arg His His Leu Thr Arg
1               5

<210> SEQ ID NO 44
<211> LENGTH: 7
```

```
<212> TYPE: PRT
<213> ORGANISM: Artificial Sequence
<220> FEATURE:
<223> OTHER INFORMATION: Zinc Finger Protein Recognition Helices

<400> SEQUENCE: 44

Gln Ser Ala His Leu Lys Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 45

Gln Ser Gly Asp Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 46

Ala Ser His Asn Leu Arg Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 47

Asp Arg Ser Asn Leu Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 48

Gln Ser Ser Asp Leu Ser Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 49

Asp Ala Gly Asn Arg Asn Lys
1               5

<210> SEQ ID NO 50
<211> LENGTH: 7
<212> TYPE: PRT
```

<213> ORGANISM: Artificial Sequence
<220> FEATURE:
<223> OTHER INFORMATION: Zinc Finger Protein Recognition Helices

<400> SEQUENCE: 50

Asp Arg Ser Asp Leu Ser Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 51

Arg Ser Asp Asn Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 52

Asp Arg Ser His Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 53

Thr Ser Gly Asn Leu Thr Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 54

Gln Ser Ser Asp Leu Ser Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 55

Gln Ser Ser Asp Leu Ser Arg
1               5

<210> SEQ ID NO 56
<211> LENGTH: 7
<212> TYPE: PRT
<213> ORGANISM: Artificial Sequence

```
<220> FEATURE:
<223> OTHER INFORMATION: Zinc Finger Protein Recognition Helices

<400> SEQUENCE: 56

His Arg Ser Thr Arg Asn Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 57

Arg Ser Asp Asp Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 58

Asp Arg Ser Asn Leu Lys Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 59

Asp Arg Ser His Leu Thr Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 60

Gln Arg Ser Thr Leu Lys Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 61

Arg Ser Asp Ala Leu Ser Arg
1               5

<210> SEQ ID NO 62
<211> LENGTH: 7
<212> TYPE: PRT
<213> ORGANISM: Artificial Sequence
<220> FEATURE:
```

-continued

<223> OTHER INFORMATION: Zinc Finger Protein Recognition Helices

<400> SEQUENCE: 62

Arg Ser Asp Asp Leu Thr Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 63

Asp Arg Ser His Leu Thr Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 64

Thr Ser Ser Asn Arg Lys Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 65

Arg Ser Asp Thr Leu Ser Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 66

Asp Arg Ser His Leu Ala Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 67

Asp Arg Ser Ala Arg Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Zinc Finger Protein Recognition Helices

```
<400> SEQUENCE: 68

Gln Ser Gly His Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 69

Gln Ser Gly Asn Leu Ala Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 70

Arg Ser Asp Val Leu Ser Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 71

Arg Tyr Ala Tyr Leu Thr Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 72

Arg Arg Trp Thr Leu Val Gly
1               5

<210> SEQ ID NO 73
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 73

Arg Ser Asp Asn Leu Ser Gln
1               5

<210> SEQ ID NO 74
<211> LENGTH: 7
<212> TYPE: PRT
<213> ORGANISM: Artificial Sequence
<220> FEATURE:
<223> OTHER INFORMATION: Zinc Finger Protein Recognition Helices
```

<400> SEQUENCE: 74

Ala Ser Asn Asp Arg Lys Lys
1               5

<210> SEQ ID NO 75
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 75

Gln Ser Gly Asp Leu Thr Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 76

Leu Lys Asp Thr Leu Arg Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 77

Gln Ser Gly Asn Leu Ala Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 78

Gln Ser Gly Asp Leu Thr Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 79

Met Gln Asn Tyr Leu Ser Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 80

Arg Ser Asp His Leu Ser Glu
1               5

<210> SEQ ID NO 81
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 81

Gln Asn Ala Asn Arg Lys Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 82

Arg Ser Ala Asp Leu Thr Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 83

Arg Ser Asp Asn Leu Ser Glu
1               5

<210> SEQ ID NO 84
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 84

Gln Ser Ala Asn Arg Thr Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 85

Arg Ser Asp Ala Leu Ser Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 86

Asp Arg Ser Ala Leu Ala Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 87

Arg Ser Asp His Leu Ser Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 88

Asp Ser Gln Asn Arg Ile Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 89

Gln Ser Gly Asp Leu Thr Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 90

Asp Lys Gly Asn Leu Thr Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 91

Arg Ser Ala Asp Leu Thr Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 92

Asp Arg Ser His Leu Ala Arg

```
1               5

<210> SEQ ID NO 93
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 93

Arg Ser Asp Thr Leu Ser Glu
1               5

<210> SEQ ID NO 94
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 94

Asp Arg Ser Asn Arg Lys Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 95

Asp Arg Ser Asn Leu Ser Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 96

Leu Arg Gln Asp Leu Lys Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 97

Arg Ser Asp His Leu Ser Glu
1               5

<210> SEQ ID NO 98
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 98

Asp Arg Ser Ala Leu Ala Arg
1               5
```

```
<210> SEQ ID NO 99
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 99

Asp Arg Ser Ala Leu Ser Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 100

Asn Arg Arg Gly Arg Trp Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 101

Arg Pro Tyr Thr Leu Arg Leu
1               5

<210> SEQ ID NO 102
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 102

His Arg Ser Ser Leu Arg Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 103

Arg Ser Asp Ser Leu Leu Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 104

Trp Leu Ser Ser Leu Ser Ala
1               5
```

```
<210> SEQ ID NO 105
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 105

Gln Ser Gly Asp Leu Thr Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 106

Asp Arg Ser His Leu Ala Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 107

Asp Arg Ser Asn Leu Ser Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 108

Leu Lys Gln His Leu Asn Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 109

Leu Arg His His Leu Thr Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 110

Gln Ser Gly Asn Leu His Val
1               5
```

```
<210> SEQ ID NO 111
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 111

Thr Ser Gly His Leu Ser Arg
1               5

<210> SEQ ID NO 112
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 112
ctactccgta tgcgaaggca cg                                              22

<210> SEQ ID NO 113
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 113
tattcgcggt gggacacttg at                                              22

<210> SEQ ID NO 114
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 114
ccggagccgg ggcctcccag gc                                              22

<210> SEQ ID NO 115
<211> LENGTH: 23
<212> TYPE: DNA
<213> ORGANISM: Artificial Sequence
<220> FEATURE:
<223> OTHER INFORMATION: Zinc Finger Binding Sequences

<400> SEQUENCE: 115
atcgcgacgc gacgcgacga gac                                             23

<210> SEQ ID NO 116
<211> LENGTH: 13
<212> TYPE: DNA
<213> ORGANISM: Artificial Sequence
<220> FEATURE:
<223> OTHER INFORMATION: Zinc Finger Binding Sequences

<400> SEQUENCE: 116
tgcatgcgca gta                                                        13

<210> SEQ ID NO 117
<211> LENGTH: 18
<212> TYPE: DNA
<213> ORGANISM: Artificial Sequence
<220> FEATURE:
<223> OTHER INFORMATION: Zinc Finger Binding Sequences
```

<400> SEQUENCE: 117
acaccggcgc acggcacg                                          18

<210> SEQ ID NO 118
<211> LENGTH: 12
<212> TYPE: DNA
<213> ORGANISM: Artificial Sequence
<220> FEATURE:
<223> OTHER INFORMATION: Zinc Finger Binding Sequences

<400> SEQUENCE: 118
agaggtgtaa cc                                                12

<210> SEQ ID NO 119
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 119
tcgggcacaa gaaacgag                                          18

<210> SEQ ID NO 120
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 120
tacgctgaca atgca                                             15

<210> SEQ ID NO 121
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 121
ccagctgatg gagaggac                                          18

<210> SEQ ID NO 122
<211> LENGTH: 12
<212> TYPE: DNA
<213> ORGANISM: Artificial Sequence
<220> FEATURE:
<223> OTHER INFORMATION: Zinc Finger Binding Sequences

<400> SEQUENCE: 122
agagcaggcg ag                                                12

<210> SEQ ID NO 123
<211> LENGTH: 16
<212> TYPE: DNA
<213> ORGANISM: Artificial Sequence
<220> FEATURE:
<223> OTHER INFORMATION: Zinc Finger Binding Sequences

<400> SEQUENCE: 123
agcaaagtga gtagtt                                            16

<210> SEQ ID NO 124

```
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 124
tggatggaag gaatc                                                       15

<210> SEQ ID NO 125
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 125
gaagctacat cccag                                                       15

<210> SEQ ID NO 126
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 126
tacgcgcaac ggaacgca                                                    18

<210> SEQ ID NO 127
<211> LENGTH: 19
<212> TYPE: DNA
<213> ORGANISM: Artificial Sequence
<220> FEATURE:
<223> OTHER INFORMATION: Zinc Finger Binding Sequences

<400> SEQUENCE: 127
caccggtgtc gtgtaacag                                                   19

<210> SEQ ID NO 128
<211> LENGTH: 16
<212> TYPE: DNA
<213> ORGANISM: Artificial Sequence
<220> FEATURE:
<223> OTHER INFORMATION: Zinc Finger Binding Sequences

<400> SEQUENCE: 128
cccggacgac gccgag                                                      16

<210> SEQ ID NO 129
<211> LENGTH: 20
<212> TYPE: DNA
<213> ORGANISM: Artificial Sequence
<220> FEATURE:
<223> OTHER INFORMATION: Zinc Finger Binding Sequences

<400> SEQUENCE: 129
gacatggcac gcgcatcgag                                                  20

<210> SEQ ID NO 130
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 130
```

```
gcatgtgtgg ttttg                                                 15

<210> SEQ ID NO 131
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 131
ggtcaaggta gtgac                                                 15

<210> SEQ ID NO 132
<211> LENGTH: 2378
<212> TYPE: DNA
<213> ORGANISM: Artificial Sequence
<220> FEATURE:
<223> OTHER INFORMATION: universal polynucleotide donor cassette
      sequence

<400> SEQUENCE: 132
aagttggtga tacatgaacc aacacgaaga acccgccagt cctactacca ctctccttcg    60
tttgacctag ctggctggtt aagaaactga tgttgatacc agccactact ccgagctagt   120
agtaaaagat ttttacagcc aggggagcca caggttagta gagtggtagg agcagtgttg   180
gactgatggc tcgcttacat aagcagttct gtcccatgga gccaatgtcc tgatacggta   240
ggacacatat cccttaatga atcggccaac gcgcggggag aggcggtttg cgtattgggc   300
gctcttccgc ttcctcgctc actgactcgc tgcgctcggt cgttcggctg cggcgagcgg   360
tatcagctca ctcaaaggcg gtaatacggt tatccacaga atcaggggat aacgcaggaa   420
agaacatgtg agcaaaaggc cagcaaaagg ccaggaaccg taaaaaggcc gcgttgctgg   480 cgttttttcca taggctccgc cccctgacg agcatcacaa aaatcgacgc tcaagtcaga   540
ggtggcgaaa cccgacagga ctataaagat accaggcgtt tcccctgga agctccctcg   600 tgcgctctcc tgttccgacc ctgccgctta ccggatacct gtccgccttt ctcccttcgg   660
gaagcgtggc gctttctcat agctcacgct gtaggtatct cagttcggtg taggtcgttc   720
gctccaagct gggctgtgtg cacgaacccc ccgttcagcc cgaccgctgc gccttatccg   780
gtaactatcg tcttgagtcc aacccggtaa gacacgactt atcgccactg gcagcagcca   840
ctggtaacag gattagcaga gcgaggtatg taggcggtgc tacagagttc ttgaagtggt   900
ggcctaacta cggctacact agaagaacag tatttggtat ctgcgctctg ctgaagccag   960
ttaccttcgg aaaaagagtt ggtagctctt gatccggcaa acaaaccacc gctggtagcg  1020
gtggtttttt tgtttgcaag cagcagatta cgcgcagaaa aaaaggatct caagaagatc  1080
ctttgatctt ttctacgggg tctgacgctc agtggaacga aaactcacgt taagggattt  1140
tggtcatggc gttcggaacc gtgctgaccc gcaagtggca acctcccgtg cctctgctca  1200
cctttaccgc ctggcaactg gcggccacct gcagggcgat cgcaccgagc gcttagtggg  1260
aatttgtacc ccttatcgaa ccgggagcac aggatgacgc taacaattc attcaagccg  1320 acaccgcttc gcggcgcggc ttaattcagg agttaaacat catgagggaa gcggtgatcg  1380
ccgaagtatc gactcaacta tcagaggtag ttggcgtcat cgagcgccat ctcgaaccga  1440
cgttgctggc cgtacatttg tacggctccg cagtggatgg cggcctgaag ccacacagtg  1500
atattgattt gctggttacg gtgaccgtaa ggcttgatga acaacgcgg cgagctttga  1560 tcaacgacct tttggaaact tcggcttccc ctggagagag cgagattctc cgcgctgtag  1620
```

-continued

```
aagtcaccat tgttgtgcac gacgacatca ttccgtggcg ttatccagct aagcgcgaac    1680
tgcaatttgg agaatggcag cgcaatgaca ttcttgcagg tatcttcgag ccagccacga    1740
tcgacattga tctggctatc ttgctgacaa aagcaagaga acatagcgtt gccttggtag    1800
gtccagcggc ggaggaactc tttgatccgg ttcctgaaca ggatctattt gaggcgctaa    1860
atgaaacctt aacgctatgg aactcgccgc ccgactgggc tggcgatgag cgaaatgtag    1920
tgcttacgtt gtcccgcatt tggtacagcg cagtaaccgg caaaatcgcg ccgaaggatg    1980
tcgctgccga ctgggcaatg gagcgcctgc cggcccagta tcagcccgtc atacttgaag    2040
ctaggcaggc ttatcttgga caagaagatc gcttggcctc gcgcgcagat cagttggaag    2100
aatttgttca ctacgtgaaa ggcgagatca ccaaggtagt cggcaaataa tgtctaacaa    2160
ttcgttcaag ccgacgccgc ttcgcggcgc ggcttaactc aagcgttaga gagctgggga    2220
agactatgcg cgatcgcctg cagctacgtg ccttcgcata cggagtagtt tattcgcggt    2280
gggacacttg atagaaaggt taagaggaca cgcctaaaca gttgtgaata catacataca    2340
caccgataca cagatgctaa agcactaaag cccctaaa                            2378
```

<210> SEQ ID NO 133
<211> LENGTH: 2424
<212> TYPE: DNA
<213> ORGANISM: Artificial Sequence
<220> FEATURE:
<223> OTHER INFORMATION: universal polynucleotide donor cassette
      sequence

<400> SEQUENCE: 133

```
tttgcgggat ctggatgggc tgttttcgcg cgcggcgtca ctttcccttta acttctcgcg      60 ctggaagagg cagctgcctg cttttgcttg gccgctgacc atgacacctg gccccgcttt     120
gcagcccgtg gaggactctt ggcgagccac aggttagtag agtggtagga gcagtgttgg     180
actgatggct cgcttacata agcagttctg tcccatggag ccaatgtcct gatacggtag     240
gacacatatc ccttaatgaa tcggccaacg cgcggggaga ggcggtttgc gtattgggcg     300
ctcttccgct tcctcgctca ctgactcgct gcgctcggtc gttcggctgc ggcgagcggt     360
atcagctcac tcaaaggcgg taatacggtt atccacagaa tcaggggata acgcaggaaa     420
gaacatgtga gcaaaaggcc agcaaaaggc caggaaccgt aaaaaggccg cgttgctggc     480
gtttttccat aggctccgcc ccctgacga gcatcacaaa aatcgacgct caagtcagag     540
gtggcgaaac ccgacaggac tataaagata ccaggcgttt ccccctggaa gctccctcgt     600
gcgctctcct gttccgaccc tgccgcttac cggatacctg tccgcctttc tcccttcggg     660
aagcgtggcg ctttctcata gctcacgctg taggtatctc agttcggtgt aggtcgttcg     720
ctccaagctg ggctgtgtgc acgaaccccc cgttcagccc gaccgctgcg ccttatccgg     780
taactatcgt cttgagtcca acccggtaag acacgactta tcgccactgg cagcagccac     840
tggtaacagg attagcagag cgaggtatgt aggcggtgct acagagttct tgaagtggtg     900
gcctaactac ggctacacta gaagaacagt atttggtatc tgcgctctgc tgaagccagt     960
taccttcgga aaaagagttg gtagctcttg atccggcaaa caaaccaccg ctggtagcgg    1020 tggtttttttt gtttgcaagc agcagattac gcgcagaaaa aaaggatctc aagaagatcc    1080
tttgatcttt tctacggggt ctgacgctca gtggaacgaa aactcacgtt aagggatttt    1140
ggtcatggcg ttcggaaccg tgctgacccg caagtgcaa cctcccgtgc ctctgctcac    1200
ctttaccgcc tggcaactgg cggccacctg cagggcgatc gcaccgagcg cttagtggga    1260
```

-continued

| | |
|---|---|
| atttgtaccc cttatcgaac cgggagcaca ggatgacgcc taacaattca ttcaagccga | 1320 |
| caccgcttcg cggcgcggct taattcagga gttaaacatc atgagggaag cggtgatcgc | 1380 |
| cgaagtatcg actcaactat cagaggtagt tggcgtcatc gagcgccatc tcgaaccgac | 1440 |
| gttgctggcc gtacatttgt acggctccgc agtggatggc ggcctgaagc cacacagtga | 1500 |
| tattgatttg ctggttacgg tgaccgtaag gcttgatgaa caacgcggc gagctttgat | 1560 |
| caacgacctt ttggaaactt cggcttcccc tggagagagc gagattctcc gcgctgtaga | 1620 |
| agtcaccatt gttgtgcacg acgacatcat tccgtggcgt tatccagcta agcgcgaact | 1680 |
| gcaatttgga gaatggcagc gcaatgacat tcttgcaggt atcttcgagc cagccacgat | 1740 |
| cgacattgat ctggctatct tgctgacaaa agcaagagaa catagcgttg ccttggtagg | 1800 |
| tccagcggcg gaggaactct ttgatccggt tcctgaacag gatctatttg aggcgctaaa | 1860 |
| tgaaacctta acgctatgga actcgccgcc cgactgggct ggcgatgagc gaaatgtagt | 1920 |
| gcttacgttg tcccgcattt ggtacagcgc agtaaccggc aaaatcgcgc cgaaggatgt | 1980 |
| cgctgccgac tgggcaatgg agcgcctgcc ggcccagtat cagcccgtca tacttgaagc | 2040 |
| taggcaggct tatcttggac aagaagatcg cttggcctcg cgcgcagatc agttggaaga | 2100 |
| atttgttcac tacgtgaaag gcgagatcac caaggtagtc ggcaaataat gtctaacaat | 2160 |
| tcgttcaagc cgacgccgct tcgcggcgcg gcttaactca agcgttagag agctggggaa | 2220 |
| gactatgcgc gatcgcctgc aggtggttgc ctgggaggcc ccggctccgg gcatcgcgac | 2280 |
| gcgacgcgac gagacgcgta aaagtcaccc gtcgcggtct cgcatgcgcg agggaggcag | 2340 |
| gcaggcagcg aacaaaatcg cacgcgcgtc gtcgactgcc tggcctggcc tggtccagct | 2400 |
| gaaaaccgcc ccggtttgcc tccg | 2424 |

<210> SEQ ID NO 134
<211> LENGTH: 2225
<212> TYPE: DNA
<213> ORGANISM: Artificial Sequence
<220> FEATURE:
<223> OTHER INFORMATION: universal polynucleotide donor cassette
      sequence

<400> SEQUENCE: 134

| | |
|---|---|
| gcgtattggg cgctcttccg cttcctcgct cactgactcg ctgcgctcgg tcgttcggct | 60 |
| gcggcgagcg gtatcagctc actcaaaggc ggtaatacgg ttatccacag aatcagggga | 120 |
| taacgcagga aagaacatgt gagcaaaagg ccagcaaaag gccaggaacc gtaaaaaggc | 180 |
| cgcgttgctg gcgtttttcc ataggctccg cccccctgac gagcatcaca aaaatcgacg | 240 |
| ctcaagtcag aggtggcgaa acccgacagg actataaaga taccaggcgt ttccccctgg | 300 |
| aagctccctc gtgcgctctc ctgttccgac cctgccgctt accggatacc tgtccgcctt | 360 |
| tctcccttcg ggaagcgtgg cgctttctca tagctcacgc tgtaggtatc tcagttcggt | 420 |
| gtaggtcgtt cgctccaagc tgggctgtgt gcacgaaccc cccgttcagc ccgaccgctg | 480 |
| cgccttatcc ggtaactatc gtcttgagtc aacccggta agacacgact tatcgccact | 540 |
| ggcagcagcc actggtaaca ggattagcag agcgaggtat gtaggcggtg ctacagagtt | 600 |
| cttgaagtgg tggcctaact acggctacac tagaagaaca gtatttggta tctgcgctct | 660 |
| gctgaagcca gttaccttcg gaaaaagagt tggtagctct tgatccggca aacaaaccac | 720 |
| cgctggtagc ggtggttttt ttgtttgcaa gcagcagatt acgcgcagaa aaaaggatc | 780 |
| tcaagaagat cctttgatct tttctacggg gtctgacgct cagtggaacg aaaactcacg | 840 |

```
ttaagggatt ttggtcatgg cgttcggaac cgtgctgacc cgcaagtggc aacctcccgt      900
gcctctgctc acctttaccg cctggcaact ggcggccacc tgcagggcga tcgcaccgag      960
cgcttagtgg gaatttgtac cccttatcga accgggagca caggatgacg cctaacaatt     1020
cattcaagcc gacaccgctt cgcggcgcgg cttaattcag gagttaaaca tcatgaggga     1080
agcggtgatc gccgaagtat cgactcaact atcagaggta gttggcgtca tcgagcgcca     1140
tctcgaaccg acgttgctgg ccgtacattt gtacggctcc gcagtggatg gcggcctgaa     1200
gccacacagt gatattgatt tgctggttac ggtgaccgta aggcttgatg aaacaacgcg     1260
gcgagctttg atcaacgacc ttttggaaac ttcggcttcc cctggagaga gcgagattct     1320
ccgcgctgta gaagtcacca ttgttgtgca cgacgacatc attccgtggc gttatccagc     1380
taagcgcgaa ctgcaatttg gagaatggca gcgcaatgac attcttgcag gtatcttcga     1440
gccagccacg atcgacattg atctggctat cttgctgaca aaagcaagag aacatagcgt     1500
tgccttggta ggtccagcgg cggaggaact ctttgatccg gttcctgaac aggatctatt     1560
tgaggcgcta aatgaaacct aacgctatg gaactcgccg cccgactggg ctggcgatga     1620
gcgaaatgta gtgcttacgt tgtcccgcat ttggtacagc gcagtaaccg gcaaaatcgc     1680
gccgaaggat gtcgctgccg actgggcaat ggagcgcctg ccggcccagt atcagcccgt     1740
catacttgaa gctaggcagg cttatcttgg acaagaagat cgcttggcct cgcgcgcaga     1800
tcagttggaa gaatttgttc actacgtgaa aggcgagatc accaaggtag tcggcaaata     1860
atgtctaaca attcgttcaa gccgacgccg cttcgcggcg cggcttaact caagcgttag     1920
agagctgggg aagactatgc gcgatcgcct gcagtccgca gttaccttcc ccatcatgaa     1980
cttggagacc gaaaggtgtg gtgcctagtt accccgaaga aatgaaacat ctgcattgtc     2040
agcgtagtat cccagctgat ggagaggaca tacccatgag gagccacagg ttagtagagt     2100
ggtaggagca gtgttggact gatggctcgc ttacataagc agttctgtcc catggagcca     2160
atgtcctgat acggtaggac acatatccct taatgaatcg gccaacgcgc ggggagaggc     2220
ggttt                                                                  2225
```

<210> SEQ ID NO 135
<211> LENGTH: 2234
<212> TYPE: DNA
<213> ORGANISM: Artificial Sequence
<220> FEATURE:
<223> OTHER INFORMATION: universal polynucleotide donor cassette
       sequence

<400> SEQUENCE: 135

```
gagagctggg gaagactatg cgcgatcgcc tgcagtgtcg cgaggcaggg agcagccgcg       60
tgtccgcctg ctgctgctgg aatggcgcgg tggccgcgcg cggtgacgtc ggcaaggctg      120
gtctcgcctg ctcttggcaa gcaaagtgag tagttacacg gcgctggctg gagccacagg      180
ttagtagagt ggtaggagca gtgttggact gatggctcgc ttacataagc agttctgtcc      240
catggagcca atgtcctgat acggtaggac acatatccct taatgaatcg gccaacgcgc      300
ggggagaggc ggtttgcgta ttgggcgctc ttccgcttcc tcgctcactg actcgctgcg      360
ctcggtcgtt cggctgcggc gagcggtatc agctcactca aaggcggtaa tacggttatc      420
cacagaatca ggggataacg caggaaagaa catgtgagca aaaggccagc aaaaggccag      480
gaaccgtaaa aaggccgcgt tgctggcgtt tttccatagg ctccgccccc ctgacgagca      540
tcacaaaaat cgacgctcaa gtcagaggtg gcgaaacccg acaggactat aaagatacca      600
```

```
ggcgtttccc cctggaagct ccctcgtgcg ctctcctgtt ccgaccctgc cgcttaccgg      660
atacctgtcc gcctttctcc cttcgggaag cgtggcgctt tctcatagct cacgctgtag      720
gtatctcagt tcggtgtagg tcgttcgctc caagctgggc tgtgtgcacg aaccccccgt      780
tcagcccgac cgctgcgcct tatccggtaa ctatcgtctt gagtccaacc cggtaagaca      840
cgacttatcg ccactggcag cagccactgg taacaggatt agcagagcga ggtatgtagg      900
cggtgctaca gagttcttga agtggtggcc taactacggc tacactagaa gaacagtatt      960
tggtatctgc gctctgctga agccagttac cttcggaaaa agagttggta gctcttgatc     1020
cggcaaacaa accaccgctg gtagcggtgg ttttttttgtt tgcaagcagc agattacgcg     1080
cagaaaaaaa ggatctcaag aagatccttt gatcttttct acggggtctg acgctcagtg     1140
gaacgaaaac tcacgttaag ggattttggt catggcgttc ggaaccgtgc tgacccgcaa     1200 gtggcaaccct cccgtgcctc tgctcacctt taccgcctgg caactggcgg ccacctgcag     1260
ggcgatcgca ccgagcgctt agtgggaatt tgtaccccctt atcgaaccgg gagcacagga    1320
tgacgcctaa caattcattc aagccgacac cgcttcgcgg cgcggcttaa ttcaggagtt     1380
aaacatcatg agggaagcgg tgatcgccga agtatcgact caactatcag aggtagttgg     1440
cgtcatcgag cgccatctcg aaccgacgtt gctggccgta catttgtacg gctccgcagt     1500
ggatggcggc ctgaagccac acagtgatat tgatttgctg gttacggtga ccgtaaggct     1560
tgatgaaaca acgcggcgag ctttgatcaa cgaccttttg gaaacttcgg cttccccctgg    1620 agagagcgag attctccgcg ctgtagaagt caccattgtt gtgcacgacg acatcattcc     1680
gtggcgttat ccagctaagc gcgaactgca atttggagaa tggcagcgca atgacattct     1740
tgcaggtatc ttcgagccag ccacgatcga cattgatctg gctatcttgc tgacaaaagc     1800
aagagaacat agcgttgcct tggtaggtcc agcggcggag gaactctttg atccggttcc     1860
tgaacaggat ctatttgagg cgctaaatga aaccttaacg ctatggaact cgccgcccga     1920
ctgggctggc gatgagcgaa atgtagtgct tacgttgtcc cgcatttggt acagcgcagt     1980
aaccggcaaa atcgcgccga aggatgtcgc tgccgactgg gcaatggagc gcctgccggc     2040
ccagtatcag cccgtcatac ttgaagctag gcaggcttat cttggacaag aagatcgctt     2100
ggcctcgcgc gcagatcagt tggaagaatt tgttcactac gtgaaaggcg agatcaccaa     2160
ggtagtcggc aaataatgtc taacaattcg ttcaagccga cgccgcttcg cggcgcggct     2220
taactcaagc gtta                                                       2234
```

<210> SEQ ID NO 136
<211> LENGTH: 2165
<212> TYPE: DNA
<213> ORGANISM: Artificial Sequence
<220> FEATURE:
<223> OTHER INFORMATION: universal polynucleotide donor cassette
      sequence

<400> SEQUENCE: 136

```
gagagctggg gaagactatg cgcgatcgcc tgcagtgttg tgcagccgta cgtgccgtgc       60
gccggtgtat gtctgcatgc gcagtactta ttttctgaag cgagccacag gttagtagag      120
tggtaggagc agtgttggac tgatggctcg cttacataag cagttctgtc ccatggagcc      180
aatgtcctga tacggtagga cacatatccc ttaatgaatc ggccaacgcg cggggagagg      240 cggtttcgt attgggcgct cttccgcttc ctcgctcact gactcgctgc gctcggtcgt       300
tcggctgcgg cgagcggtat cagctcactc aaaggcggta atacggttat ccacagaatc      360
```

```
aggggataac gcaggaaaga acatgtgagc aaaaggccag caaaaggcca ggaaccgtaa    420
aaaggccgcg ttgctggcgt ttttccatag gctccgcccc cctgacgagc atcacaaaaa    480
tcgacgctca agtcagaggt ggcgaaaccc gacaggacta taaagatacc aggcgtttcc    540
ccctggaagc tccctcgtgc gctctcctgt tccgaccctg ccgcttaccg gatacctgtc    600
cgcctttctc ccttcgggaa gcgtggcgct ttctcatagc tcacgctgta ggtatctcag    660
ttcggtgtag gtcgttcgct ccaagctggg ctgtgtgcac gaaccccccg ttcagcccga    720
ccgctgcgcc ttatccggta actatcgtct tgagtccaac ccggtaagac acgacttatc    780
gccactggca gcagccactg gtaacaggat tagcagagcg aggtatgtag gcggtgctac    840
agagttcttg aagtggtggc ctaactacgg ctacactaga agaacagtat ttggtatctg    900
cgctctgctg aagccagtta ccttcggaaa aagagttggt agctcttgat ccggcaaaca    960
aaccaccgct ggtagcggtg gttttttgt ttgcaagcag cagattacgc gcagaaaaaa   1020
aggatctcaa gaagatcctt tgatctttc tacgggtct gacgctcagt ggaacgaaaa   1080
ctcacgttaa gggattttgg tcatggcgtt cggaaccgtg ctgacccgca agtggcaacc   1140
tcccgtgcct ctgctcacct ttaccgcctg gcaactggcg gccacctgca gggcgatcgc   1200
accgagcgct tagtgggaat ttgtaccct tatcgaaccg ggagcacagg atgacgccta   1260
acaattcatt caagccgaca ccgcttcgcg gcgcggctta attcaggagt taaacatcat   1320
gagggaagcg gtgatcgccg aagtatcgac tcaactatca gaggtagttg gcgtcatcga   1380
gcgccatctc gaaccgacgt tgctggccgt acatttgtac ggctccgcag tggatggcgg   1440
cctgaagcca cacagtgata ttgatttgct ggttacggtg accgtaaggc ttgatgaaac   1500
aacgcggcga gctttgatca acgacctttt ggaaacttcg gcttccctg gagagagcga   1560 gattctccgc gctgtagaag tcaccattgt tgtgcacgac gacatcattc cgtggcgtta   1620
tccagctaag cgcgaactgc aatttggaga atggcagcgc aatgacattc ttgcaggtat   1680
cttcgagcca gccacgatcg acattgatct ggctatcttg ctgacaaaag caagagaaca   1740
tagcgttgcc ttggtaggtc cagcggcgga ggaactcttt gatccggttc ctgaacagga   1800
tctatttgag gcgctaaatg aaaccttaac gctatggaac tcgccgcccg actgggctgg   1860
cgatgagcga aatgtagtgc ttacgttgtc ccgcatttgg tacagcgcag taaccggcaa   1920
aatcgcgccg aaggatgtcg ctgccgactg gcaatggagc gcctgccgg cccagtatca   1980 gcccgtcata cttgaagcta ggcaggctta tcttggacaa gaagatcgct tggcctcgcg   2040
cgcagatcag ttggaagaat ttgttcacta cgtgaaaggc gagatcacca aggtagtcgg   2100
caaataatgt ctaacaattc gttcaagccg acgccgcttc gcggcgcggc ttaactcaag   2160
cgtta                                                              2165

<210> SEQ ID NO 137
<211> LENGTH: 2264
<212> TYPE: DNA
<213> ORGANISM: Artificial Sequence
<220> FEATURE:
<223> OTHER INFORMATION: universal polynucleotide donor cassette
      sequence

<400> SEQUENCE: 137
gagagctggg gaagactatg cgcgatcgcc tgcagtaacg atttattttc ctcgtttctt     60
gtgcccgaaa gagagaggtg taacccatcc tctataacag tgtggctttg acaacggttc    120
aatatgtatg tttggcaaat gtagatttgt gccaattctt ggtcataatc agcgcggaca    180
```

```
aaccggctac ccaaatttgg gagccacagg ttagtagagt ggtaggagca gtgttggact      240
gatggctcgc ttacataagc agttctgtcc catggagcca atgtcctgat acggtaggac      300
acatatccct taatgaatcg gccaacgcgc ggggagaggc ggtttgcgta ttgggcgctc      360
ttccgcttcc tcgctcactg actcgctgcg ctcggtcgtt cggctgcggc gagcggtatc      420
agctcactca aaggcggtaa tacggttatc cacagaatca ggggataacg caggaaagaa      480
catgtgagca aaaggccagc aaaaggccag gaaccgtaaa aaggccgcgt tgctggcgtt      540
tttccatagg ctccgccccc ctgacgagca tcacaaaaat cgacgctcaa gtcagaggtg      600
gcgaaacccg acaggactat aaagatacca ggcgtttccc cctggaagct ccctcgtgcg      660
ctctcctgtt ccgaccctgc cgcttaccgg atacctgtcc gcctttctcc cttcgggaag      720
cgtggcgctt tctcatagct cacgctgtag gtatctcagt tcggtgtagg tcgttcgctc      780
caagctgggc tgtgtgcacg aaccccccgt tcagcccgac cgctgcgcct tatccggtaa      840
ctatcgtctt gagtccaacc cggtaagaca cgacttatcg ccactggcag cagccactgg      900
taacaggatt agcagagcga ggtatgtagg cggtgctaca gagttcttga agtggtggcc      960
taactacggc tacactagaa gaacagtatt tggtatctgc gctctgctga agccagttac     1020
cttcggaaaa agagttggta gctcttgatc cggcaaacaa accaccgctg gtagcggtgg     1080
tttttttgtt tgcaagcagc agattacgcg cagaaaaaaa ggatctcaag aagatccttt     1140
gatcttttct acggggtctg acgctcagtg gaacgaaaac tcacgttaag ggattttggt     1200 catgcgttc ggaaccgtgc tgacccgcaa gtggcaacct cccgtgcctc tgctcacctt     1260
taccgcctgg caactggcgg ccacctgcag ggcgatcgca ccgagcgctt agtgggaatt     1320 tgtaccccctt atcgaaccgg gagcacagga tgacgcctaa caattcattc aagccgacac     1380
cgcttcgcgg cgcggcttaa ttcaggagtt aaacatcatg agggaagcgg tgatcgccga     1440
agtatcgact caactatcag aggtagttgg cgtcatcgag cgccatctcg aaccgacgtt     1500
gctggccgta catttgtacg gctccgcagt ggatggcggc ctgaagccac acagtgatat     1560
tgatttgctg gttacggtga ccgtaaggct tgatgaaaca acgcggcgag ctttgatcaa     1620 cgacctttg gaaacttcgg cttcccctgg agagagcgag attctccgcg ctgtagaagt     1680
caccattgtt gtgcacgacg acatcattcc gtggcgttat ccagctaagc gcgaactgca     1740
atttggagaa tggcagcgca atgacattct tgcaggtatc ttcgagccag ccacgatcga     1800
cattgatctg gctatcttgc tgacaaaagc aagagaacat agcgttgcct tggtaggtcc     1860
agcggcggag gaactctttg atccggttcc tgaacaggat ctatttgagg cgctaaatga     1920
aaccttaacg ctatggaact cgccgcccga ctgggctggc gatgagcgaa atgtagtgct     1980
tacgttgtcc cgcatttggt acagcgcagt aaccggcaaa tcgcgccga aggatgtcgc     2040 tgccgactgg gcaatggagc gcctgccggc ccagtatcag cccgtcatac ttgaagctag     2100
gcaggcttat cttggacaag aagatcgctt ggcctcgcgc gcagatcagt tggaagaatt     2160
tgttcactac gtgaaaggcg agatcaccaa ggtagtcggc aaataatgtc taacaattcg     2220
ttcaagccga cgccgcttcg cggcgcggct taactcaagc gtta                      2264
```

<210> SEQ ID NO 138
<211> LENGTH: 2373
<212> TYPE: DNA
<213> ORGANISM: Artificial Sequence
<220> FEATURE:
<223> OTHER INFORMATION: universal polynucleotide donor cassette
      sequence

<400> SEQUENCE: 138

```
gcgtattggg cgctcttccg cttcctcgct cactgactcg ctgcgctcgg tcgttcggct        60
gcggcgagcg gtatcagctc actcaaaggc ggtaatacgg ttatccacag aatcagggga       120
taacgcagga aagaacatgt gagcaaaagg ccagcaaaag gccaggaacc gtaaaaaggc       180
cgcgttgctg gcgttttcc ataggctccg cccccctgac gagcatcaca aaaatcgacg       240
ctcaagtcag aggtggcgaa acccgacagg actataaaga taccaggcgt ttccccctgg       300
aagctccctc gtgcgctctc ctgttccgac cctgccgctt accggatacc tgtccgcctt       360
tctcccttcg ggaagcgtgg cgctttctca tagctcacgc tgtaggtatc tcagttcggt       420
gtaggtcgtt cgctccaagc tgggctgtgt gcacgaaccc cccgttcagc ccgaccgctg       480
cgccttatcc ggtaactatc gtcttgagtc caacccggta agacacgact tatcgccact       540
ggcagcagcc actggtaaca ggattagcag agcgaggtat gtaggcggtg ctacagagtt       600
cttgaagtgg tggcctaact acggctacac tagaagaaca gtatttggta tctgcgctct       660
gctgaagcca gttaccttcg gaaaaagagt tggtagctct tgatccggca aacaaaccac       720
cgctggtagc ggtggttttt ttgtttgcaa gcagcagatt acgcgcagaa aaaaaggatc       780
tcaagaagat cctttgatct tttctacggg gtctgacgct cagtggaacg aaaactcacg       840
ttaagggatt ttggtcatgg cgttcggaac cgtgctgacc cgcaagtggc aacctcccgt       900
gcctctgctc acctttaccg cctggcaact ggcggccacc tgcagggcga tcgcaccgag       960
cgcttagtgg gaatttgtac cccttatcga accgggagca caggatgacg cctaacaatt      1020
cattcaagcc gacaccgctt cgcggcgcgg cttaattcag gagttaaaca tcatgaggga      1080
agcggtgatc gccgaagtat cgactcaact atcagaggta gttggcgtca tcgagcgcca      1140
tctcgaaccg acgttgctgg ccgtacattt gtacggctcc gcagtggatg gcggcctgaa      1200
gccacacagt gatattgatt tgctggttac ggtgaccgta aggcttgatg aaacaacgcg      1260
gcgagctttg atcaacgacc ttttggaaac ttcggcttcc cctggagaga gcgagattct      1320
ccgcgctgta gaagtcacca ttgttgtgca cgacgacatc attccgtggc gttatccagc      1380
taagcgcgaa ctgcaatttg gagaatggca gcgcaatgac attcttgcag gtatcttcga      1440
gccagccacg atcgacattg atctggctat cttgctgaca aaagcaagag aacatagcgt      1500
tgccttggta ggtccagcgg cggaggaact ctttgatccg gttcctgaac aggatctatt      1560
tgaggcgcta aatgaaacct taacgctatg gaactcgccg cccgactggg ctggcgatga      1620
gcgaaatgta gtgcttacgt tgtcccgcat ttggtacagc gcagtaaccg gcaaaatcgc      1680
gccgaaggat gtcgctgccg actgggcaat ggagcgcctg ccggcccagt atcagcccgt      1740
catacttgaa gctaggcagg cttatcttgg acaagaagat cgcttggcct cgcgcgcaga      1800
tcagttggaa gaatttgttc actacgtgaa aggcgagatc accaaggtag tcggcaaata      1860
atgtctaaca attcgttcaa gccgacgccg cttcgcggcg cggcttaact caagcgttag      1920
agagctgggg aagactatgc gcgatcgcct gcagataagg aactatatac aaaaccacac      1980
atgcacacgt ggtcaaggta gtgactaatc tcgcctaata cacggcgctg gctgatgcat      2040
gcgtgacacg gtggctagct agctgttgat cccggccggc ccgtgatgac agcgctcggc      2100
gtcttcaggc ttcagaaccg ttgatcaagg acgatgagct tgagagctga atccgcggtt      2160
cgtggtgttc atctcagcgt gtctcgtcgt cggcccggtc ggcagcggca gaatttcatt      2220
tcagactgga gccacaggtt agtagagtgg taggagcagt gttggactga tggctcgctt      2280
```
acataagcag ttctgtccca tggagccaat gtcctgatac ggtaggacac atatccctta 2340
atgaatcggc caacgcgcgg ggagaggcgg ttt 2373

<210> SEQ ID NO 139
<211> LENGTH: 2241
<212> TYPE: DNA
<213> ORGANISM: Artificial Sequence
<220> FEATURE:
<223> OTHER INFORMATION: universal polynucleotide donor cassette sequence

<400> SEQUENCE: 139
gagagctggg gaagactatg cgcgatcgcc tgcaggagct tgcattaact agcaaagtga 60
ttccttccat ccatgcaaga agctacatcc cagtgggtgc ggcaaaagct gtatgaaaag 120
gttggagact tccatacaac tgttgtgtgt cgagtagtag aaaccaacaa caaagtcgag 180
ccacaggtta gtagagtggt aggagcagtg ttggactgat ggctcgctta cataagcagt 240
tctgtcccat ggagccaatg tcctgatacg gtaggacaca tatcccttaa tgaatcggcc 300
aacgcgcggg gagaggcggt ttgcgtattg ggcgctcttc cgcttcctcg ctcactgact 360
cgctgcgctc ggtcgttcgg ctgcggcgag cggtatcagc tcactcaaag gcggtaatac 420
ggttatccac agaatcaggg gataacgcag gaaagaacat gtgagcaaaa ggccagcaaa 480
aggccaggaa ccgtaaaaag gccgcgttgc tggcgttttt ccataggctc cgcccccctg 540
acgagcatca aaaaatcga cgctcaagtc agaggtggcg aaacccgaca ggactataaa 600
gataccaggc gtttccccct ggaagctccc tcgtgcgctc tcctgttccg accctgccgc 660
ttaccggata cctgtccgcc tttctccctt cgggaagcgt ggcgctttct catagctcac 720
gctgtaggta tctcagttcg gtgtaggtcg ttcgctccaa gctgggctgt gtgcacgaac 780
cccccgttca gcccgaccgc tgcgccttat ccggtaacta tcgtcttgag tccaacccgg 840
taagacacga cttatcgcca ctggcagcag ccactggtaa caggattagc agagcgaggt 900
atgtaggcgg tgctacagag ttcttgaagt ggtggcctaa ctacggctac actagaagaa 960
cagtatttgg tatctgcgct ctgctgaagc cagttacctt cggaaaaaga gttggtagct 1020
cttgatccgg caaacaaacc accgctggta gcggtggttt ttttgtttgc aagcagcaga 1080
ttacgcgcag aaaaaaagga tctcaagaag atcctttgat cttttctacg ggtctgacg 1140 ctcagtggaa cgaaaactca cgttaaggga ttttggtcat ggcgttcgga accgtgctga 1200
cccgcaagtg gcaacctccc gtgcctctgc tcacctttac cgcctggcaa ctggcggcca 1260
cctgcagggc gatcgcaccg agcgcttagt gggaatttgt accccttatc gaaccggag 1320 cacaggatga cgcctaacaa ttcattcaag ccgacaccgc ttcgcggcgc ggcttaattc 1380
aggagttaaa catcatgagg gaagcggtga tcgccgaagt atcgactcaa ctatcagagg 1440
tagttggcgt catcgagcgc catctcgaac cgacgttgct ggccgtacat ttgtacggct 1500
ccgcagtgga tggcggcctg aagccacaca gtgatattga tttgctggtt acggtgaccg 1560
taaggcttga tgaaacaacg cggcgagctt tgatcaacga ccttttggaa acttcggctt 1620
cccctggaga gagcgagatt ctccgcgctg tagaagtcac cattgttgtg cacgacgaca 1680
tcattccgtg gcgttatcca gctaagcgcg aactgcaatt tggagaatgg cagcgcaatg 1740
acattcttgc aggtatcttc gagccagcca cgatcgacat tgatctggct atcttgctga 1800
caaaagcaag agaacatagc gttgccttgg taggtccagc ggcggaggaa ctctttgatc 1860
cggttcctga acaggatcta tttgaggcgc taaatgaaac cttaacgcta tggaactcgc 1920

| | |
|---|---|
| cgcccgactg ggctggcgat gagcgaaatg tagtgcttac gttgtcccgc atttggtaca | 1980 |
| gcgcagtaac cggcaaaatc gcgccgaagg atgtcgctgc cgactgggca atggagcgcc | 2040 |
| tgccggccca gtatcagccc gtcatacttg aagctaggca ggcttatctt ggacaagaag | 2100 |
| atcgcttggc ctcgcgcgca gatcagttgg aagaatttgt tcactacgtg aaaggcgaga | 2160 |
| tcaccaaggt agtcggcaaa taatgtctaa caattcgttc aagccgacgc cgcttcgcgg | 2220 |
| cgcggcttaa ctcaagcgtt a | 2241 |

<210> SEQ ID NO 140
<211> LENGTH: 2195
<212> TYPE: DNA
<213> ORGANISM: Artificial Sequence
<220> FEATURE:
<223> OTHER INFORMATION: universal polynucleotide donor cassette sequence

<400> SEQUENCE: 140

| | |
|---|---|
| gagagctggg gaagactatg cgcgatcgcc tgcagggacc ccgtcgccgt cggcacagcg | 60 |
| tcagggcggt aacatgcgtt ccgttgcgcg tacggaccac cggtgtcgtg taacaggaag | 120 |
| agctgtcagt ggagccacag gttagtagag tggtaggagc agtgttggac tgatggctcg | 180 |
| cttacataag cagttctgtc ccatggagcc aatgtcctga tacggtagga cacatatccc | 240 |
| ttaatgaatc ggccaacgcg cggggagagg cggtttgcgt attgggcgct cttccgcttc | 300 |
| ctcgctcact gactcgctgc gctcggtcgt tcggctgcgg cgagcggtat cagctcactc | 360 |
| aaaggcggta atacggttat ccacagaatc aggggataac gcaggaaaga acatgtgagc | 420 |
| aaaaggccag caaaaggcca ggaaccgtaa aaaggccgcg ttgctggcgt ttttccatag | 480 |
| gctccgcccc cctgacgagc atcacaaaaa tcgacgctca agtcagaggt ggcgaaaccc | 540 |
| gacaggacta taaagatacc aggcgtttcc ccctggaagc tccctcgtgc gctctcctgt | 600 |
| tccgaccctg ccgcttaccg gatacctgtc gcctttctc ccttcgggaa gcgtggcgct | 660 |
| ttctcatagc tcacgctgta ggtatctcag ttcggtgtag tcgttcgct ccaagctggg | 720 |
| ctgtgtgcac gaaccccccg ttcagcccga ccgctgcgcc ttatccggta actatcgtct | 780 |
| tgagtccaac ccggtaagac acgacttatc gccactggca gcagccactg gtaacaggat | 840 |
| tagcagagcg aggtatgtag gcggtgctac agagttcttg aagtggtggc ctaactacgg | 900 |
| ctacactaga agaacagtat ttggtatctg cgctctgctg aagccagtta ccttcggaaa | 960 |
| aagagttggt agctcttgat ccggcaaaca aaccaccgct ggtagcggtg ttttttttgt | 1020 |
| ttgcaagcag cagattacgc gcagaaaaaa aggatctcaa gaagatcctt tgatcttttc | 1080 |
| tacgggtct gacgctcagt ggaacgaaaa ctcacgttaa gggattttgg tcatggcgtt | 1140 |
| cggaaccgtg ctgacccgca gtggcaacc tcccgtgcct ctgctcacct ttaccgcctg | 1200 |
| gcaactggcg gccacctgca gggcgatcgc accgagcgct tagtgggaat ttgtacccct | 1260 |
| tatcgaaccg ggagcacagg atgacgccta acaattcatt caagccgaca ccgcttcgcg | 1320 |
| gcgcggctta attcaggagt taaacatcat gagggaagcg gtgatcgccg aagtatcgac | 1380 |
| tcaactatca gaggtagttg gcgtcatcga gcgccatctc gaaccgacgt tgctggccgt | 1440 |
| acatttgtac ggctccgcag tggatggcgg cctgaagcca cacagtgata ttgatttgct | 1500 |
| ggttacggtg accgtaaggc ttgatgaaac aacgcggcga gctttgatca cgaccttttt | 1560 |
| ggaaacttcg gcttccctg gagagagcga gattctccgc gctgtagaag tcaccattgt | 1620 |
| tgtgcacgac gacatcattc cgtggcgtta tccagctaag cgcgaactgc aatttggaga | 1680 |

| | |
|---|---|
| atggcagcgc aatgacattc ttgcaggtat cttcgagcca gccacgatcg acattgatct | 1740 |
| ggctatcttg ctgacaaaag caagagaaca tagcgttgcc ttggtaggtc cagcggcgga | 1800 |
| ggaactcttt gatccggttc ctgaacagga tctatttgag gcgctaaatg aaaccttaac | 1860 |
| gctatggaac tcgccgcccg actgggctgg cgatgagcga aatgtagtgc ttacgttgtc | 1920 |
| ccgcatttgg tacagcgcag taaccggcaa aatcgcgccg aaggatgtcg ctgccgactg | 1980 |
| ggcaatggag cgcctgccgg cccagtatca gcccgtcata cttgaagcta ggcaggctta | 2040 |
| tcttggacaa gaagatcgct tggcctcgcg cgcagatcag ttggaagaat tgttcacta | 2100 |
| cgtgaaaggc gagatcacca aggtagtcgg caaataatgt ctaacaattc gttcaagccg | 2160 |
| acgccgcttc gcggcgcggc ttaactcaag cgtta | 2195 |

<210> SEQ ID NO 141
<211> LENGTH: 2222
<212> TYPE: DNA
<213> ORGANISM: Artificial Sequence
<220> FEATURE:
<223> OTHER INFORMATION: universal polynucleotide donor cassette sequence

<400> SEQUENCE: 141

| | |
|---|---|
| gagagctggg gaagactatg cgcgatcgcc tgcaggctcg tcgctgatca ccagtatcta | 60 |
| ctcgtacagt actccatgga tgcgtacgcg cccgggaact cctcggcgtc gtccgggctg | 120 |
| accgacatgg cacgcgcatc gaggatgtag atgcacgtga gccacaggtt agtagagtgg | 180 |
| taggagcagt gttggactga tggctcgctt acataagcag ttctgtccca tggagccaat | 240 |
| gtcctgatac ggtaggacac atatccctta atgaatcggc caacgcgcgg ggagaggcgg | 300 |
| tttgcgtatt gggcgctctt ccgcttcctc gctcactgac tcgctgcgct cggtcgttcg | 360 |
| gctgcggcga gcggtatcag ctcactcaaa ggcggtaata cggttatcca cagaatcagg | 420 |
| ggataacgca ggaaagaaca tgtgagcaaa aggccagcaa aaggccagga accgtaaaaa | 480 |
| ggccgcgttg ctggcgtttt tccataggct ccgcccccct gacgagcatc acaaaaatcg | 540 |
| acgctcaagt cagaggtggc gaaacccgac aggactataa agataccagg cgtttccccc | 600 |
| tggaagctcc ctcgtgcgct ctcctgttcc gaccctgccg cttaccggat acctgtccgc | 660 |
| ctttctccct tcgggaagcg tggcgctttc tcatagctca cgctgtaggt atctcagttc | 720 |
| ggtgtaggtc gttcgctcca agctgggctg tgtgcacgaa ccccccgttc agcccgaccg | 780 |
| ctgcgcctta tccggtaact atcgtcttga gtccaacccg gtaagacacg acttatcgcc | 840 |
| actggcagca gccactggta acaggattag cagagcgagg tatgtaggcg gtgctacaga | 900 |
| gttcttgaag tggtggccta actacggcta cactagaaga acagtatttg gtatctgcgc | 960 |
| tctgctgaag ccagttacct tcggaaaaag agttggtagc tcttgatccg gcaaacaaac | 1020 |
| caccgctggt agcggtggtt ttttgtttg caagcagcag attacgcgca gaaaaaagg | 1080 |
| atctcaagaa gatcctttga tcttttctac ggggtctgac gctcagtgga acgaaaactc | 1140 |
| acgttaaggg attttggtca tggcgttcgg aaccgtgctg accgcaagt ggcaacctcc | 1200 |
| cgtgcctctg ctcacctttta ccgcctggca actggcggcc acctgcaggg cgatcgcacc | 1260 |
| gagcgcttag tgggaatttg tacccttat cgaaccggga gcacaggatg acgcctaaca | 1320 |
| attcattcaa gccgacaccg cttcgcggcg cggcttaatt caggagttaa acatcatgag | 1380 |
| ggaagcggtg atcgccgaag tatcgactca actatcagag gtagtggcg tcatcgagcg | 1440 |
| ccatctcgaa ccgacgttgc tggccgtaca tttgtacggc tccgcagtgg atggcggcct | 1500 |

```
gaagccacac agtgatattg atttgctggt tacggtgacc gtaaggcttg atgaaacaac    1560
gcggcgagct tgatcaacg acctttgga aacttcggct tccctggag agagcgagat      1620 tctccgcgct gtagaagtca ccattgttgt gcacgacgac atcattccgt ggcgttatcc   1680
agctaagcgc gaactgcaat ttggagaatg gcagcgcaat gacattcttg caggtatctt   1740
cgagccagcc acgatcgaca ttgatctggc tatcttgctg acaaaagcaa gagaacatag   1800
cgttgccttg gtaggtccag cggcggagga actctttgat ccggttcctg aacaggatct   1860
atttgaggcg ctaaatgaaa ccttaacgct atggaactcg ccgcccgact gggctggcga   1920
tgagcgaaat gtagtgctta cgttgtcccg catttggtac agcgcagtaa ccggcaaaat   1980
cgcgccgaag gatgtcgctg ccgactgggc aatggagcgc ctgccggccc agtatcagcc   2040
cgtcatactt gaagctaggc aggcttatct tggacaagaa gatcgcttgg cctcgcgcgc   2100
agatcagttg gaagaatttg ttcactacgt gaaaggcgag atcaccaagg tagtcggcaa   2160
ataatgtcta acaattcgtt caagccgacg ccgcttcgcg gcgcggctta actcaagcgt   2220
ta                                                                  2222

<210> SEQ ID NO 142
<211> LENGTH: 110
<212> TYPE: DNA
<213> ORGANISM: Artificial Sequence
<220> FEATURE:
<223> OTHER INFORMATION: Analytical Domain

<400> SEQUENCE: 142
gagccacagg ttagtagagt ggtaggagca gtgttggact gatggctcgc ttacataagc    60
agttctgtcc catggagcca atgtcctgat acggtaggac acatatccct               110

<210> SEQ ID NO 143
<211> LENGTH: 118
<212> TYPE: DNA
<213> ORGANISM: Artificial Sequence
<220> FEATURE:
<223> OTHER INFORMATION: Analytical Domain

<400> SEQUENCE: 143
actagttttc atagggatat gtgaggacta accttggcca aaggagctgg aactgcctgc    60
agttatgtaa gggccttagt ccaaattgct ccaccctctg ggaagctaat ggactagt      118

<210> SEQ ID NO 144
<211> LENGTH: 21
<212> TYPE: DNA
<213> ORGANISM: Artificial Sequence
<220> FEATURE:
<223> OTHER INFORMATION: Primer

<400> SEQUENCE: 144
cgccacaaat ctgaaccagc a                                              21

<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145
ccacgatcga cattgatctg gcta                                           24
```

```
<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
gcgacatatc aggccaacag g                                          21

<210> SEQ ID NO 147
<211> LENGTH: 25
<212> TYPE: DNA
<213> ORGANISM: Artificial Sequence
<220> FEATURE:
<223> OTHER INFORMATION: Primer

<400> SEQUENCE: 147
gggatatgtg tcctaccgta tcagg                                      25

<210> SEQ ID NO 148
<211> LENGTH: 21
<212> TYPE: DNA
<213> ORGANISM: Artificial Sequence
<220> FEATURE:
<223> OTHER INFORMATION: Primer

<400> SEQUENCE: 148
ccagcataca gttagggccc a                                          21

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
gttgccttgg taggtccagc                                            20

<210> SEQ ID NO 150
<211> LENGTH: 21
<212> TYPE: DNA
<213> ORGANISM: Artificial Sequence
<220> FEATURE:
<223> OTHER INFORMATION: Primer

<400> SEQUENCE: 150
cgaaaactca gcatgcggga a                                          21

<210> SEQ ID NO 151
<211> LENGTH: 21
<212> TYPE: DNA
<213> ORGANISM: Artificial Sequence
<220> FEATURE:
<223> OTHER INFORMATION: Primer

<400> SEQUENCE: 151
gagccatcag tccaacactg c                                          21

<210> SEQ ID NO 152
<211> LENGTH: 20
<212> TYPE: DNA
<213> ORGANISM: Artificial Sequence
<220> FEATURE:
<223> OTHER INFORMATION: Primer
```

<400> SEQUENCE: 152
acaggcgtac agcaacacca                                                    20

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
gaccctatgg tgttggatcc ca                                                 22

<210> SEQ ID NO 154
<211> LENGTH: 21
<212> TYPE: DNA
<213> ORGANISM: Artificial Sequence
<220> FEATURE:
<223> OTHER INFORMATION: Primer

<400> SEQUENCE: 154
cgggagctag gcaacaaatc g                                                  21

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
tctgactaaa cgggtggatg ctg                                                23

<210> SEQ ID NO 156
<211> LENGTH: 26
<212> TYPE: DNA
<213> ORGANISM: Artificial Sequence
<220> FEATURE:
<223> OTHER INFORMATION: Primer

<400> SEQUENCE: 156
cggatcagtt gattcgctca ctttca                                             26

<210> SEQ ID NO 157
<211> LENGTH: 21
<212> TYPE: DNA
<213> ORGANISM: Artificial Sequence
<220> FEATURE:
<223> OTHER INFORMATION: Primer

<400> SEQUENCE: 157
gccgaaaagc agcaactgga a                                                  21

<210> SEQ ID NO 158
<211> LENGTH: 21
<212> TYPE: DNA
<213> ORGANISM: Artificial Sequence
<220> FEATURE:
<223> OTHER INFORMATION: Primer

<400> SEQUENCE: 158
gattgctacg cagaccgcct a                                                  21

<210> SEQ ID NO 159
<211> LENGTH: 21

<212> TYPE: DNA
<213> ORGANISM: Artificial Sequence
<220> FEATURE:
<223> OTHER INFORMATION: Primer

<400> SEQUENCE: 159
cactattcct ccggcatgca g                                    21

<210> SEQ ID NO 160
<211> LENGTH: 22
<212> TYPE: DNA
<213> ORGANISM: Artificial Sequence
<220> FEATURE:
<223> OTHER INFORMATION: Primer

<400> SEQUENCE: 160
tgacctattg atcggtcggc tc                                   22

<210> SEQ ID NO 161
<211> LENGTH: 22
<212> TYPE: DNA
<213> ORGANISM: Artificial Sequence
<220> FEATURE:
<223> OTHER INFORMATION: Primer

<400> SEQUENCE: 161
tgccttgaat ctcagggatg ca                                   22

<210> SEQ ID NO 162
<211> LENGTH: 21
<212> TYPE: DNA
<213> ORGANISM: Artificial Sequence
<220> FEATURE:
<223> OTHER INFORMATION: Primer

<400> SEQUENCE: 162
gccgaagcta actagcggac a                                    21

<210> SEQ ID NO 163
<211> LENGTH: 21
<212> TYPE: DNA
<213> ORGANISM: Artificial Sequence
<220> FEATURE:
<223> OTHER INFORMATION: Primer

<400> SEQUENCE: 163
catggagtag cagctgtgct g                                    21

<210> SEQ ID NO 164
<211> LENGTH: 21
<212> TYPE: DNA
<213> ORGANISM: Artificial Sequence
<220> FEATURE:
<223> OTHER INFORMATION: Primer

<400> SEQUENCE: 164
gaaaagcagt caccggctct g                                    21

<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
ccatggacat gaattcggca cg                                              22

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
cttttgcacc acggagcaga c                                               21

<210> SEQ ID NO 167
<211> LENGTH: 25
<212> TYPE: DNA
<213> ORGANISM: Artificial Sequence
<220> FEATURE:
<223> OTHER INFORMATION: Primer

<400> SEQUENCE: 167
gctagcaaaa ctttgaagct cgctc                                           25

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
gaggtccctt acgggtcatc g                                               21

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
accaggtcta tcttgcgcag ac                                              22

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
aatagcgtgg tcgggtccta g                                               21

<210> SEQ ID NO 171
<211> LENGTH: 21
<212> TYPE: DNA
<213> ORGANISM: Artificial Sequence
<220> FEATURE:
<223> OTHER INFORMATION: Primer

<400> SEQUENCE: 171
acgaacgatc caaggtgcag t                                               21

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
tagagacgag gactctgggc t                                              21

<210> SEQ ID NO 173
<211> LENGTH: 21
<212> TYPE: DNA
<213> ORGANISM: Artificial Sequence
<220> FEATURE:
<223> OTHER INFORMATION: Primer

<400> SEQUENCE: 173
aagtccaaca tgggcacaac c                                              21

<210> SEQ ID NO 174
<211> LENGTH: 21
<212> TYPE: DNA
<213> ORGANISM: Artificial Sequence
<220> FEATURE:
<223> OTHER INFORMATION: Primer

<400> SEQUENCE: 174
cctcgttaag ggtgcaggtt g                                              21

<210> SEQ ID NO 175
<211> LENGTH: 26
<212> TYPE: DNA
<213> ORGANISM: Artificial Sequence
<220> FEATURE:
<223> OTHER INFORMATION: Primer

<400> SEQUENCE: 175
ccaagtcagc ttctaagcca tcaaac                                         26

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
aaccctagac ttctgcctgg tg                                             22

<210> SEQ ID NO 177
<211> LENGTH: 22
<212> TYPE: DNA
<213> ORGANISM: Artificial Sequence
<220> FEATURE:
<223> OTHER INFORMATION: Primer

<400> SEQUENCE: 177
gctcacttac gagcagatcc ca                                             22

<210> SEQ ID NO 178
<211> LENGTH: 21
<212> TYPE: DNA
<213> ORGANISM: Artificial Sequence
<220> FEATURE:
<223> OTHER INFORMATION: Primer

<400> SEQUENCE: 178
ggtgcacgca tgttctcatg t                                              21

<210> SEQ ID NO 179
<211> LENGTH: 21
<212> TYPE: DNA
<213> ORGANISM: Artificial Sequence
<220> FEATURE:
<223> OTHER INFORMATION: Primer

<400> SEQUENCE: 179
tgtttaccgc agccatgctt g                                          21

<210> SEQ ID NO 180
<211> LENGTH: 23
<212> TYPE: DNA
<213> ORGANISM: Artificial Sequence
<220> FEATURE:
<223> OTHER INFORMATION: Primer

<400> SEQUENCE: 180
gttgtatacg gcatccatcc gct                                        23

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
gaatgaaact ggtggtctgc tcc                                        23

<210> SEQ ID NO 182
<211> LENGTH: 22
<212> TYPE: DNA
<213> ORGANISM: Artificial Sequence
<220> FEATURE:
<223> OTHER INFORMATION: Primer

<400> SEQUENCE: 182
ccgacgaggt acaagtagca gg                                         22

<210> SEQ ID NO 183
<211> LENGTH: 23
<212> TYPE: DNA
<213> ORGANISM: Artificial Sequence
<220> FEATURE:
<223> OTHER INFORMATION: Primer

<400> SEQUENCE: 183
cccgtagtcc agattcttgt ggt                                        23

<210> SEQ ID NO 184
<211> LENGTH: 21
<212> TYPE: DNA
<213> ORGANISM: Artificial Sequence
<220> FEATURE:
<223> OTHER INFORMATION: Primer

<400> SEQUENCE: 184
gtcgtttgtt cggaagggga g                                          21

<210> SEQ ID NO 185
<211> LENGTH: 21
<212> TYPE: DNA
<213> ORGANISM: Artificial Sequence
<220> FEATURE:
<223> OTHER INFORMATION: Primer

<400> SEQUENCE: 185
cgtagttgtc cggcatgtcc t                                                  21

<210> SEQ ID NO 186
<211> LENGTH: 21
<212> TYPE: DNA
<213> ORGANISM: Artificial Sequence
<220> FEATURE:
<223> OTHER INFORMATION: Primer

<400> SEQUENCE: 186
tgtatccctt cggtgagcac g                                                  21

<210> SEQ ID NO 187
<211> LENGTH: 22
<212> TYPE: DNA
<213> ORGANISM: Artificial Sequence
<220> FEATURE:
<223> OTHER INFORMATION: Primer

<400> SEQUENCE: 187
tgaatcgact cgctgacagg tg                                                 22

<210> SEQ ID NO 188
<211> LENGTH: 24
<212> TYPE: DNA
<213> ORGANISM: Artificial Sequence
<220> FEATURE:
<223> OTHER INFORMATION: Primer

<400> SEQUENCE: 188
ccacgatcga cattgatctg gcta                                               24

<210> SEQ ID NO 189
<211> LENGTH: 25
<212> TYPE: DNA
<213> ORGANISM: Artificial Sequence
<220> FEATURE:
<223> OTHER INFORMATION: Primer

<400> SEQUENCE: 189
gggatatgtg tcctaccgta tcagg                                              25

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
gttgccttgg taggtccagc                                                    20

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
gagccatcag tccaacactg c                                                  21

<210> SEQ ID NO 192

```
<211> LENGTH: 20
<212> TYPE: DNA
<213> ORGANISM: Artificial Sequence
<220> FEATURE:
<223> OTHER INFORMATION: Primer

<400> SEQUENCE: 192
tggcactaat ctcaccggct                                            20

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
agtcttagaa gtacgctacc gt                                         22

<210> SEQ ID NO 194
<211> LENGTH: 19
<212> TYPE: DNA
<213> ORGANISM: Artificial Sequence
<220> FEATURE:
<223> OTHER INFORMATION: Primer

<400> SEQUENCE: 194
tacttggctt cggcggcga                                             19

<210> SEQ ID NO 195
<211> LENGTH: 21
<212> TYPE: DNA
<213> ORGANISM: Artificial Sequence
<220> FEATURE:
<223> OTHER INFORMATION: Primer

<400> SEQUENCE: 195
gggtgacttt tacgcgtctc g                                          21

<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196
ggtcacgacg catggcctaa                                            20

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
aggatgcatg gatcaccgtc                                            20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
```
gctctgttgt gcagccgtac                                              20

<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199
cgttgcagat accacagtgt ac                                           22

<210> SEQ ID NO 200
<211> LENGTH: 25
<212> TYPE: DNA
<213> ORGANISM: Artificial Sequence
<220> FEATURE:
<223> OTHER INFORMATION: Primer

<400> SEQUENCE: 200
gctagtagct gtttacacgg cgtct                                        25

<210> SEQ ID NO 201
<211> LENGTH: 22
<212> TYPE: DNA
<213> ORGANISM: Artificial Sequence
<220> FEATURE:
<223> OTHER INFORMATION: Primer

<400> SEQUENCE: 201
aggtcgagac aaccaagtag ag                                           22

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
acaggacatc gagcttgcat                                              20

<210> SEQ ID NO 203
<211> LENGTH: 23
<212> TYPE: DNA
<213> ORGANISM: Artificial Sequence
<220> FEATURE:
<223> OTHER INFORMATION: Primer

<400> SEQUENCE: 203
cagaagaaag gcatcaactc atg                                          23

<210> SEQ ID NO 204
<211> LENGTH: 26
<212> TYPE: DNA
<213> ORGANISM: Artificial Sequence
<220> FEATURE:
<223> OTHER INFORMATION: Primer

<400> SEQUENCE: 204
ctctttcacc tctactttta cttcag                                       26

<210> SEQ ID NO 205
<211> LENGTH: 21
<212> TYPE: DNA

```
<213> ORGANISM: Artificial Sequence
<220> FEATURE:
<223> OTHER INFORMATION: Primer

<400> SEQUENCE: 205
attgaaccgt tgtcaaagcc a                                              21

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
cacagcgtca gggcggtaac                                                20

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
ggcacgcacc tgtcactgac                                                20

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
gtacgcgccc gggaactcct                                                20

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
cctgcggccc acgtgcatct                                                20
```

RAPID ASSAY FOR IDENTIFYING TRANSFORMANTS HAVING TARGETED DONOR INSERTION

CROSS-REFERENCE TO RELATED APPLICATIONS

This application claims the benefit, under 35 U.S.C. §119(e), to U.S. Provisional Patent Application No. 61/873,719, filed Sep. 4, 2013 and U.S. Provisional Patent Application No. 61/899,569, filed Nov. 4, 2013, the contents of which are incorporated by reference in their entirety into the present application.

REFERENCE TO SEQUENCE LISTING SUBMITTED ELECTRONICALLY

The official copy of the sequence listing is submitted electronically via EFS-Web as an ASCII formatted sequence listing with a file named "226007_ST25.txt", created on Nov. 4, 2013, and having a size of 68.6 kilobytes and is filed concurrently with the specification. The sequence listing contained in this ASCII formatted document is part of the specification and is herein incorporated by reference in its entirety.

FIELD OF THE INVENTION

The subject disclosure relates generally to the fields of molecular biology and biochemistry. The subject disclosure concerns a method for analyzing the genomic site of insertion of an integrated donor polynucleotide. The method is applicable for high throughput analysis of the integrated donor polynucleotide and can be used to minimize the detection of false positive results. Furthermore, the method uses cell based targeting and analysis, without the need for production of generating a stably targeted plant.

BACKGROUND OF THE INVENTION

Targeted genome modification of plants has been a long-standing and elusive goal of both applied and basic research. Targeting genes and gene stacks to specific locations in the plant genome will improve the quality of transgenic events, reduce costs associated with production of transgenic events and provide new methods for making transgenic plant products such as sequential gene stacking. Overall, targeting trangenes to specific genomic sites is likely to be commercially beneficial. Significant advances have been made in the last few years towards development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157; 20050064474; and 20060188987, and International Patent Publication No. WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPs genomic locus. Current methods for targeted insertion of exogenous DNA typically involve co-transformation of plant tissue with a donor DNA polynucleotide containing at least one transgene and a site specific nuclease (e.g., ZFN) which is designed to bind and cleave a specific genomic locus. This causes the donor DNA polynucleotide to stably insert within the cleaved genomic locus resulting in targeted gene addition at a specified genomic locus.

Unfortunately, reported and observed frequencies of targeted genomic modification indicate that targeting a genomic loci within plants is relatively inefficient. The reported inefficiency necessitates the screening of a large number of plant events to identify a specific event containing the targeted genomic loci. The screening method should also be applicable as a high throughput method for the rapid identification of plant events containing a targeted genomic loci. In addition, as targeted gene insertion occurs in conjunction with random gene insertion, screening methods must be designed to specifically identify targeting of genomic loci within a background of random insertions and to discern the genomic integration from exogenous plasmid DNA which may produce false-positive results. Furthermore, the assay should be sensitive enough to detect an event occurring in a single cell, wherein that cell contains the only targeted event amongst thousands of other non-targeted cells. Most reported plant event analyses rely on a single analytical method for confirming targeting which may lead to inaccurate estimation of targeting frequencies and low confidence outcomes. A need exists for development of improved molecular assay methods, particularly for high-throughput analysis, that can detect site specific chromosomal integrations and discern these events from exogenous plasmid DNA. Finally, current methods for assessing targeted genomic modifications are based on generation of stable plants and are time and cost intensive. Accordingly, there is a need for an analytical method that allows rapid targeting assessment at a large number of genomic loci and screening of a large number of site-specific nucleases to identify and confirm the insertion of a polynucleotide donor sequence within the targeted genomic loci.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

In an embodiment, the disclosure relates to an assay for detecting site specific integration of a polynucleotide donor sequence within a genomic target site, wherein: a genomic DNA is amplified with a first round of PCR to produce a first amplicon using a first Out-PCR primer designed to bind to the genomic DNA target site; a first In-PCR primer designed to bind the integrated polynucleotide donor sequence, and the first amplicon is amplified with a second round of PCR using primers specific to sequences located within the first amplicon to produce a second amplicon; and, the presence of the second amplicon is detected, wherein the production of the second amplicon indicates the presence of the site specific integration event.

In an aspect of the embodiment, the genomic target site comprises an endogenous or an engineered genomic target site. In another aspect of the embodiment, the first In-PCR primer is provided at a lower concentration than the first Out-PCR primer. In an embodiment, the first round of PCR is conducted using a relative concentration of first Out-PCR primer to first In-PCR primer of about 4:1, 3:1 or 2:1. In another embodiment, the first In-PCR primer comprises a concentration of 0.05-0.09 µM, and the first Out-PCR primer comprises a concentration of at least 0.1 µM.

In a subsequent aspect of the embodiment, the second round of PCR comprises a second Out-PCR primer designed to bind to the genomic DNA target site of the first amplicon and a second In-PCR primer designed to bind the integrated polynucleotide donor sequence of the first amplicon. In an embodiment, the second In-PCR primer is provided at a lower concentration than the second Out-PCR primer. In another embodiment, the second round of PCR is conducted using a relative concentration of second Out-PCR primer to second In-PCR primer of about 4:1, 3:1 or 2:1. In a further embodiment, the second In-PCR primer comprises a concentration of 0.05-0.1 µM, and the second Out-PCR primer comprises a concentration of 0.2 µM.

In a further aspect of the embodiment, the genomic DNA comprising the site specific integration of the polynucleotide donor sequence within the genomic target site is a plant genomic DNA. As an embodiment, the plant genomic DNA is isolated from a monocotyledonous plant. As another embodiment, the plant genomic DNA is isolated from a dicotyledonous plant.

In another aspect of the embodiment, the cleavage of the genomic DNA target site with a site specific nuclease results in the site specific integration of the polynucleotide donor sequence within the genomic target site. As an embodiment, the site specific nuclease is selected from the group consisting of a Zinc Finger nuclease, a CRISPR nuclease, a TALEN nuclease, or a meganuclease. In a subsequent embodiment, the site specific integration of the polynucleotide donor sequence within the genomic target site occurs via a Non Homologous End Joining mechanism.

In an aspect of the embodiment, the detecting step is an agarose gel of the second amplicon or a sequencing reaction of the second amplicon.

In yet another aspect of the embodiment, the disclosure relates to a method for detecting site specific integration of a polynucleotide donor sequence within a genomic target site of transfected plant cells comprising: amplifying a genomic DNA with a first round of PCR to produce a first amplicon, wherein said PCR is conducted using a first Out-PCR primer designed to bind to the genomic target site and a first In-PCR primer designed to bind the polynucleotide donor sequence, further wherein said first In-PCR primer is provided at a lower concentration than the first Out-PCR primer; amplifying the first amplicon with a second round of PCR using primers specific to sequences located within the first amplicon to produce a second amplicon; and, detecting the presence of a second amplicon, wherein the production of a second amplicon indicates the presence of a site specific integration event. In other embodiments, the plant cell is a protoplast plant cell. In an embodiment, the detection of the site specific integration is performed on a mixed population of targeted and non-targeted plant cells, wherein the non-targeted plant cells do not contain a polynucleotide donor sequence within a genomic target site.

In addition to the exemplary aspects and embodiments described above, further aspects and embodiments will become apparent by study of the following descriptions.

BRIEF DESCRIPTION OF THE FIGURES

FIG. 15A represents the data in a bar graph form.
FIG. 15B represents the data as a table.
FIG. 20 illustrates the sequence of In-Out amplified PCR products. Four clones from each In-Out PCR were sequenced and the results demonstrated intact target donor junctions and processed end junctions. The sequences listed correspond with SEQ I NO: 248 as predicted, SEQ ID NO:249 as A9-1, SEQ ID NO:250 as A9-2, SEQ ID NO:251 as A9-5, SEQ ID NO:252 as A9-6, SEQ ID NO:253 as G8-1, SEQ ID NO:254 as G8-2, SEQ ID NO:255 as G8-5, SEQ ID NO:256 as G8-6, SEQ ID NO:257 as G9-1, SEQ ID NO:258 as G9-2, SEQ ID NO:259 as G9-6, SEQ ID NO:260 as H9-1, SEQ ID NO:261 as H9-2, SEQ ID NO:262 as H9-5, and SEQ ID NO:263 as H9-6.

FIG. 25 provides the sequence of In-Out PCR products resulting from NHEJ targeting of a donor sequence using the F2, ZFN2 zinc finger nuclease in the FAD2 2.3 locus. The reference sequence (top of figure) represents the configuration of the targeted insertion of the donor vector in a reverse orientation. The single-stranded ends of the DNAs resulting from FokI digestion were filled in to create the reference sequence. Sanger sequences are shown. The F2, ZFN2 ZFN binding sequences are underlined. Plasmid clones with a similar sequence to the specified sequence are listed to the right.

DETAILED DESCRIPTION

I. Overview

Figure 1:
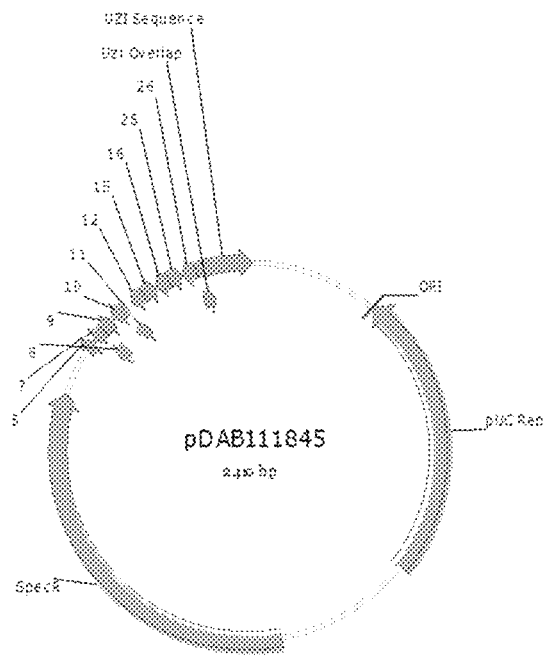
FIG. 1 illustrates a plasmid map of pDAB111845.

Novel methods have now been disclosed for rapid screening, identification and characterization of site specific nuclease targeted plant events. The methods can be used to analyze the integration a donor polynucleotide within a genomic target locus via a first and second amplification reaction. The first and second amplification reactions are an "In-Out" PCR amplification reaction for screening the 3' and/or the 5' junction sequences of a donor DNA polynucleotide targeted within a genomic locus. The presence of an amplified product which contains the 3' and/or 5' junction sequence indicates that the donor DNA polynucleotide is present within the targeted genomic locus.

The disclosed screening assays describe high quality, high throughput processes for identifying and obtaining targeted transgene insertion events. Deployment of the screening assay allows for large numbers of plant events to be analyzed and screened to select specific events which have a donor DNA polynucleotide inserted within a targeted genomic locus, and to discern these events from false-positive results. Moreover, the disclosed methods can be deployed as high throughput assays allowing for the rapid and efficient identification of a subset of samples that can then be further analyzed by other molecular confirmation methods. The presently disclosed subject matter includes plants and plant cells comprising nuclease targeted plant events selected utilizing the novel screening methods. Furthermore, the methodology is readily applicable for the analysis of any plant species.

II. Terms

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises", "comprising", "includes", "including", "has", "having", "contains", or "containing", or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single embodiment of the particular invention but encompasses all possible embodiments as disclosed in the application.

As used herein, the term "plant" includes a whole plant and any descendant, cell, tissue, or part of a plant. The term "plant parts" include any part(s) of a plant, including, for example and without limitation: seed (including mature seed, immature seed, and immature embryo without testa); a plant cutting; a plant cell; a plant cell culture; a plant organ (e.g., pollen, embryos, flowers, fruits, shoots, leaves, roots, stems, and related explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant. Plant cells, as used herein, includes protoplasts and protoplasts with a partial cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein.

The term "protoplast", as used herein, refers to a plant cell that had its cell wall completely or partially removed, with the lipid bilayer membrane thereof naked. Typically, a protoplast is an isolated plant cell without cell walls which has the potency for regeneration into cell culture or a whole plant.

As used herein, "endogenous sequence" defines the native form of a polynucleotide, gene or polypeptide in its natural location in the organism or in the genome of an organism.

The term "isolated" as used herein means having been removed from its natural environment.

The term "purified", as used herein relates to the isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

As used herein, the terms "polynucleotide", "nucleic acid", and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide", and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a hetereologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another gene or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

As used herein, the term "modification" can refer to a change in a polynucleotide disclosed herein that results in reduced, substantially eliminated or eliminated activity of a polypeptide encoded by the polynucleotide, as well as a change in a polypeptide disclosed herein that results in reduced, substantially eliminated or eliminated activity of the polypeptide. Alternatively, the term "modification" can refer to a change in a polynucleotide disclosed herein that results in increased or enhanced activity of a polypeptide encoded by the polynucleotide, as well as a change in a polypeptide disclosed herein that results in increased or enhanced activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof.

The term "derivative", as used herein, refers to a modification of a sequence set forth in the present disclosure. Illustrative of such modifications would be the substitution, insertion, and/or deletion of one or more bases relating to a nucleic acid sequence of a coding sequence disclosed herein that preserve, slightly alter, or increase the function of a coding sequence disclosed herein in crop species. Such derivatives can be readily determined by one skilled in the art, for example, using computer modeling techniques for predicting and optimizing sequence structure. The term "derivative" thus also includes nucleic acid sequences having substantial sequence identity with the disclosed coding sequences herein such that they are able to have the disclosed functionalities for use in producing embodiments of the present disclosure.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise rationally designed DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression", as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic", "recombinant", or "transformed" organisms. Known methods of transformation include, for example: *Agrobacterium tumefaciens*- or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) Breeding Field Crops, 4th Edition, AVI Publication Co., Westport Conn.

Backcrossing methods may be used to introduce a nucleic acid into a plant. This technique has been used for decades to introduce traits into plants. An example of a description of backcrossing (and other plant breeding methodologies) can be found in, for example, Poelman (1995), supra; and Jensen (1988) Plant Breeding Methodology, Wiley, New York, N.Y. In an exemplary backcross protocol, an original plant of interest (the "recurrent parent") is crossed to a second plant (the "non-recurrent parent") that carries the nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion", because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing", in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least one region of homology to the genome ("homology arms") of least 50-100 base pairs in length. See, e.g., U.S. Patent Publication No. 20110281361.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

The terms "plasmid" and "vector", as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may carry DNA derived from essentially any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences for propagating in bacterial hosts.

Polypeptide and "protein" are used interchangeably herein and include a molecular chain of two or more amino acids linked through peptide bonds. The terms do not refer to a specific length of the product. Thus, "peptides", and "oligopeptides", are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

III. Embodiments of the Present Invention

In an embodiment, the disclosure relates to an assay for detecting site specific integration of a polynucleotide donor sequence within a genomic target site.

In some embodiments a genomic DNA is assayed for detecting site specific integration of a polynucleotide donor sequence within a genomic target site. In aspects of the embodiment, the genomic DNA comprises; a chromosomal genomic DNA, a mitochondrial genomic DNA, a transposable element genomic DNA, a genomic DNA derived from a viral integration, an artificial chromosome genomic DNA (see PCT/US2002/017451 and PCT/US2008/056993, included herein as non-limiting examples), and other sources of genomic DNA.

In some embodiments, the genomic DNA is amplified via the Polymerase Chain Reaction (PCR). In aspects of the embodiment, PCR generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

In other embodiments, the PCR reaction produces an amplicon. As an aspect of the embodiment, amplicon refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not necessarily imply the presence of exponentially amplified nucleic acids.

Amplification of a selected, or target, nucleic acid sequence may be carried out by any suitable method. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SW") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

In another embodiment, the amplification of the genomic DNA is completed via a PCR reaction using primers. In an aspect of the embodiment, the primers may comprise a first set of primers, a second set of primers, a third set of primers, and so forth. As such, the designation "first", "second", "third", etc. indicate the order by which the primer sets are used in a nested PCR reaction. For example, the "first" set of primers are used initially in a first PCR reaction to amplify a polynucleotide sequence. Next, the "second" set of primers are used in a second PCR reaction to amplify the product of the first PCR reaction. Then the "third" set of primers are used in a third PCR reaction to amplify the product of the second PCR reaction and so forth. In other aspects of the embodiment, the primers may be an "Out" primer that is designed to bind the genomic DNA target site, or an "In" primer that is designed to bind a polynucleotide donor sequence that is integrated within the genome of an organism. In other embodiments the first set of primers may be comprised of an In and an Out primer, or may be designed to comprise two distinct In primers, or two distinct Out primers. In an embodiment, the term primer refers to an oligonucleotide that is complementary to a DNA template to be amplified in an appropriate amplification buffer. In certain embodiment the primers may be from 10 Bp to 100 Bp, 10 Bp to 50 Bp or 10 Bp to 25 Bp in length.

In an embodiment of the subject disclosure the In primer is provided at a lower concentration than the Out primer. An aspect of the embodiment includes, a relative concentration of Out primer to In primer of about 10:1, 9:1, 8:1, 7:1, 6:1, 5:1, 4:1, 3:1 or 2:1. In another aspect, the embodiment includes where the In primer comprises a concentration of 0.001, 0.005, 0.01, 0.02, 0.03, 0.04, 0.05, 0.06, 0.07. 0.008, or 0.09 μM, and the Out primer comprises a concentration of at least 0.1 μM. In a further aspect, the embodiment includes where the In primer comprises a concentration of 0.01, 0.02, 0.03, 0.04, 0.05, 0.06, 0.07. 0.08, 0.09, 0.1, 0.11 0.12, 0.13, 0.14, 0.15, 0.16, 0.17, 0.18 or 0.19 μM, and the Out primer comprises a concentration of at least 0.2 μM.

In some embodiments, the genomic integration site is a plant genomic DNA. In an aspect plant cells which are transformed in accordance with the present disclosure includes, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, brachiaria, wheat, safflowers, sorghum, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., Nature Biotech 17:282-286 (1999); Mild et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

A large number of techniques are available for inserting DNA into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS mediated transformation, aerosol beaming, or PEG as well as other possible methods.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) Nature 327:70-73). Additional methods for plant cell transformation include microinjection via silicon carbide WHISKERS mediated DNA uptake (Kaeppler et al. (1990) Plant Cell Reporter 9:415-418). Alternatively, the DNA construct can be introduced into the plant cell via nanoparticle transformation (see, e.g., U.S. patent application Ser. No. 12/245,685, which is incorporated herein by reference in its entirety).

Another known method of plant transformation is microprojectile-mediated transformation wherein DNA is carried on the surface of microprojectiles. In this method, the vector is introduced into plant tissues with a biolistic device that accelerates the microprojectiles to speeds sufficient to penetrate plant cell walls and membranes. Sanford et al., Part. Sci. Technol. 5:27 (1987), Sanford, J. C., Trends Biotech. 6:299 (1988), Sanford, J. C., Physiol. Plant 79:206 (1990), Klein et al., Biotechnology 10:268 (1992).

Alternatively, gene transfer and transformation methods include, but are not limited to, protoplast transformation through calcium chloride precipitation, polyethylene glycol (PEG)- or electroporation-mediated uptake of naked DNA (see Paszkowski et al. (1984) EMBO J 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505).

A widely utilized method for introducing an expression vector into plants is based on the natural transformation system of *Agrobacterium*. Horsch et al., Science 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., Crit. Rev. Plant. Sci. 10:1 (1991). Descriptions of *Agrobacterium* vector systems and methods for *Agrobacterium*-mediated gene transfer are also available, for example, Gruber et al., supra, Mild et al., supra, Moloney et al., Plant Cell Reports 8:238 (1989), and U.S. Pat. Nos. 4,940,838 and 5,464,763.

If *Agrobacterium* is used for the transformation, the DNA to be inserted should be cloned into special plasmids, namely either into an intermediate vector or into a binary vector. Intermediate vectors cannot replicate themselves in *Agrobacterium*. The intermediate vector can be transferred into *Agrobacterium tumefaciens* by use of a helper plasmid (conjugation). The Japan Tobacco Superbinary system is an example of such a system (reviewed by Komari et al., (2006) In: Methods in Molecular Biology (K. Wang, ed.) No. 343: *Agrobacterium* Protocols (2nd Edition, Vol. 1) Humana Press Inc., Totowa, N.J., pp. 15-41; and Komori et al., (2007) Plant Physiol. 145:1155-1160). Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters, 1978). The *Agrobacterium* used as host cell is to comprise a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) Nuc. Acid Res. 12:8711-8721) or the non-binary T-DNA vector procedure (Horsch et al. (1985) Science 227:1229-1231). Generally, the *Agrobacterium* transformation system is used to engineer dicotyledonous plants (Bevan et al. (1982) Ann Rev. Genet 16:357-384; Rogers et al. (1986) Methods Enzymol. 118:627-641). The *Agrobacterium* transformation system may also be used to transform, as well as transfer, DNA to monocotyledonous plants and plant cells. See U.S. Pat. No. 5,591,616; Hernalsteen et al. (1984) EMBO J 3:3039-3041; Hooykass-Van Slogteren et al. (1984) Nature 311:763-764; Grimsley et al. (1987) Nature 325:1677-179; Boulton et al. (1989) Plant Mol. Biol. 12:31-40; and Gould et al. (1991) Plant Physiol. 95:426-434. Following the introduction of the genetic construct into particular plant cells, plant cells can be grown and upon emergence of differentiating tissue such as shoots and roots, mature plants can be generated. In some embodiments, a plurality of plants can be generated. Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann Rev. of Plant Phys. 38:467-486.

In other embodiments, the plant cells which are transformed are not capable of regeneration to produce a plant. Such cells are said to be transiently transformed. Transiently transformed cells may be produced to assay the expression and/or functionality of a specific transgene. Transient transformation techniques are known in the art, and comprise minor modifications to the transformation techniques described above. Those with skill in the art may elect to utilize transient transformation to quickly assay the expression and/or functionality of a specific transgenes, as transient transformation are completed quickly and do not require as many resources (e.g., culturing of plants for development of whole plants, self-fertilization or crossing of plants for the fixation of a transgene within the genome, etc.) as stable transformation techniques.

In an embodiment the donor polynucleotide can be introduced into essentially any plant. A wide variety of plants and plant cell systems may be engineered for site specific integration of the donor polynucleotide of the present disclosure and the various transformation methods mentioned above. In an embodiment, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., Arabidopsis).

In other embodiments, the polynucleotide donor sequences are introduced into a plant cell for site specific targeting within a genomic target site. In such embodiments, the plant cell may be a protoplast plant cell. The protoplasts can be produced from various types of plant cells. Accordingly, those having ordinary skill in the art may utilize different techniques or methodologies to produce the protoplast plant cell. For example, the generation and production of protoplasts are provided by: Green and Phillips, Crop Sci., 15 (1975) 417-421; Harms et al. Z. Pflanzenzuechtg., 77 (1976) 347-351; European patent applications EP-0,160, 390, Lowe and Smith (1985); EP-0,176,162, Cheng (1985); and EP-0,177,738, Close (1985); Cell Genetics in Higher Plants, Dudits et al., (eds), Akademiai Kiado, Budapest (1976) 129-140, and references therein; Harms, "Maize and Cereal Protoplasts-Facts and Perspectives," Maize for Biological Research, W. F. Sheridan, ed. (1982); Dale, in: Protoplasts (1983); Potrykus et al (eds.) Lecture Proceedings, Experientia Supplementum 46, Potrykus et al., eds, Birkhauser, Basel (1983) 31-41, and references therein. Plant regeneration from cultured protoplasts is described in Evans et al. (1983) "Protoplast Isolation and Culture." Handbook of Plant Cell Cultures 1, 124-176 (MacMillan Publishing Co., New York; Davey (1983) "Recent Developments in the Culture and Regeneration of Plant Protoplasts," Protoplasts, pp. 12-29, (Birkhauser, Basel); Dale (1983) "Protoplast Culture and Plant Regeneration of Cereals and Other Recalcitrant Crops," Protoplasts pp. 3 41, (Birkhauser, Basel); Binding (1985) "Regeneration of Plants," Plant Protoplasts, pp. 2.1-73, (CRC Press, Boca Raton, Fla.).

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In subsequent embodiments, the DNA binding domain comprising one or more DNA binding sequences is bound by a zinc finger binding protein, a meganuclease binding protein, a CRIPSR, or a TALEN binding protein.

In certain embodiments, the composition and methods described herein employ a meganuclease (homing endonuclease) binding protein or meganuclease DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain).

In other embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from Xanthomonas campestgris pv. Vesicatoria (see Bonas et al (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication Nos. 20110239315, 20110145940 and 20110301073, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) Science 326:1501 and Boch et al (2009) Science 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Patent Publication No. 20110301073; Christian et al ((2010)<Genetics epub 10.1534/genetics. 110.120717).

In other embodiments, the nuclease is a system comprising the CRISPR (Clustered Regularly Interspaced Short Palindromic Repeats)/Cas (CRISPR Associated) nuclease system. The CRISPR/Cas is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA next to a photospacer adjacent motif (PAM) NGG. Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence adjacent to a PAM (see Jinek et al (2012) Science 337, p. 816-821, Jinek et al, (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534, 261; 6,599,692; 6,503,717; 6,689,558; 7,030,215; 6,794, 136; 7,067,317; 7,262,054; 7,070,934; 7,361,635; 7,253, 273; and U.S. Patent Publication Nos. 2005/0064474; 2007/ 0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of five or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) Proc Natl Acad Sci USA 93(3):1156-1160. More recently, ZFNs have been used for genome modification in a variety of organisms. See, for example, United States Patent Publications 20030232410; 20050208489; 20050026157; 20050064474; 20060188987;

20060063231; and International Publication WO 07/014275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from particular endonuclease or exonuclease. Exemplary endonucleases from which a cleavage domain can be derived include, but are not limited to, certain restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of DNA sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In an embodiment the polynucleotide donor cassette comprises a sequence that encodes a peptide. To express a peptide, nucleotide sequences encoding the peptide sequence are typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989; 3rd ed., 2001); Kriegler, Gene Transfer and Expression: A Laboratory Manual (1990); and Current Protocols in Molecular Biology (Ausubel et al., supra.). Bacterial expression systems for expressing a peptide are available in, e.g., E. coli, Bacillus sp., and Salmonella (Palva et al., Gene 22:229-235 (1983)). Kits for such expression systems are commercially available. Eukaryotic expression systems for mammalian cells, yeast, and insect cells are well known by those of skill in the art and are also commercially available.

In an embodiment the polynucleotide donor cassette comprises a gene expression cassette comprising a transgene. The gene expression cassette typically contains a transcription unit or expression cassette that contains all the additional elements required for the expression of the nucleic acid in host cells, either prokaryotic or eukaryotic. A typical gene expression cassette thus contains a promoter operably linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

In an embodiment the gene expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp7831-7846(nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

In other embodiments, the gene expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154: 9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987). The construct can also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In an embodiment the gene expression cassette of the polynucleotide donor sequence comprises a promoter. The promoter used to direct expression of a peptide encoding nucleic acid depends on the particular application. For example, a strong constitutive promoter suited to the host cell is typically used for expression and purification of proteins. Non-limiting examples of preferred plant promoters include promoter sequences derived from *A. thaliana* ubiquitin-10 (ubi-10) (Callis, et al., 1990, J. Biol. Chem., 265:12486-12493); *A. tumefaciens* mannopine synthase (Amas) (Petolino et al., U.S. Pat. No. 6,730,824); and/or Cassava Vein Mosaic Virus (CsVMV) (Verdaguer et al., 1996, Plant Molecular Biology 31:1129-1139).

In methods disclosed herein, a number of promoters that direct expression of a gene in a plant can be employed. Such promoters can be selected from constitutive, chemically-regulated, inducible, tissue-specific, and seed-preferred promoters.

Constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in embodiments of the instant disclosure. See Ward et al. Plant Mol. Biol. 22: 361-366 (1993). Exemplary inducible promoters include ecdysone receptor promoters (U.S. Pat. No. 6,504,082); promoters from the ACEI system which respond to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); or promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-la Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as PSCS (Zang et al. (1997) Plant Sciences 129:81-89); cold-inducible promoters, such as, cor15a (Hajela et al. (1990) Plant Physiol. 93:1246-1252), cor15b (Wilhelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as Trg-31 (Chaudhary et al (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pMAS promoter (Guevara-Garcia et al. (1993) Plant J. 4(3):495-505) and the *Agrobacterium* ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al. 1989. The Plant Cell Vol. 1, 839-853), and the maize globulin-1 gene, Belanger, et al. 1991 Genetics 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. Plant J. 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from corn (Belenger and Kriz. 1991. Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase)-2 Gene Capable of Conferring Tissue-Specific Gene Expression in Transgenic Maize. Plant Science 163: 865-872).

A gene expression cassette may contain a 5' leader sequence. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The construct may also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (see Lebrun et al. U.S. Pat. No. 5,510,417), *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (see, U.S. Pat. No. 5,510, 471). Additional chloroplast transit peptides have been described previously in U.S. Pat. Nos. 5,717,084; 5,728,925. One skilled in the art will readily appreciate the many options available in expressing a product to a particular organelle. For example, the barley alpha amylase sequence is often used to direct expression to the endoplasmic reticulum. Rogers, J. Biol. Chem. 260:3731-3738 (1985).

In an embodiment the polynucleotide donor cassette comprises a transgene. Some embodiments herein provide a transgene encoding a polypeptide comprising a gene expression cassette. Such a transgene may be useful in any of a wide variety of applications to produce transgenic plants. Particular examples of a transgene comprising a gene expression cassette are provided for illustrative purposes herein and include a gene expression comprising a trait gene, an RNAi gene, or a reporter/selectable marker gene.

In engineering a gene for expression in plants, the codon bias of the prospective host plant(s) may be determined, for example, through use of publicly available DNA sequence databases to find information about the codon distribution of plant genomes or the protein coding regions of various plant genes. Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

In an embodiment, a transgene to be expressed is disclosed in the subject application. The gene expression cassette may comprise a reporter/selectable marker gene, a trait gene, or an RNAi gene. Examples of a selectable marker gene, a trait gene, and an RNAi gene are further provided below. The methods disclosed in the present application are advantageous in that they provide a method for selecting germline transformants that is not dependent on the specific function of the protein product, or other function, of the transgene.

Transgenes or Coding Sequence that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., 1988 EMBO J. 7:1241), which is also known as AHAS enzyme (Mild et al., 1990 Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

Genes that Confer or Contribute to a Value-Added Trait (A) Modified fatty acid metabolism, for example, by transforming maize or Brassica with an antisense gene or stearoyl-ACP desaturase to increase stearic acid content of the plant (Knultzon et al., 1992) Proc. Nat. Acad. Sci. USA 89:2624.

(B) Decreased phytate content (1) Introduction of a phytase-encoding gene, such as the Aspergillus niger phytase gene (Van Hartingsveldt et al., 1993 Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, Streptococcus mucus fructosyltransferase gene (Shiroza et al., 1988) J. Bacteriol. 170:810, Bacillus subtilis levansucrase gene (Steinmetz et al., 1985 Mol. Gen. Genet. 200:220), Bacillus licheniformis α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

In a subsequent embodiment, the transgene comprises a reporter gene. In various embodiments the reporter gene is selected from the group consisting of a yfp gene, a gus gene, a rfp gene, a gfp gene, a kanamycin resistance gene, an aad-1 gene, an aad-12 gene, a pat gene, and a glyphosate tolerant gene. Reporter or marker genes for selection of transformed cells or tissues or plant parts or plants may be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, 1983; Meijer et al., Plant Mol. Biol. 16:807-820, 1991); neomycin phosphotransferase, which confers resistance to the aminoglycosides neomycin, kanamycin and paromycin (Herrera-Estrella, EMBO J. 2:987-995, 1983 and Fraley et al. Proc. Natl. Acad. Sci USA 80:4803 (1983)); hygromycin phosphotransferase, which confers resistance to hygromycin (Marsh, Gene 32:481-485, 1984; see also Waldron et al., Plant Mol. Biol. 5:103-108, 1985; Zhijian et al., Plant Science 108:219-227, 1995); trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from Aspergillus terreus, which confers resistance to Blasticidin S (Tamura, Biosci. Biotechnol. Biochem. 59:2336-2338, 1995).

Additional selectable markers include, for example, a mutant acetolactate synthase, which confers imidazolinone or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, 1983); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990); sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); phosphinothricin (DeBlock et al., EMBO J. 6:2513-2518, 1987), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al, Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al, Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PHI-YFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al. (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

The term "percent identity" (or "% identity"), as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) Computational Molecular Biology (Lesk, A. M., Ed.) Oxford University: NY (1988); 2.) Biocomputing: Informatics and Genome Projects (Smith, D. W., Ed.) Academic: NY (1993); 3.) Computer Analysis of Sequence Data, Part I (Griffin, A. M., and Griffin, H. G., Eds.) Humania: NJ (1994); 4.) Sequence Analysis in Molecular Biology (von Heinje, G., Ed.) Academic (1987); and 5.) Sequence Analysis Primer (Gribskov, M. and Devereux, J., Eds.) Stockton: NY (1991).

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. See, Russell, R., and Barton, G., "Structural Features can be Unconserved in Proteins with Similar Folds," J. Mol. Biol. 244, 332-350 (1994), at p. 337, which is incorporated herein by reference in its entirety.

In addition, methods to determine identity and similarity are codified in publicly available computer programs Sequence alignments and percent identity calculations can be performed, for example, using the AlignX program of the Vector NTI® suite (Invitrogen, Carlsbad, Calif.) or MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, CABIOS. 5:151-153 (1989); Higgins, D. G. et al., Comput. Appl. Biosci., 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS. 5:151-153 (1989); Higgins, D. G. et al., Comput. Appl. Biosci. 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing embodiments of the present disclosure, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, plasmid DNA fragments, cDNA fragments, RNA fragments, PCR amplified DNA fragments, oligonucleotides, or other polynucleotides, and may be labeled with a detectable group such as $^{32}$P, or any other detectable marker. Thus, for example, probes for hybridization can be made by labeling synthetic oligonucleotides based on the DNA sequences of embodiments of the disclosure. Methods for preparation of probes for hybridization and for construction of cDNA and genomic libraries are generally known in the art and are disclosed (Sambrook et al., 1989).

The nucleic acid probes and primers of embodiments of the present disclosure hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if the two nucleic acid molecules exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 0.1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

Specificity is typically a function of post-hybridization washes, the critical factors being the ionic strength and temperature of the final wash solution. For DNA-DNA hybrids, the $T_m$ can be approximated from the equation $T_m$=81.5° C.+16.6 (log M)+0.41(% GC)-0.61(% form.)-500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al, *Short Protocols in Molecular Biology*, pages 2-40, Third Edit. (1997) and Sambrook et al. (1989).

In another embodiment of the present disclosure, a method for targeted integration of the polynucleotide donor cassette within the genome of a plant cell is disclosed. In certain embodiments, a site specific DNA binding nuclease comprising at least one DNA-binding domain and at least one nuclease domain, wherein the at least one DNA-binding domain binds to a target site within the genome of the plant cell is expressed. In other embodiments the plant cell is contacted with the polynucleotide donor cassette. In further embodiments the target site within the genome of the plant cell is cleaved with the site specific DNA binding nuclease. In yet another embodiment the polynucleotide donor cassette is integrated into the target site within the genome of the plant cell.

In an embodiment the targeted integration of the polynucleotide donor cassette within the genome of a plant cell via a homology directed repair mechanism is disclosed. In another embodiment the targeted integration of the polynucleotide donor cassette within the genome of a plant cell via a non-homologous end joining directed repair mechanism is disclosed.

The donor molecules disclosed herein are integrated into a genome of a cell via targeted, homology-independent methods. For such targeted integration, the genome is cleaved at a desired location (or locations) using a nuclease, for example, a fusion between a DNA-binding domain (e.g., zinc finger binding domain or TAL effector domain is engineered to bind a target site at or near the predetermined cleavage site) and nuclease domain (e.g., cleavage domain or cleavage half-domain). In certain embodiments, two fusion proteins, each comprising a DNA-binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two DNA-binding domains. One or both of the DNA-binding domains can be engineered. See, also, U.S. Pat. No. 7,888,121; U.S. Patent Publication 20050064474 and International Patent Publications WO05/084190, WO05/014791 and WO 03/080809.

The nucleases as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues of DNA and/or RNA.

Following the introduction of a double-stranded break in the region of interest, the transgene is integrated into the region of interest in a targeted manner via non-homology dependent methods (e.g., non-homologous end joining (NHEJ)) following linearization of a double-stranded donor molecule as described herein. The double-stranded donor is preferably linearized in vivo with a nuclease, for example one or more of the same or different nucleases that are used to introduce the double-stranded break in the genome. Synchronized cleavage of the chromosome and the donor in the cell may limit donor DNA degradation (as compared to linearization of the donor molecule prior to introduction into the cell). The nuclease target sites used for linearization of the donor preferably do not disrupt the transgene(s) sequence(s).

The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in deletion of several nucleotides.

IV. Assays for Detection of Site Specific Integration of a Donor Polynucleotide

In an embodiment, the amplification reaction is quantified. In other embodiments, the amplification reaction is detected. In various embodiments the detecting may include visualization on an agarose or acrylamide gel, sequencing of an amplicon, or using a signature profile, in which the signature profile is selected from the group consisting of a melting temperature or a fluorescence signature profile.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' or 3' end) of the exemplified primers fall within the scope of the subject disclosure. Mutations, insertions, and deletions can be produced in a given primer by methods known to an ordinarily skilled artisan.

Another example of detection is the pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal that is measured. A light signal indicates the presence of the transgene insert/flanking sequence due to successful amplification, hybridization, and single or multi-base extension. (This technique is used for initial sequencing, not for detection of a specific gene when it is known.)

Molecular Beacons have been described for use in detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

KASPar assays are a method of detecting and quantifying the presence of a DNA sequence. Briefly, the genomic DNA sample comprising the targeted genomic locus is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the donor DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the donor DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 μM, less than 4 μM, or less than 2.7 μM.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Design of Zinc Fingers to Bind Genomic Loci in Zea mays

Zinc finger proteins directed against identified DNA sequences of the targetable Zea mays genomic loci were designed as previously described. See, e.g., Urnov et al., (2005) Nature 435:646-551. Exemplary target sequence and recognition helices are shown in Table 1 (recognition helix regions designs) and Table 2 (target sites). In Table 2, nucleotides in the target site that are contacted by the ZFP recognition helices are indicated in uppercase letters and non-contacted nucleotides are indicated in lowercase. Zinc Finger Nuclease (ZFN) target sites were designed for all of the 72 selected genomic loci in Zea mays. Numerous ZFP designs were developed and tested to identify the fingers which bound with the highest level of efficiency in a yeast proxy system with 72 different representative genomic loci target sites which were identified and selected in Zea mays. The specific ZFP recognition helices (Table 1) which bound with the highest level of efficiency to the zinc finger recognition sequences were used for targeting and integration of a donor sequence within the Zea mays genome.

TABLE 1

Zinc finger designs for the *Zea mays* selected genomic loci (N/A indicates "not applicable").

| pDAB Number | ZFP Number | F1 | F2 | F3 | F4 | F5 | F6 |
|---|---|---|---|---|---|---|---|
| 111879 | 111879 ZFN5 | SEQ ID NO: 1 QSGDLTR | SEQ ID NO: 2 RKDQLVA | SEQ ID NO: 3 RSDDLTR | SEQ ID NO: 4 TSSNRKT | SEQ ID NO: 5 RSDTLSE | SEQ ID NO: 6 ARSTRTN |
|  | 111879 ZFN7 | SEQ ID NO: 7 RSDSLSV | SEQ ID NO: 8 DRSNRKT | SEQ ID NO: 9 QSSHLTR | SEQ ID NO: 10 RSDALAR | SEQ ID NO: 11 RSDDLTR | SEQ ID NO: 12 DPSALRK |
| 111885 | 111885 ZFN1 | SEQ ID NO: 13 RSDNLSQ | SEQ ID NO: 14 ASNDRKK | SEQ ID NO: 15 ERGTLAR | SEQ ID NO: 16 RSDHLSR | SEQ ID NO: 17 ERGTLAR | SEQ ID NO: 18 QSGHLSR |
|  | 111885 ZFN2 | SEQ ID NO: 19 RSANLAR | SEQ ID NO: 20 DRSDLSR | SEQ ID NO: 21 RSDTLSQ | SEQ ID NO: 22 RSADLSR | SEQ ID NO: 23 DRSNLSR | SEQ ID NO: 24 NSRNLRN |
| 117404 | SIG115737_3 1v1 | SEQ ID NO: 25 RSDSLSV | SEQ ID NO: 26 DRSHLAR | SEQ ID NO: 27 DRSNLSR | SEQ ID NO: 28 RRSDLKR | SEQ ID NO: 29 RSDTLSE | SEQ ID NO: 30 QNATRIN |
|  | SIG115737_3 2v1 | SEQ ID NO: 31 QSGSLTR | SEQ ID NO: 32 QSGDLTR | SEQ ID NO: 33 RSDVLSE | SEQ ID NO: 34 TRNGLKY | N/A | N/A |
| 117408 | SIG120523_1 1v1 | SEQ ID NO: 35 RSDNLSR | SEQ ID NO: 36 DNSNRKT | SEQ ID NO: 37 QNAHRKT | SEQ ID NO: 38 QKATRIT | SEQ ID NO: 39 DRSHLTR | SEQ ID NO: 40 RSDDRKK |
|  | SIG120523_1 2v1 | SEQ ID NO: 41 ASKTRTN | SEQ ID NO: 42 QSGSLTR | SEQ ID NO: 43 LRHHLTR | SEQ ID NO: 44 QSAHLKA | N/A | N/A |
| 117400 | SIG115246_5 | SEQ ID NO: 45 QSGDLTR | SEQ ID NO: 46 ASHNLRT | SEQ ID NO: 47 DRSNLTR | SEQ ID NO: 48 QSSDLSR | SEQ ID NO: 49 DAGNRNK | N/A |
|  | SIG115246_6 | SEQ ID NO: 50 DRSDLSR | SEQ ID NO: 51 RSDNLTR | SEQ ID NO: 52 DRSHLSR | SEQ ID NO: 53 TSGNLTR | SEQ ID NO: 54 QSSDLSR | N/A |
| 117402 | SIG115636_1 v1 | SEQ ID NO: 55 QSSDLSR | SEQ ID NO: 56 HRSTRNR | SEQ ID NO: 57 RSDDLTR | SEQ ID NO: 58 DRSNLKA | SEQ ID NO: 59 DRSHLTR | SEQ ID NO: 60 QRSTLKS |
|  | SIG115636_2 v1 | SEQ ID NO: 61 RSDALSR | SEQ ID NO: 62 RSDDLTR | SEQ ID NO: 63 DRSHLTR | SEQ ID NO: 64 TSSNRKT | SEQ ID NO: 65 RSDTLSE | SEQ ID NO: 66 DRSHLAR |
| 117406 | SIG120417_1 1v1 | SEQ ID NO: 67 DRSARTR | SEQ ID NO: 68 QSGHLSR | SEQ ID NO: 69 QSGNLAR | SEQ ID NO: 70 RSDVLST | SEQ ID NO: 71 RYAYLTS | SEQ ID NO: 72 RRWTLVG |
|  | SIG120417_1 2v1 | SEQ ID NO: 73 RSDNLSQ | SEQ ID NO: 74 ASNDRKK | SEQ ID NO: 75 QSGDLTR | SEQ ID NO: 76 LKDTLRR | SEQ ID NO: 77 QSGNLAR | N/A |
| 117411 | SIG120621_1 5v1 | SEQ ID NO: 78 QSGDLTR | SEQ ID NO: 79 MQNYLSR | SEQ ID NO: 80 RSDHLSE | SEQ ID NO: 81 QNANRKT | SEQ ID NO: 82 RSADLTR | N/A |
|  | SIG120621_1 6v1 | SEQ ID NO: 83 RSDNLSE | SEQ ID NO: 84 QSANRTK | SEQ ID NO: 85 RSDALSR | SEQ ID NO: 86 DRSALAR | SEQ ID NO: 87 RSDHLSE | SEQ ID NO: 88 DSQNRIK |

TABLE 1-continued

Zinc finger designs for the Zea mays selected genomic loci (N/A indicates "not applicable").

| pDAB Number | ZFP Number | F1 | F2 | F3 | F4 | F5 | F6 |
|---|---|---|---|---|---|---|---|
| 117413 | SIG12078_11 v1 | SEQ ID NO: 89 QSGDLTR | SEQ ID NO: 90 DKGNLTK | SEQ ID NO: 91 RSADLTR | SEQ ID NO: 92 DRSHLAR | SEQ ID NO: 93 RSDTLSE | SEQ ID NO: 94 DRSNRKT |
|  | SIG12078_12 v1 | SEQ ID NO: 95 DRSNLSR | SEQ ID NO: 96 LRQDLKR | SEQ ID NO: 97 RSDHLSE | SEQ ID NO: 98 DRSALAR | SEQ ID NO: 99 DRSALSR | SEQ ID NO: 100 NRRGRWS |
| 117429 | SIG157315_1 v1 | SEQ ID NO: 101 RPYTLRL | SEQ ID NO: 102 HRSSLRR | SEQ ID NO: 103 RSDSLLR | SEQ ID NO: 104 WLSSLSA | SEQ ID NO: 105 QSGDLTR | SEQ ID NO: 106 DRSHLAR |
|  | SIG157315_2 v1 | SEQ ID NO: 107 DRSNLSR | SEQ ID NO: 108 LKQHLNE | SEQ ID NO: 109 LRHHLTR | SEQ ID NO: 110 QSGNLHV | SEQ ID NO: 111 TSGHLSR | N/A |

TABLE 2

Target site of Zea mays selected genomic loci.

| Locus ID | Name | pDAB Number | ZFP Number and Binding Site (5'→3') | SEQ ID NO: |
|---|---|---|---|---|
| optimal_loci_204637 | OGL1 | pDAB111879 | 111879ZFN5: ctACTCCGTATGCGAAGGCAcg | 112 |
|  |  |  | 111879ZFN7: taTTCGCGGTGGGACACTTGat | 113 |
| optimal_loci_204726 | OGL2 | pDAB111885 | 111885ZFN1: ccGGAGCCGGGGCCTCCCAGgc | 114 |
|  |  |  | 111885ZFN2: atCGCGACGCGACGcGACGAGac | 115 |
| optimal_loci_156393 | OGL12 | pDAB117404 | SIG115737_31v1: TGCATGCGCAGTA | 116 |
|  |  |  | SIG115737_32v1: ACACCGGCGCACGGCACG | 117 |
| optimal_loci_198387 | OGL15 | pDAB117408 | SIG120523_11v1: AGAGGTGTAACC | 118 |
|  |  |  | SIG120523_12v1: TCGGGCACAAGAAACGAG | 119 |
| optimal_loci_31710 | OGL08 | pDAB117400 | SIG115246_5: TACGCTGACAATGCA | 120 |
|  |  |  | SIG115246_6: CCAGCTGATGGAGAGGAC | 121 |
| optimal_loci_31710 | OGL11 | pDAB117402 | SIG115636_1v1: AGAGCAGGCGAG | 122 |
|  |  |  | SIG115636_2v1: AGCAAAGTGAGTAGTT | 123 |
| optimal_loci_197372 | OGL14 | pDAB117406 | SIG120417_11v1: TGGATGGAAGGAATC | 124 |
|  |  |  | SIG120417_12v1: GAAGCTACATCCCAG | 125 |
| optimal_loci_232228 | OGL16 | pDAB117411 | SIG120621_15v1: TACGCGCAACGGAACGCA | 126 |
|  |  |  | SIG120621_16v1: CACCGGTGTCGTGTAACAG | 127 |
| optimal_loci_285621 | OGL17 | pDAB117413 | SIG12078_11v1: CCCGGACGACGCCGAG | 128 |
|  |  |  | SIG12078_12v1: GACATGGCACGCGCATCGAG | 129 |

TABLE 2-continued

Target site of Zea mays selected genomic loci.

| Locus ID | Name | pDAB Number | ZFP Number and Binding Site (5'→3') | SEQ ID NO: |
|---|---|---|---|---|
| optimal_loci_1 57315 | OGL 13 | pDAB117429 | SIG157315_1v1: GCATGTGTGGTTTTG | 130 |
| | | | SIG157315_2v1: GGTCAAGGTAGTGAC | 131 |

The Zea mays representative genomic loci zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid linker and an opaque-2 nuclear localization signal derived from Zea mays to form zinc-finger nucleases (ZFNs). See, U.S. Pat. No. 7,888,121. Zinc fingers for the various functional domains were selected for in vivo use. Of the numerous ZFNs that were designed, produced and tested to bind to the putative genomic target site, the ZFNs described in Table 2 above were identified as having in vivo activity and were characterized as being capable of efficiently binding and cleaving the unique Zea mays genomic polynucleotide target sites in planta.

ZFN Construct Assembly

Plasmid vectors containing ZFN gene expression constructs, which were identified as previously described, were designed and completed using skills and techniques commonly known in the art (see, for example, Ausubel or Maniatis). Each ZFN-encoding sequence was fused to a sequence encoding an opaque-2 nuclear localization signal (Maddaloni et al., (1989) Nuc. Acids Res. 17:7532), that was positioned upstream of the zinc finger nuclease. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569). Expression of the fusion proteins was driven by the strong constitutive promoter from the Zea mays Ubiquitin gene, (which includes the 5' untranslated region (UTR) (Told et al., (1992) Plant Physiology 100; 1503-07). The expression cassette also included the 3' UTR (comprising the transcriptional terminator and polyadenylation site) from the Zea mays peroxidase 5 gene (Per5) gene (US Patent Publication No. 2004/0158887). The self-hydrolyzing 2A encoding the nucleotide sequence from Thosea asigna virus (Szymczak et al., (2004) Nat Biotechnol. 22:760-760) was added between the two Zinc Finger Nuclease fusion proteins that were cloned into the construct.

The plasmid vectors were assembled using the IN-FUSION™ Advantage Technology (Clontech, Mountain View, Calif.). Restriction endonucleases were obtained from New England BioLabs (Ipswich, Mass.) and T4 DNA Ligase (Invitrogen, Carlsbad, Calif.) was used for DNA ligation. Plasmid preparations were performed using NUCLEO-SPIN® Plasmid Kit (Macherey-Nagel Inc., Bethlehem, Pa.) or the Plasmid Midi Kit (Qiagen) following the instructions of the suppliers. DNA fragments were isolated using QIA-QUICK GEL EXTRACTION KIT™ (Qiagen) after agarose tris-acetate gel electrophoresis. Colonies of all ligation reactions were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Universal Donor Construct Assembly

To support rapid testing of a large number of target loci, a novel, flexible universal donor system sequence was designed and constructed. The universal donor polynucleotide sequence was compatible with high throughput vector construction methodologies and analysis. The universal donor system was composed of at least three modular domains: a non-variable ZFN binding domain, an analytical and user defined features domain, and a simple plasmid backbone for vector scale up. The non-variable universal donor polynucleotide sequence was common to all donors and permits design of a finite set of assays that can be used across all of the Zea mays target sites thus providing uniformity in targeting assessment and reducing analytical cycle times. The modular nature of these domains allowed for high throughput donor assembly. Additionally, the universal donor polynucleotide sequence has other unique features aimed at simplifying downstream analysis and enhancing the interpretation of results. It contained an asymmetric restriction site sequence that allowed for the digestion of PCR products into diagnostically predicted sizes. Sequences comprising secondary structures that were expected to be problematic in PCR amplification were removed. The universal donor polynucleotide sequence was small in size (less than 3.0 Kb). Finally, the universal donor polynucleotide sequence was built upon the high copy pUC19 backbone that allows a large amount of test DNA to be bulked in a timely fashion.

Figure 2:
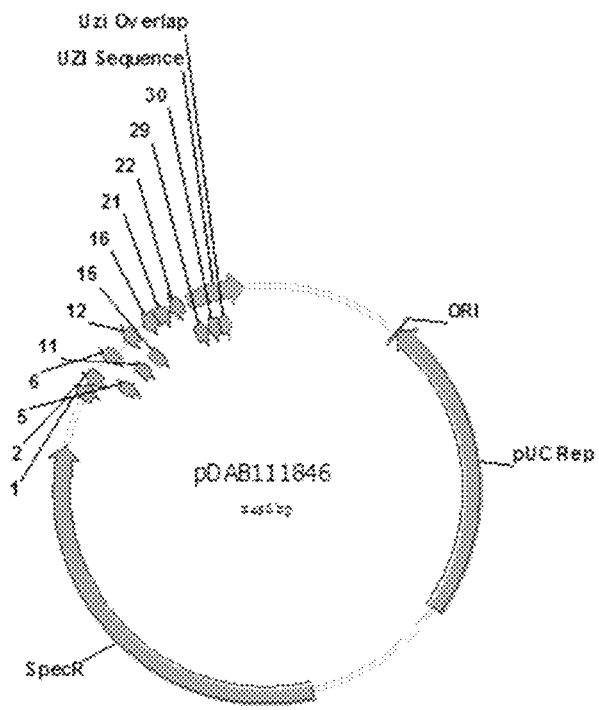
FIG. 2 illustrates a plasmid map of pDAB111846.
Figure 3:
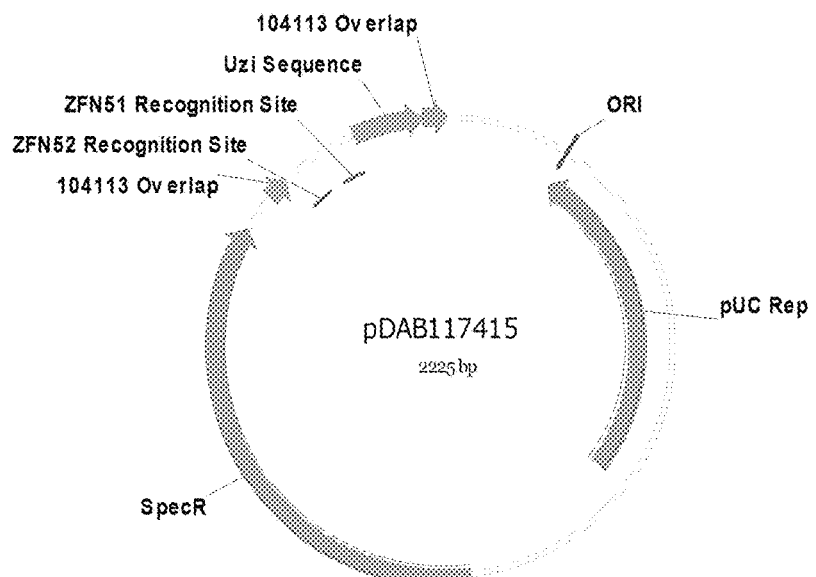
FIG. 3 illustrates a plasmid map of pDAB117415.
Figure 4:
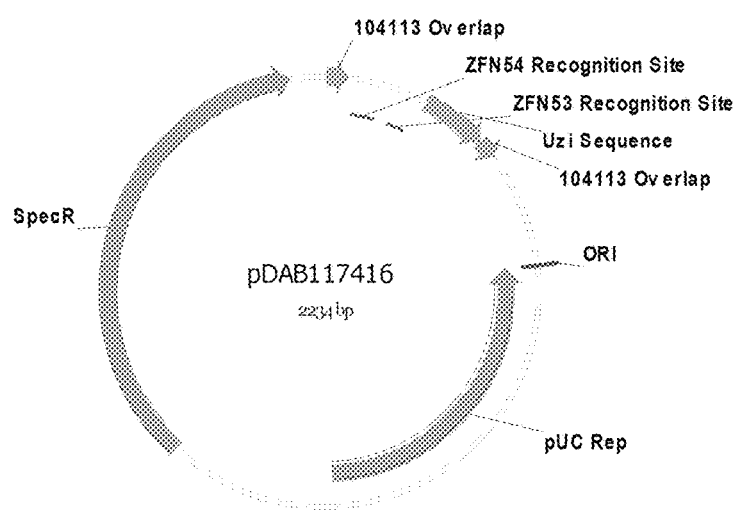
FIG. 4 illustrates a plasmid map of pDAB117416.
Figure 5:
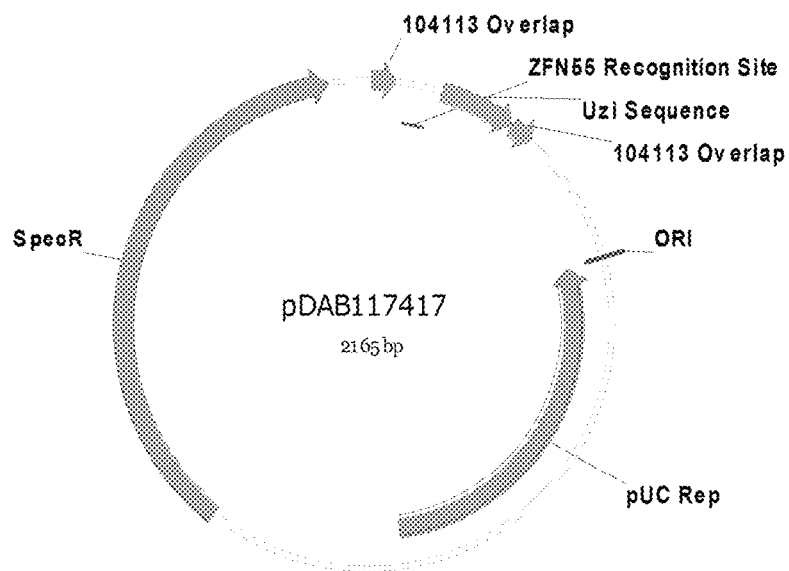
FIG. 5 illustrates a plasmid map of pDAB117417.
Figure 6:
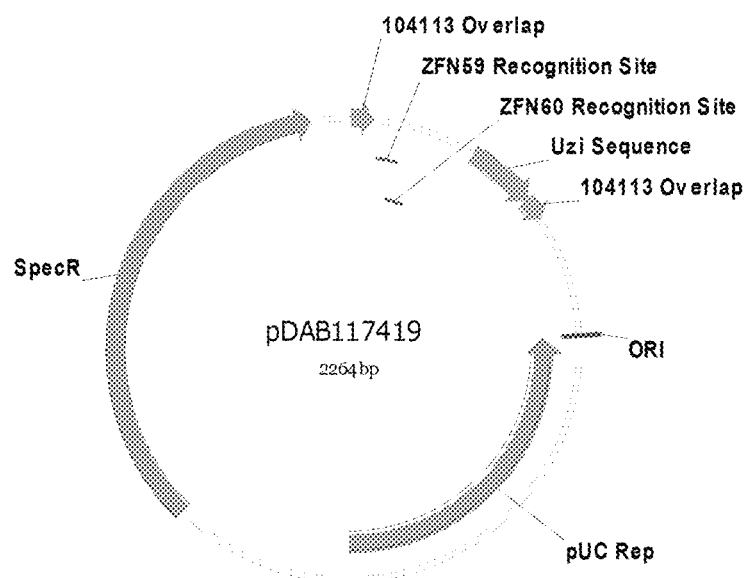
FIG. 6 illustrates a plasmid map of pDAB117419.
Figure 7:
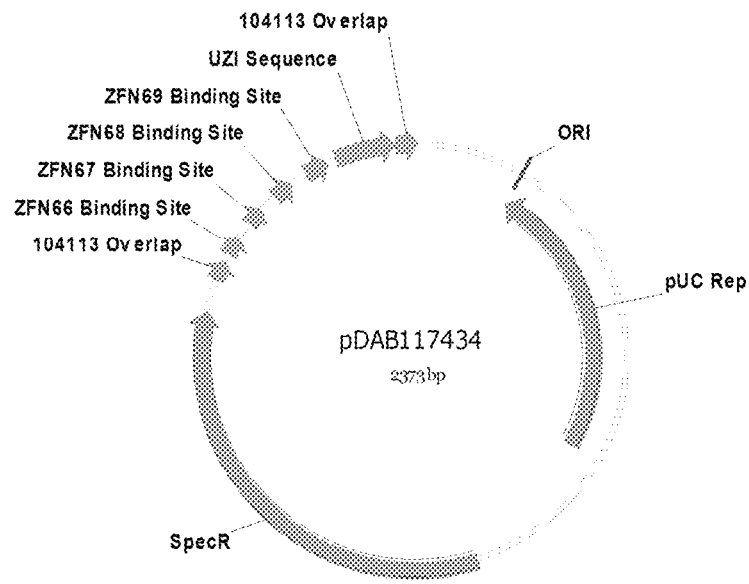
FIG. 7 illustrates a plasmid map of pDAB117434.
Figure 8:
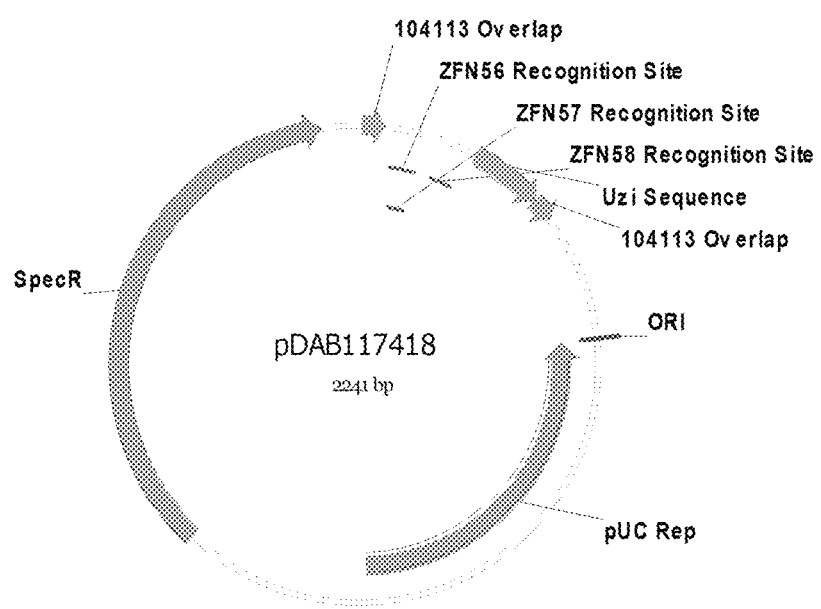
FIG. 8 illustrates a plasmid map of pDAB117418.
Figure 9:
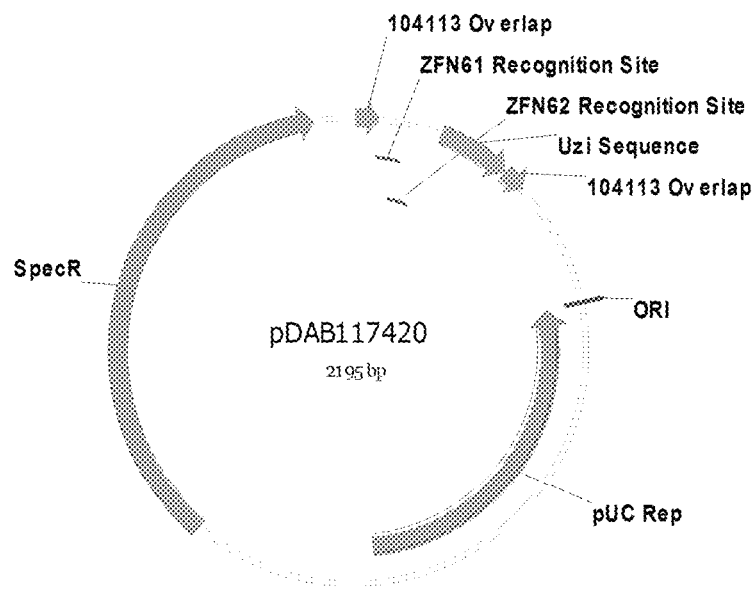
FIG. 9 illustrates a plasmid map of pDAB117420.
Figure 10:
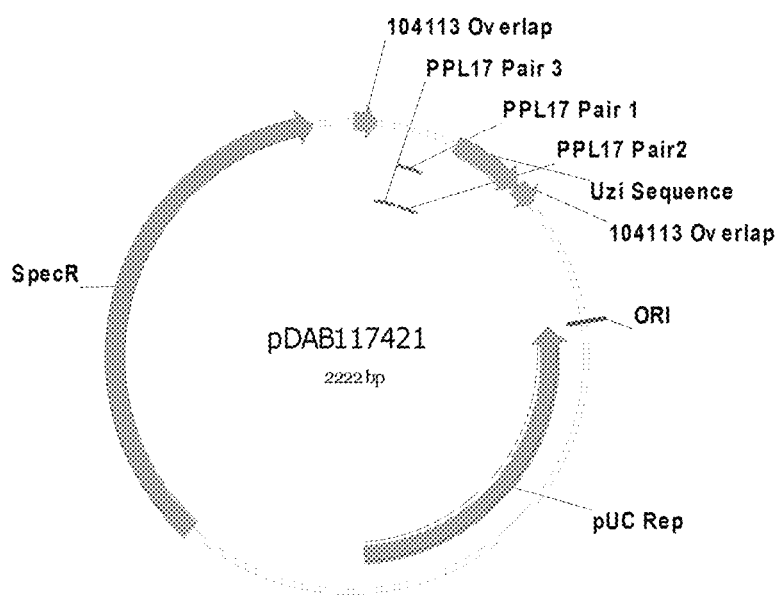
FIG. 10 illustrates a plasmid map of pDAB117421.

As an embodiment, an example plasmid comprising a universal polynucleotide donor cassette sequence is provided as SEQ ID NO:132 and FIG. 1. In an additional embodiment, a polynucleotide donor cassette sequence is provided as: pDAB111846, SEQ ID NO:133, FIG. 2; pDAB117415, SEQ ID NO:134, FIG. 3; pDAB117416, SEQ ID NO:135, FIG. 4; pDAB117417, SEQ ID NO:136, FIG. 5; pDAB117419, SEQ ID NO:137, FIG. 6; pDAB117434 SEQ ID NO:138, FIG. 7; pDAB117418, SEQ ID NO:139, FIG. 8; pDAB117420, SEQ ID NO:140, FIG. 9; and, pDAB117421, SEQ ID NO:141, FIG. 10. In another embodiment, additional sequences comprising the universal donor polynucleotide sequence with functionally expressing coding sequence or nonfunctional (promoterless) expressing coding sequences can be constructed. The various domains (a non-variable ZFN binding domain, an analytical and user defined features domain, and a simple plasmid backbone) that make up the universal donor system are annotated for the constructs, as described above, in Table 3.

TABLE 3

Annotation of universal donor system vectors to identify the non-variable ZFN binding domains, analytical and user defined features domain, and plasmid backbone.

| Vector Name | ZFN Binding Domain | Analytical Domain | Homology Arm Regions | Plasmid Backbone |
| --- | --- | --- | --- | --- |
| pDAB111845 | 2244-144 Bp | 145-254 Bp | — | 255-2243 Bp |
| pDAB111846 | 2243-143 Bp | 144-253 Bp | — | 254-2242 Bp |
| pDAB117415 | 1961-2069 Bp | 2081-2190 Bp | 1920-1954 Bp, 2191-2225 Bp | 2226-1919 Bp |
| pDAB117416 | 51-155 Bp | 171-280 Bp | 1-35 Bp, 281-315 Bp | 316-2234 Bp |
| pDAB117417 | 51-86 Bp | 102-211 Bp | 1-35 Bp, 212-246 Bp | 247-2165 Bp |
| pDAB117419 | 51-119 Bp | 201-310 Bp | 1-35 Bp, 311-345 Bp | 345-2264 Bp |
| pDAB117434 | 1970-2213 Bp | 2229-2338 Bp | 1920-1954 Bp, 2339-2373 Bp | 1-1919 Bp |
| pDAB117418 | 51-162 Bp | 178-287 Bp | 1-35 Bp, 288-322 Bp | 323-2241 Bp |
| pDAB117420 | 37-116 Bp | 132-241 Bp | 1-35 Bp, 242-276 Bp | 277-2195 Bp |
| pDAB117421 | 51-143 Bp | 159-268 Bp | 1-35 Bp, 269-303 Bp | 304-2222 Bp |

Figure 11:
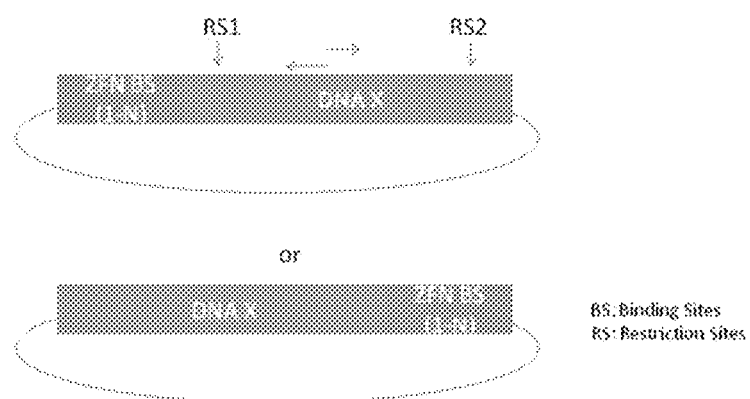
FIG. 11 illustrates a representation of the universal donor polynucleotide sequence for integration via NHEJ.

In another embodiment, the universal donor polynucleotide sequence is a small 2-3 Kb modular donor system delivered as a plasmid. This is a minimal donor, comprising any number of ZFN binding sites, a short 100-150 bp template region referred to as "DNA X" or "UZI Sequence" or "analytical domain" (SEQ ID NO:142 and SEQ ID NO:143) that carries restriction sites and DNA sequences for primer design (primers are designed at a Tm of 10° C. greater than any calculated secondary structures) or coding sequences, and a simple plasmid backbone (FIG. 11). In an embodiment, the analytical domain is designed: to contain a guanine and cytosine base pair percentage of 40 to 60%; to not contain repetitive sequences of more than 9 Bp (e.g., 5'-gtatttcatgtatttcat-3'); to not contain a series of identical base pairs greater than 9 Bp; and, is free of secondary structure, where the secondary structure is less than −18 kcal/mol of free energy as calculated by Markham, N. R. & Zuker, M. (2008) UNAFold: software for nucleic acid folding and hybridization. In Keith, J. M., editor, Bioinformatics, Volume II. Structure, Function and Applications, number 453 in Methods in Molecular Biology, chapter 1, pages 3-31. Humana Press, Totowa, N.J. ISBN 978-1-60327-428-9. See, Table 4. The entire plasmid is inserted through NHEJ following DNA double strand break at the appropriate ZFN binding site; the ZFN binding sites can be incorporated tandemly. This embodiment of a universal donor polynucleotide sequence is most suitable for rapid screening of target sites and ZFNs, and sequences that are difficult to amplify are minimized in the donor.

TABLE 4

Analysis of the analytical domain composition for ΔG free energy, number of 9 Bp runs of identical base pairs, number of repetitive sequences of more than 9 Bp, and guanine/cytosine percentage.

| SEQ ID NO: | ΔG free energy | Number of 9 Bp runs of identical base pairs | Number of repetitive Sequences of more than 9 Bp | GC % |
| --- | --- | --- | --- | --- |
| SEQ ID NO: 142 | −12.42 kcal/mol | None | None | 50.9% |
| SEQ ID NO: 143 | −12.78 kcal/mol | None | None | 47.5% |

Figure 12:
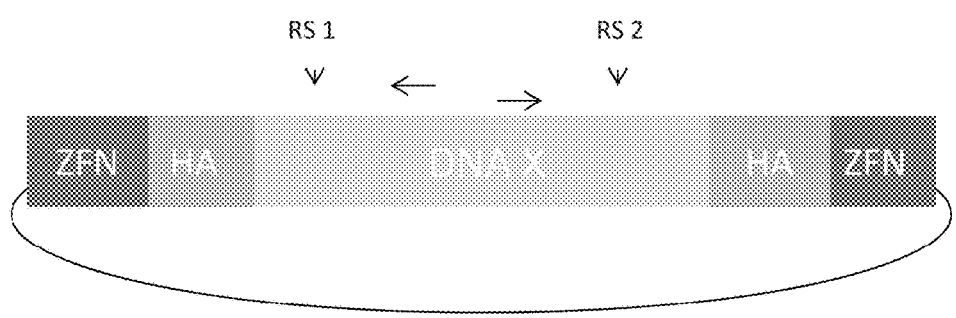
FIG. 12 illustrates a representation of the universal donor polynucleotide sequence for integration via HDR. The label "HA" indicates homology arms; and the label "ZFN BS" indicates ZFN binding site (for monomer).

In a further embodiment the universal donor polynucleotide sequence is made up of at least four modules and carries partial ZFN binding sites, homology arms, DNA X with either the approximately 100 bp analytical piece or coding sequences. This embodiment of the universal donor polynucleotide sequence is suitable for interrogating NHEJ mediated gene insertion at a variety of polynucleotide target sites, with several ZFNs. (FIG. 12).

Figure 13:
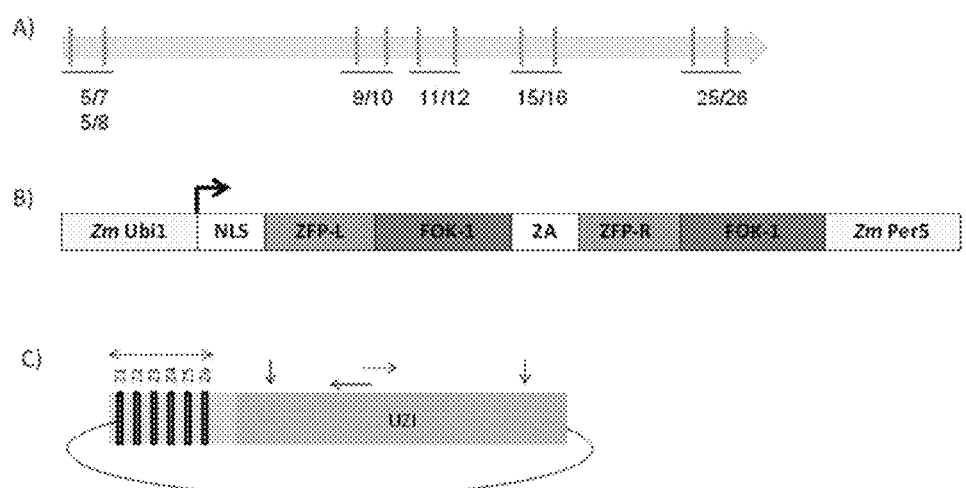
FIG. 13 illustrates the constructs used for targeting and validation of the universal donor polynucleotide system integration within the Zea mays select genomic loci targeting validation. A) ZFN design space with location of the ZFN pairs. B) Configuration of the ZFN expression construct. The label "NLS" indicates Nuclear Localization Signal, the label "ZFP" indicates Zinc Finger Protein. C) universal donor polynucleotide for NHEJ mediated targeting of Zea mays select genomic loci. Z1-Z6 represent ZFN binding sites specific for a Zea mays select genomic loci target. The number of ZFN sites can vary from 3-6. Vertical arrows show unique restriction sites and horizontal arrows represent potential PCR primer sites. The universal donor polynucleotide system is a short (110 bp) sequence that is common to all donors used for integration within Zea mays select genomic loci.

The universal donor polynucleotide sequence can be used with all targeting molecules with defined DNA binding domains, with two modes of targeted donor insertion (NHEJ/HDR). As such, when the universal donor polynucleotide sequence is co-delivered with the appropriate ZFN expression construct, the donor vector and the maize genome are both cleaved in one specific location dictated by the binding of the particular ZFN. Once linearized, the donor can be incorporated into the genome by NHEJ or HDR. The different analytical considerations in the vector design can then be exploited to determine the Zinc Finger which maximizes the efficient delivery of targeted integration. (FIG. 13).

Example 2: Zea mays Transformation Procedures

Before delivery to Zea mays c.v. Hi-II protoplasts, plasmid DNA for each ZFN construct was prepared from cultures of E. coli using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Protoplast Isolation

Zea mays c.v. Hi-II suspension cells were maintained at a 3.5 day maintenance schedule, 4 mL packed cell volume (PCV) of cells were collected and transferred to 50 mL sterile conical tubes (Fisher Scientific) containing 20 mL of enzyme solution (0.6% PECTOLYASE™, 6% CELLULASE™ ("Onozuka" R10; Yakult Pharmaceuticals, Japan), 4 mM MES (pH 5.7), 0.6 M mannitol, 15 mM $MgCl_2$). The cultures were capped and wrapped in PARAFILM™ and placed on a platform rocker (Thermo Scientific, Van Mix platform Rocker) at speed setting 10 for incubation for 16-18 hours at room temperature until protoplasts were released. Following incubation, cells were microscopically evaluated for quality of digestion. The digested cells were filtered through a 100 μm cell strainer, rinsed with 10 mL W5 media [2 mM MES (pH5.7), 205 mM NaCl, 167 mM CaCl$_2$, 6.7 mM KCl], followed by filtering through 70 μm and 40 μm cell strainers. The 100 μm and 40 μm strainers were rinsed with 10 mL W5 media. The filtered protoplasts along with rinsed media were collected in a 50 ml centrifuge tube and final volume was approximately 40 mL. Then, 8 mL of "Heavy Gradient solution" [500 mM sucrose, 1 mM CaCl$_2$, 5 mM MES (pH6.0)] was then slowly added to the bottom of the protoplast/enzyme solution, centrifuged in a centrifuge with a swing arm bucket rotor for 15 minutes at 300-350×g. Following centrifugation, about 7-8 mL of the protoplast band was removed, washed with 25 mL of W5, and centrifuged for 15 minutes at 180-200×g. The protoplasts were then resuspended in 10 mLs of MMG solution[4 mM MES (pH 5.7), 0.6 M mannitol, 15 mM MgCl$_2$]. Protoplasts were counted using a haemocytometer or flow cytometer and diluted to 1.67 million per ml using MMG.

Transformation of *Zea mays* c.v. Hi-II Suspension Culture Derived Protoplasts Using PEG Approximately 0.5 million protoplasts (300 μL in MMG solution) were transferred to 2 mL tubes, mixed with 40 μL of DNA and incubated at room temperature for 5-10 minutes. Next, 300 μL of freshly prepared PEG solution (36% PEG 4000, 0.3 M mannitol, 0.4M CaCl$_2$) was added, and the mixture was incubated at room temperature 15-20 minutes with periodic mixing by inversion. After incubation, 1 mL of W5 wash was added slowly, the cells mixed gently and protoplasts were pelleted by centrifugation at 180-200×g for 15 minutes. The pellet was resuspended in 1 ml of WI media [4 mM MES (pH 5.7), 0.6 M mannitol, 20 mM KCl] the tube wrapped with aluminum foil and incubated in room temperature overnight for about 16 hours.

Transformation of ZFN and Donor

Figure 14:
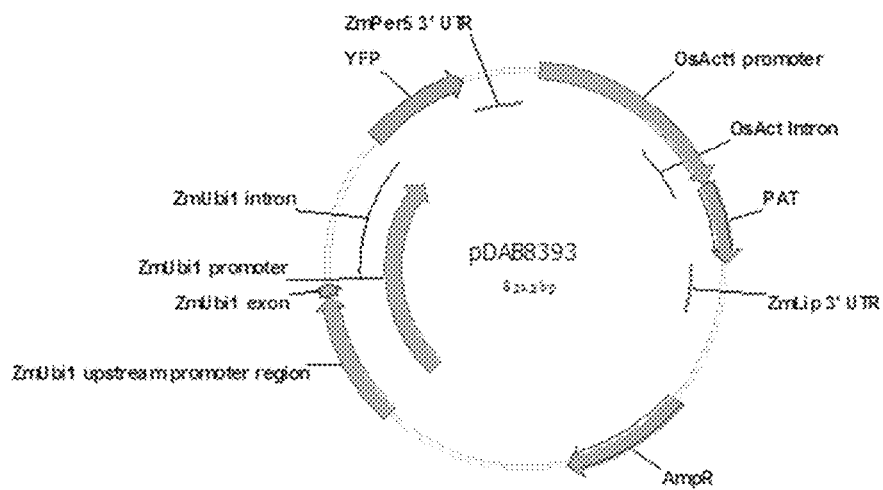
FIG. 14 illustrates a plasmid map of pDAB8393.

For each of the selected genomic loci, the *Zea mays* protoplasts were transfected with a yfp gene expressing control, ZFN alone, donor alone and a mixture of ZFN and donor at 1:10 ratio (by weight). The total amount of DNA for transfection of 0.5 million protoplasts was 80 μg. All treatments were conducted in replicates of either three or six. The yfp gene expressing control used was pDAB8393 (FIG. 14) containing the *Zea mays* Ubiquitin 1 promoter—yellow fluorescent protein coding sequence—*Zea mays* Per5 3'UTR and the Rice Actin1 promoter—pat coding sequence—*Zea mays* lipase 3'UTR gene expression cassettes. In a typical targeting experiment, 4 μg of ZFN alone or with 36 μg of donor were co-transfected, 40 μg of YFP reporter gene construct was added to each treatment. Inclusion of consistent amounts of yfp gene expressing plasmid as filler allows assessment of transfection quality across multiple loci and replicate treatments. In addition, the use of consistent amounts of yfp gene expressing plasmids allows for the quick trouble shooting of any technical issues in the rapid targeting analysis of the donor insertion.

Example 3: Cleavage of Genomic Loci in *Zea mays* Via Zinc Finger Nuclease

ZFN transfected *Zea mays* c.v. Hi-II protoplasts were harvested 24 hours post-transfection by centrifugation at 1600 rpm in 2 mL EPPENDORF™ tubes and the supernatant was removed. Genomic DNA was extracted from protoplast pellets using the QIAGEN PLANT DNA EXTRACTION KIT™ (Qiagen, Valencia, Calif.). The isolated DNA was resuspended in 50 μL of water and concentration was determined by NANODROP® (Invitrogen, Grand Island, N.Y.). The integrity of the DNA was estimated by running samples on 0.8% agarose gel electrophoresis. All samples were normalized (20-25 ng/μL) for PCR amplification to generate amplicons for sequencing (Illumina, Inc., San Diego, Calif.). Bar-coded PCR primers for amplifying regions encompassing each test ZFN recognition sequence from treated and control samples were designed and purchased from IDT (Coralville, Iowa, HPLC purified). Optimum amplification conditions were identified by gradient PCR using 0.2 μM appropriate bar-coded primers, ACCUPRIME PFX SUPERMIX™ (Invitrogen, Carlsbad, Calif.) and 100 ng of template genomic DNA in a 23.5 μL reaction. Cycling parameters were initial denaturation at 95° C. (5 min) followed by 35 cycles of denaturation (95° C., 15 sec), annealing (55-72° C., 30 sec), extension (68° C., 1 min) and a final extension (68° C., 7 min). Amplification products were analyzed on 3.5% TAE agarose gels and appropriate annealing temperature for each primer combination was determined and used to amplify amplicons from control and ZFN treated samples as described above. All amplicons were purified on 3.5% agarose gels, eluted in water and concentrations were determined by NANODROP™. For Next Generation Sequencing, approximately 100 ng of PCR amplicon from the ZFN treated and corresponding maize protoplast controls were pooled together and sequenced using Illumina Next Generation Sequencing (NGS).

Figures 15A, 15B:
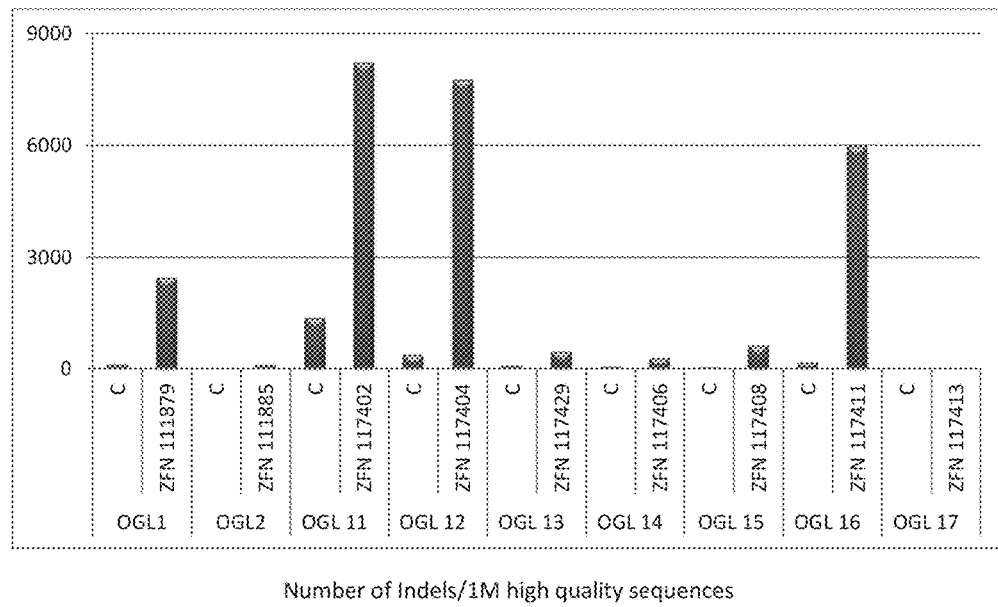
FIGS. 15A & 15B illustrate the ZFN cleavage activity at Zea mays selected genomic loci targets. Cleavage activity is represented as number of sequences with Indels at the ZFN cleavage site per one million high quality reads.

The cleavage activity of appropriate ZFNs at each *Zea mays* selected genomic loci were assayed. Short amplicons encompassing the ZFN cleavage sites were amplified from the genomic DNA and subjected to Illumina NGS from ZFN treated and control protoplasts. The ZFN induced cleavage or DNA double strand break was resolved by the cellular NHEJ repair pathway by insertion or deletion of nucleotides (Indels) at the cleavage site and presence of Indels at the cleavage site is thus a measure of ZFN activity and was determined by NGS. Cleavage activity of the target specific ZFNs was estimated as the number of sequences with Indels per one million high quality sequences using NGS analysis software (Patent publication 2012-0173,153, data Analysis of DNA sequences) (FIG. 15). Activities in the range of 5-100 fold over controls were observed for *Zea mays* selected genomic loci targets and were further confirmed by sequence alignments that showed a diverse footprint of Indels at each ZFN cleavage site. This data suggests that the *Zea mays* selected genomic loci are amenable to cleavage by ZFNs. Differential activity at each target is reflective of its chromatin state and amenability to cleavage as well as the efficiency of expression of each ZFN.

Figure 16:
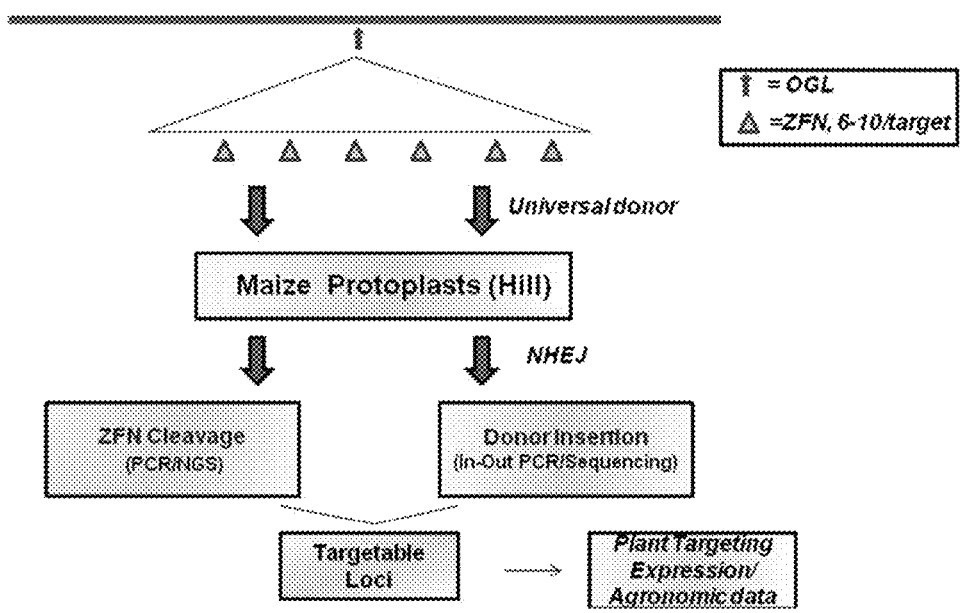
FIG. 16 illustrates the validation of Zea mays selected genomic loci targets using NHEJ based Rapid Targeting Analysis method.
Figure 17:
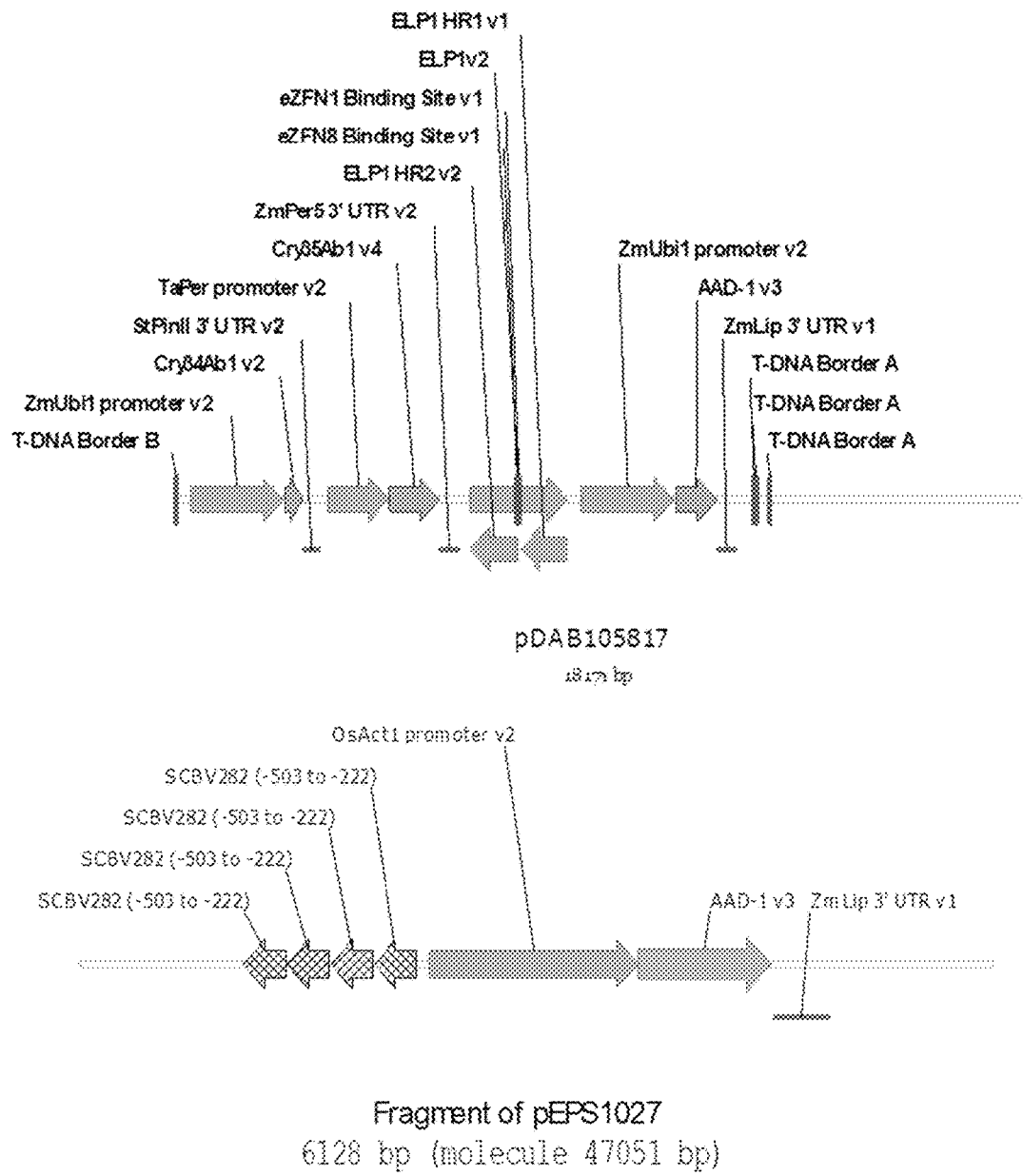
FIG. 17 illustrates plasmid constructs transformed into Zea mays via random integration that comprise the events used for flanking sequence analysis and transgene expression studies.

Example 4: Rapid Targeting Analysis of the Integration of a Polynucleotide Donor Sequence within the Genomic Loci in *Zea mays* via Zinc Finger Nuclease Validation of the targeting of the universal donor polynucleotide sequence within the *Zea mays* selected genomic loci targets via non-homologous end joining (NHEJ) mediated donor insertion, was performed using a semi-throughput protoplast based Rapid Targeting Analysis method. For each *Zea mays* selected genomic loci target, three to six ZFN designs were tested and targeting was assessed by measuring ZFN mediated cleavage by Next Generation Sequencing methods (FIG. 15) and donor insertion by junctional In-Out PCR (FIG. 16). *Zea mays* selected genomic loci that were positive in both assays were identified as a targetable locus.

ZFN Donor Insertion Rapid Targeting Analysis

To determine if a *Zea mays* selected genomic loci target can be targeted for donor insertion, a ZFN construct and universal donor polynucleotide construct were co-delivered to maize protoplasts which were incubated for 24 hours before the genomic DNA was extracted for analysis. If the expressed ZFN was able to cut the target binding site both at the *Zea mays* selected genomic loci target and in the donor, the linearized donor would then be inserted into the cleaved target site in the maize genome via the non-homologous end joining (NHEJ) pathway. Confirmation of targeted integration at the *Zea mays* selected genomic loci target was completed based on an "In-Out" PCR strategy, where an "Out" primer recognizes sequence at the native genomic loci and an "In" primer binds to sequence within the donor DNA. The primers are designed in a way that only when the donor DNA is inserted at the *Zea mays* selected genomic loci target, would the PCR assay produce an amplification product of an expected size. The In-Out PCR assay is performed at both the 5'- and 3'-ends of the insertion junction. The primers used for the analysis of integrated polynucleotide donor sequences are provided in Table 5.

ZFN Donor insertion at Target Loci using nested "In-Out" PCR

All PCR amplifications were conducted using a TAKARA EX TAQ HS™ kit (Clonetech, Mountain View, Calif.). The first In-Out PCR was carried out in 20 μL final reaction volume that contains 1×TAKARA EX TAQ HS™ buffer, 0.2 mM dNTPs, 0.2 μM "Out" primer (Table 5), 0.05 μM "In" primer (designed from the universal donor cassette described above), 0.75 unit of TAKARA EX TAQ HS™ polymerase, and 10 ng extracted maize protoplast DNA. The reaction was then carried out using a PCR program that consisted of 94° C. for 2 min, 20 cycles of 98° C. for 12 sec and 68° C. for 2 min, followed by 72° C. for 10 min and held at 4° C. Final PCR products were run on an agarose gel along with 1 KB PLUS DNA LADDER™ (Life Technologies, Grand Island, N.Y.) for visualization.

The nested In-Out PCR was conducted in a 20 μL final reaction volume that contained 1×TAKARA EX TAQ HS™ buffer, 0.2 mM dNTPs, 0.2 μM "Out" primer (Table 5), 0.1 μM "In" primer (designed from the universal donor cassette described above, Table 6), 0.75 unit of TAKARA EX TAQ HS™ polymerase, and 1 μL of the first PCR product. The reaction was then carried out using a PCR program that consisted of 94° C. for 2 min, 31 cycles of 98° C. for 12 sec, 66° C. for 30 sec and 68° C. for 45 sec, followed by 72° C. for 10 min and held at 4° C. Final PCR products were run on an agarose gel along with 1 KB PLUS DNA LADDER™ (Life Technologies, Grand Island, N.Y.) for visualization.

TABLE 5

List of all "Out" primers for nested In-Out PCR analysis of optimal genomic loci.

| | | | | |
|---|---|---|---|---|
| OGL1 | First PCR | 5'- end | APL02-5PriF1 | SEQ ID NO: 144 CGCCACAAATCTGAACCAGCA |
| | | | Spec-PriR1 | SEQ ID NO: 145 CCACGATCGACATTGATCTGGCTA |
| | | 3'- end | APL02-3PriR1 | SEQ ID NO: 146 GCGACATATCAGGCCAACAGG |
| | | | Uzi-PriF1 | SEQ ID NO: 147 GGGATATGTGTCCTACCGTATCAGG |
| | Nest PCR | 5'- end | APL02-5nstPriF1 | SEQ ID NO: 148 CCAGCATACAGTTAGGGCCCA |
| | | | Spec-nst PriR1 | SEQ ID NO: 149 GTTGCCTTGGTAGGTCCAGC |
| | | 3'- end | APL02-3nstPriR1 | SEQ ID NO: 150 CGAAAACTCAGCATGCGGGAA |
| | | | Uzi-nstPriF1 | SEQ ID NO: 151 GAGCCATCAGTCCAACACTGC |

TABLE 5-continued

List of all "Out" primers for nested In-Out PCR analysis of optimal genomic loci.

| | | | | |
|---|---|---|---|---|
| OGL2 | First PCR | 5'- end | APL01-5PriF1 | SEQ ID NO: 152 ACAGGCGTACAGCAACACCA |
| | | 3'- end | APL01-3PriR1 | SEQ ID NO: 153 GACCCTATGGTGTTGGATCCCA |
| | Nest PCR | 5'- end | APL01-5nstPriF1 | SEQ ID NO: 154 CGGGAGCTAGGCAACAAATCG |
| | | 3'- end | APL01-3nstPriR1 | SEQ ID NO: 155 TCTGACTAAACGGGTGGATGCTG |
| OGL8 | First PCR | 5'- end | OGL08-5nstPriF2 | SEQ ID NO: 156 CGGATCAGTTGATTCGCTCACTTTCA |
| | | 3'- end | OGL08-3PriR | SEQ ID NO: 157 GCCGAAAAGCAGCAACTGGAA |
| | Nest PCR | 5'- end | OGL08-5nstPriF | SEQ ID NO: 158 GATTGCTACGCAGACCGCCTA |
| | | 3'- end | OGL08-3nstPriR | SEQ ID NO: 159 CACTATTCCTCCGGCATGCAG |
| OGL 11 | First PCR | 5'- end | OGL11-5PriF | SEQ ID NO: 160 TGACCTATTGATCGGTCGGCTC |
| | | 3' end | OGL11-3PriR2 | SEQ ID NO: 161 TGCCTTGAATCTCAGGGATGCA |
| | Nest PCR | 5'- end | OGL11-5nstPriF | SEQ ID NO: 162 GCCGAAGCTAACTAGCGGACA |
| | | 3'- end | OGL11-3nstPriR2 | SEQ ID NO: 163 CATGGAGTAGCAGCTGTGCTG |
| OGL 12 | First PCR | 5'- end | OGL12-5PriF | SEQ ID NO: 164 GAAAAGCAGTCACCGGCTCTG |
| | | 3'- end | OGL12-3PriR | SEQ ID NO: 165 CCATGGACATGAATTCGGCACG |
| | Nest PCR | 5'- end | OGL12-5nstPriF | SEQ ID NO: 166 CTTTTGCACCACGGAGCAGAC |
| | | 3'- end | OGL12-3nstPriR | SEQ ID NO: 167 GCTAGCAAAACTTTGAAGCTCGCTC |
| OGL 13 | First PCR | 5'- end | OGL13-5PriF | SEQ ID NO: 168 GAGGTCCCTTACGGGTCATCG |
| | | 3'- end | OGL13-3PriR | SEQ ID NO: 169 ACCAGGTCTATCTTGCGCAGAC |
| | Nest PCR | 5'- end | OGL13-5nstPriF | SEQ ID NO: 170 AATAGCGTGGTCGGGTCCTAG |
| | | 3'- end | OGL13-3nstPriR | SEQ ID NO: 171 ACGAACGATCCAAGGTGCAGT |
| OGL 14 | First PCR | 5'- end | OGL14-5PriF | SEQ ID NO: 172 TAGAGACGAGGACTCTGGGCT |
| | | 3'- end | OGL14-3PriR | SEQ ID NO: 173 AAGTCCAACATGGGCACAACC |
| | Nest PCR | 5'- end | OGL14-5nstPriF | SEQ ID NO: 174 CCTCGTTAAGGGTGCAGGTTG |
| | | 3'- end | OGL14-3nstPriR | SEQ ID NO: 175 CCAAGTCAGCTTCTAAGCCATCAAAC |
| OGL 15 | First PCR | 5'- end | OGL15-5PriF | SEQ ID NO: 176 AACCCTAGACTTCTGCCTGGTG |
| | | 3'- end | OGL15-3PriR | SEQ ID NO: 177 GCTCACTTACGAGCAGATCCCA |
| | Nest PCR | 5'- end | OGL15-5nstPriF | SEQ ID NO: 178 GGTGCACGCATGTTCTCATGT |
| | | 3'- end | OGL15-3nstPriR | SEQ ID NO: 179 TGTTTACCGCAGCCATGCTTG |
| OGL 16 | First PCR | 5'- end | OGL16-5PriF | SEQ ID NO: 180 GTTGTATACGGCATCCATCCGCT |
| | | 3'- end | OGL16-3PriR | SEQ ID NO: 181 GAATGAAACTGGTGGTCTGCTCC |
| | Nest PCR | 5'- end | OGL16-5nstPriF | SEQ ID NO: 182 CCGACGAGGTACAAGTAGCAGG |
| | | 3'- end | OGL16-3nstPriR | SEQ ID NO: 183 CCCGTAGTCCAGATTCTTGTGGT |

TABLE 5-continued

List of all "Out" primers for nested In-Out PCR analysis of optimal genomic loci.

| OGL 17 | First PCR | 5'-end | OGL17-5PriF | SEQ ID NO: 184 GTCGTTTGTTCGGAAGGGGAG |
|---|---|---|---|---|
| | | 3'-end | OGL17-3PriR | SEQ ID NO: 185 CGTAGTTGTCCGGCATGTCCT |
| | Nest PCR | 5'-end | OGL17-5nstPriF | SEQ ID NO: 186 TGTATCCCTTCGGTGAGCACG |
| | | 3'-end | OGL17-3nstPriR | SEQ ID NO: 187 TGAATCGACTCGCTGACAGGTG |

TABLE 6

List of all "In" primers for nested In-Out PCR analysis of optimal genomic loci.

| All Reactions | | 5'-end | Spec-PriR1 | SEQ ID NO: 188 CCACGATCGACATTGATCTGGCTA |
|---|---|---|---|---|
| | First PCR | 3'-end | Uzi-PriF1 | SEQ ID NO: 189 GGGATATGTGTCCTACCGTATCAGG |
| | Nest PCR | 5'-end | Spec-nstPriR1 | SEQ ID NO: 190 GTTGCCTTGGTAGGTCCAGC |
| | | 3'-end | Uzi-nstPriF1 | SEQ ID NO: 191 GAGCCATCAGTCCAACACTGC |

TABLE 7

Primers for ZFN cleavage activity.

| OGL 1 | Control/ZFN 111879 | SEQ ID NO: 192 TGGCACTAATCTCACCGGCT SEQ ID NO: 193 AGTCTTAGAAGTACGCTACCGT |
|---|---|---|
| OGL 2 | Control/ZFN 111885 | SEQ ID NO: 194 TACTTGGCTTCGGCGGCGA SEQ ID NO: 195 GGGTGACTTTTACGCGTCTCG |
| OGL 11 | Control/ZFN 117402 | SEQ ID NO: 196 GGTCACGACGCATGGCCTAA SEQ ID NO: 197 AGGATGCATGGATCACCGTC |
| OGL 12 | Control/ZFN 117404 | SEQ ID NO: 198 GCTCTGTTGTGCAGCCGTAC SEQ ID NO: 199 CGTTGCAGATACCACAGTGTAC |
| OGL 13 | Control/ZFN 117429 | SEQ ID NO: 200 GCTAGTAGCTGTTTACACGGCGTCT SEQ ID NO: 201 AGGTCGAGACAACCAAGTAGAG |
| OGL 14 | Control/ZFN 117406 | SEQ ID NO: 202 ACAGGACATCGAGCTTGCAT SEQ ID NO: 203 CAGAAGAAAGGCATCAACTCATG |
| OGL 15 | Control/ZFN 117408 | SEQ ID NO: 204 CTCTTTCACCTCTACTTTTACTTCAG SEQ ID NO: 205 ATTGAACCGTTGTCAAAGCCA |
| OGL 16 | Control/ZFN 117411 | SEQ ID NO: 206 CACAGCGTCAGGGCGGTAAC SEQ ID NO: 207 GGCACGCACCTGTCACTGAC |

TABLE 7-continued

Primers for ZFN cleavage activity.

| OGL 17 | Control/ZFN 117413 | SEQ ID NO: 208 GTACGCGCCCGGGAACTCCT SEQ ID NO: 209 CCTGCGGCCCACGTGCATCT |
|---|---|---|

Deployment of the In-Out PCR assay in a protoplast targeting system was particularly challenging as large amounts of the plasmid DNA was used for transfection, and the large amount of plasmid DNA remains in the protoplast targeting system and is subsequently extracted along with cellular genomic DNA. The residual plasmid DNA may dilute the relative concentration of the genomic DNA and reduce the overall sensitivity of detection and can also be a significant cause of non-specific, aberrant PCR reactions. The ZFN induced NHEJ-based donor insertion typically occurs in either a forward or a reverse orientation. In-Out PCR analysis of DNA for the forward orientation insertion often exhibited false positive bands, possibly due to shared regions of homology around the ZFN binding site in the target and donor that could result in priming and extension of unintegrated donor DNA during the amplification process. False positives were not seen in analyses that probed for reverse orientation insertion products and therefore all targeted donor integration analysis was carried out to interrogate reverse donor insertion in the Rapid Targeting Analysis. In order to further increase specificity and reduce background, a nested PCR strategy was also employed. The nested PCR strategy used a second PCR amplification reaction that amplified a shorter region within the first amplification product of the first PCR reaction. Use of asymmetric amounts of "In" and "Out" primers optimized the junctional PCR further for rapid targeting analysis at selected genomic loci.

The In-Out PCR analysis results were visualized on an agarose gel. For all *Zea mays* selected genomic loci, "ZFN+donor treatments" produced a near expected sized band at the 5' and 3' ends. Control ZFN or donor alone treatments were negative in the PCR suggesting that the method was specifically scoring for donor integration at the target site. All treatments were conducted in replicates of three to six and presence of the anticipated PCR product in multiple replicates (>2 at both ends) was used to confirm targeting. Donor insertion through NHEJ often produces lower intensity side products that are generated due to processing of linearized ends at the target and/or donor ZFN sites. In addition, it was observed that different ZFNs resulted in different levels of efficiency for targeted integration, with some of the ZFNs producing consistently high levels of donor integration, some ZFNs producing less consistent levels of donor integration, and other ZFNs resulting in no integration. Overall, for each of the *Zea mays* selected genomic loci targets that were tested, targeted integration was demonstrated within the *Zea mays* representative genomic loci targets by one or more ZFNs, which confirms that each of these loci were targetable. Furthermore, each of the *Zea mays* selected genomic loci targets is suitable for precision gene transformation. The validation of these *Zea mays* selected genomic loci targets was repeated multiple times with similar results every time, thus confirming the reproducibility of the validation process which includes plasmid design and construct, protoplast transformation, sample processing, and sample analysis.

Conclusions

The donor plasmid and one ZFN designed to specifically cleave a Zea mays selected genomic loci targets were transfected into Zea mays c.v. Hi-II protoplasts and cells were harvested 24 hours later. Analysis of the genomic DNA isolated from control, ZFN treated and ZFN with donor treated protoplasts by In-Out junctional PCR showed targeted insertion of the universal donor polynucleotide as a result of genomic DNA cleavage by the ZFNs (Table 8). These studies show that the universal donor polynucleotide system can be used to assess targeting at endogenous sites and for screening candidate ZFNs. Finally, the protoplast based Rapid Targeting Analysis and the novel universal donor polynucleotide sequence systems provide an improved system for screening genomic targets and ZFNs for precision genome engineering efforts in plants. The methods can be extended to assess site specific cleavage and donor insertion at genomic targets in any system of interest using any nuclease that introduces DNA double or single strand breaks.

and the mixture was inverted until the PEG 4000 was completely mixed with the protoplast/DNA solution. Next, the protoplast/DNA/PEG mixture was incubated at room temperature for 15-20 minutes. After incubation, the protoplast/DNA/PEG mixture was washed with 1 ml of W5 (2 mM MES pH6.0, 205 mM NaCl, 167 mM $CaCl_2$, 6.7 mM KCl) and centrifuged at 180-200×g for 15 minutes. After removal of the supernatant, 1 ml of WI media (4 mM MES pH6.0, 0.6 M mannitol, 20 mM KCl) was added to and used to resuspend the cell protoplast pellets. The resuspended pellets were covered with aluminum foil and incubated overnight. Protoplast transfection efficiencies were calculated using a Quanta Flowcytometer™ from Beckman-Coulter Inc (Brea, Calif.) and the transfection efficiency was calculated within the 10-50% range. All transfection treatments were done in replicates of six.

A similar transfection protocol as previously described for Zea mays c.v. Hi-II derived protoplasts was deployed for the isolation of Zea mays c.v. B104 protoplasts. The protoplasts were obtained from juvenile husk tissue by slicing husks manually into thin (about 0.5 mm) strips and then slicing

TABLE 8

Results of the integration of a universal donor polynucleotide sequence within the Zea mays selected genomic loci targets.

| Name | ID | Location | Cluster Assignment | ZFN (pDAB#) | Donor (pDAB#) | Targetable Locus (Y/N) |
|---|---|---|---|---|---|---|
| OGL01 | optimal_loci_204637_G1 | chr5:200298202..200301414 | 16 | 111879 | 111845 | Y |
| OGL02 | optimal_loci_204726_Gl | chr5:200665730..200670667 | 03 | 111885 | 111846 | Y |
| OGL08 | optimal_loci_31710 | chr1:194939396..194943360 | 23 | 117400 | 117415 | Y |
| OGL11 | optimal_loci_64542 | chr2:72203716..72205045 | 14 | 117402 | 117416 | Y |
| OGL12 | optimal_loci_156393 | chr4:154313884..154315253 | 10 | 117404 | 117417 | Y |
| OGL15 | preffered_loci_198387 | chr5:164712378..164713567 | 25 | 117408 | 117419 | Y |
| OGL13 | optimal_loci_157315 | chr4:158710709..158711983 | 30 | 117429 | 117434 | Y |
| OGL14 | optimal_loci_197372 | chr5:158680601..158681681 | 26 | 117406 | 117418 | Y |
| OGL16 | optimal_loci_232228 | chr6:144719567..144723469 | 28 | 117411 | 117420 | Y |
| OGL17 | optimal_loci_285621 | chr8:118321357..118322528 | 06 | 117413 | 117421 | Y |

Example 5: Maize Protoplast Generation and Transfection

Protoplasts were derived from Zea mays c.v. Hi-II suspension cells by incubation with cell wall digesting enzymes (cellulase, "Onozuka" R10—Yakult Pharmaceuticals, Japan; and pectolyase, 320952—MP Biomedicals, Santa Ana, Calif. and purified using a sucrose gradient. For transfection, protoplasts were diluted to a concentration of 1.67 million/ml using MMG (MES pH6.0, 0.6M mannitol, 15 mM $MgCl_2$) and 300 µL of protoplasts (~500,000) were aliquoted into sterile 2 ml tubes, plasmid DNA (comprising the YFP transgene expression cassette, the ZFN transgene expression cassette, the polynucleotide donor transgene expression cassette, of a combined ZFN/polynucleotide donor transgene expression cassette) was added at a total concentration of 40 µg to each 2 ml tube, mixed gently and incubated for 5-10 minutes at room temperature. Next, 300 µL of PEG 4000 was added to the protoplast/DNA solution crosswise. The sliced tissue was moved into a sterile Erlenmeyer flask containing 25 ml of Enzyme Solution and the flask was placed into a desiccation chamber for 15 minutes. Flasks were then capped, covered in aluminum foil, and shaken overnight on the lowest speed of an orbital shaker at room temperature.

Figure 18:
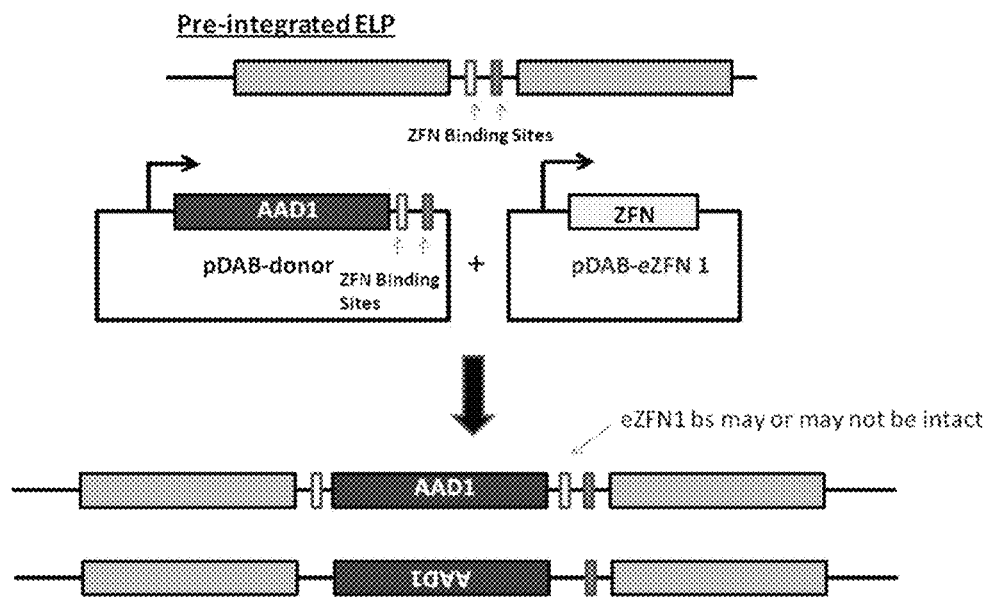
FIG. 18 illustrates donor insertion via NHEJ at an ELP in protoplast Rapid Targeting Analysis. Insertion can occur in a forward or a reverse orientation.

Example 6: Rapid Targeting Analysis of a Donor Polynucleotide Integrated within an Engineered Landing Pad Genomic Site Donor insertion at an engineered locus in maize: An analysis was used to demonstrate insertion of a 5 Kb donor within the Engineered Landing Pad 1 (ELP1) genomic target as described in U.S. Pat. App. No. 2011/0191899. The donor DNA was inserted within the genome of Zea mays c.v. Hi-II line protoplasts (this line, "106685[1]-007", was produced from the transformation and integration of pDAB106685) via an NHEJ integration method. The donor integrated within the ZFN1 and ZFN3 zinc finger binding sites (FIG. 18). The approach used for the NHEJ mediated integration within the ELP1 genomic target required that the ELP1 target and donor plasmids contain identical ZFN sites (ZFN1 or ZFN3). As the donor polynucleotide sequence and ZFN were transfected into the protoplast cells, the ZFN cleaved the ELP1 genomic target and the plasmid donor DNA thereby generating identical ends. The resulting identical ends are ligated via NHEJ mediated cell repair resulting in the targeted insertion of the plasmid donor DNA within the ELP1 genomic target. The targeting of the ELP1 genomic target was demonstrated with two different ZFN-to-donor molar ratios (1:1 and 1:10). The results of the donor integration were confirmed using the locus disruption assay and In-Out PCR, but asymmetric PCR primer concentrations were not included. The insertion of the donor polynucleotide sequence can occur in two orientations and the In-Out PCR was designed for detection of both orientations.

Figure 19:
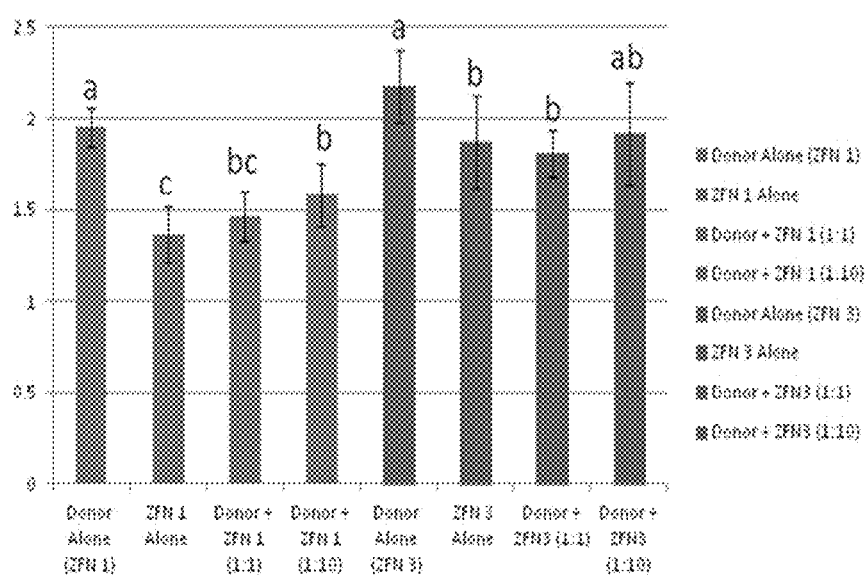
FIG. 19 illustrates disruption of the ZFN cleavage sites in ELP1. Disruption is represented as a decrease in qPCR signal in terms of target to reference ratio. On average 22% and 15% reduction in signal is observed for ZFN1 and ZFN3 respectively.

Disruption assay: The disruption assay is a hydrolysis probe assay (analogous to TaqmanTm) that measures whether a genomic DNA sequence ZFN binding site has been modified or rearranged. Accordingly, the intactness of the ZFN binding site is assayed. The ZFN mediated donor insertion or cleavage which is subsequently followed by NHEJ repair results in a loss of the ZFN binding sites and a reduction in detectable qPCR signal (see, U.S. Patent Publication No. 2014/0173783 herein incorporated by reference). The results of ELP1 cleavage at the ZFN1 and ZFN3 sites, and targeted integration of a donor sequence within the sites are provided in FIG. 19. The ZFN1 site was assayed with the delivery of a ZFN polynucleotide and in conjunction with a ZFN and donor polynucleotide at 1:1 and 1:10 ratios. The results indicated that the ZFN1 site of ELP1 was disrupted thereby suggesting potential targeting at this site. Likewise, the ZFN3 site of ELP1 was disrupted thereby suggesting potential targeting at this site. All treatments were performed in replicates of 6 for this experiment and data is presented as an average outcome.

In-Out PCR assay: To confirm targeted donor insertion at ZFN1 and ZFN3 of ELP1, an In-Out PCR was performed on genomic DNA isolated from the control protoplast samples (e.g., those treated with ZFN polynucleotides or donor polynucleotides alone) and protoplast samples treated with both ZFN and donor polynucleotides. The PCR primers were designed to amplify and detect donor insertion in either orientation. The results of the In-Out PCR indicated targeted donor insertion at both of the ZFN1 and ZFN3 sites of ELP1 for all samples tested (e.g. 1:1 and 1:10 ratios of donor to ZFN). The ZFN1 sites were targeted four out of six times, and the ZFN3 sites were targeted three out of six times. Donor insertions in both the forward and reverse orientations were detected by the In-Out PCR assay. Sequencing of the PCR material showed expected target-donor junction sequences as well as junctions where either donor/target or both were processed prior to ligation (FIG. 20).

Figure 21:
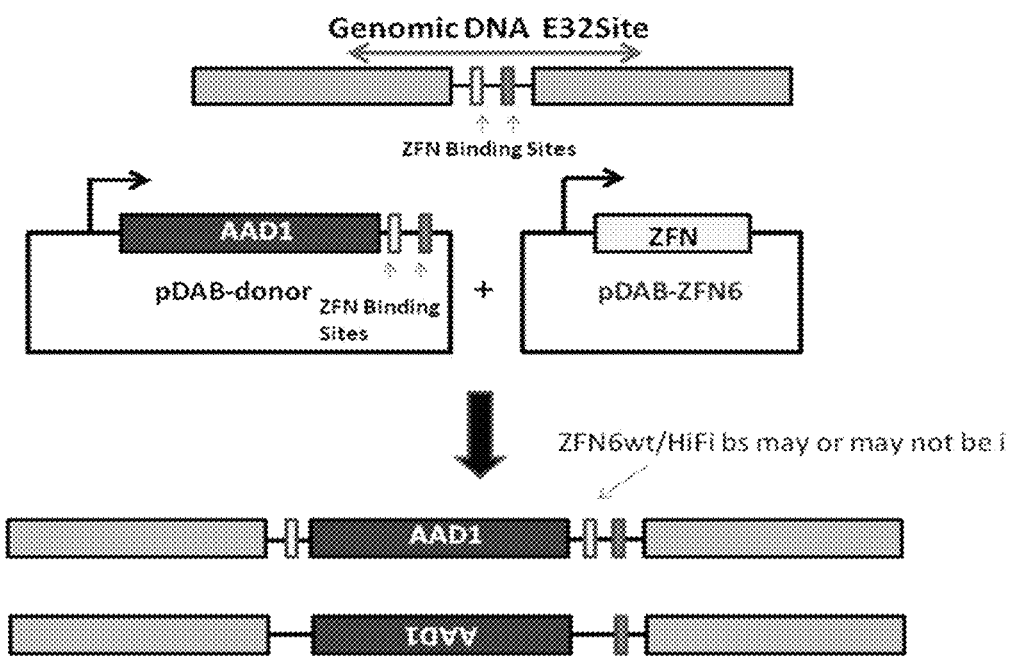
FIG. 21 illustrates donor insertion via NHEJ at E32 in protoplast Rapid Targeting Analysis. Insertion can occur in a forward or a reverse orientation.

Example 7: Rapid Targeting Analysis of a Donor Polynucleotide Integrated within an Endogenous Maize Loci The genomic locus of Corn Event DAS-59132 (herein referred to as E32) as described in U.S. Patent Publication No. 2014/0173783 herein incorporated by reference was targeted for polynucleotide donor insertion. A 5 Kb donor polynucleotide that contained the aad-1 transgene (pDAB100651) was targeted to an endogenous locus in maize (E32) using E32ZFN 6 (pDAB105906). The site specific integration of a donor polynucleotide sequence within the maize genome was confirmed using the Rapid Targeting Analysis via novel In-Out PCR assays at the 5' end 3' end of the donor inserted polynucleotide (FIG. 21).

Application of the Rapid Targeting Analysis as an In-Out PCR assay for the protoplast transfection system was particularly challenging since the protoplast transfection system is a transient transformation process. As such, a large excess of plasmid DNA delivered to the protoplast cells will stay in the system and may be extracted along with the cellular genomic DNA. Delivery of large quantities of plasmid DNA not only dilutes the effective concentration of the genomic DNA, thereby making detection of genomic targeting difficult, but also results in non-specific PCR reactions that produce false positives.

Figure 22:
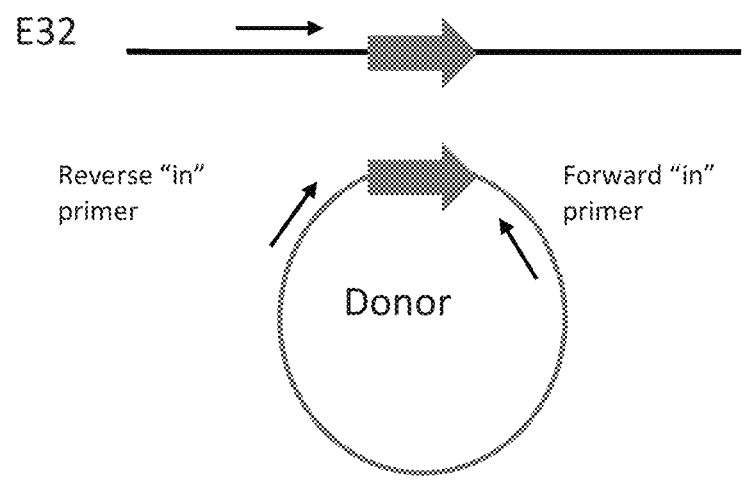
FIG. 22 illustrates a schematic showing the relation of the primers designed for the donor polynucleotide and the zinc finger binding sequence.

During the development of the Rapid Targeting Analysis In-Out PCR assay, one major source of false positives in the protoplast system was identified. As evidenced during these studies, NHEJ-based donor insertion can occur in two different directions, the donor can be inserted into the genome with a forward or reverse orientation. The In-Out PCR amplification and analysis of the forward orientation insertion often resulted in strong, intense amplicons that were false positives. Conversely, the In-Out PCR amplification and analysis of the reverse orientation insertion did not result in large numbers of false positive amplicons. It should be noted that the donor polynucleotide and the endogenous E32 locus share the same ZFN binding sites which can cause a PCR cross reaction (as shown in FIG. 22). The false positives are likely a by-product that results from a cross reaction caused by replication of the template that produces an extended amplified strand which incorporates the ZFN binding site. The resulting amplified strands may then bind to the ZFN binding site of the endogenous genomic sequences or to the polynucleotide donor sequence in the following PCR cycle to result in a false positive template that is amplified by the PCR reaction.

Asymmetric Nested In-Out (ANIO) PCR: To further reduce non-specific PCR amplification, a nested In-Out PCR strategy was designed so that a second In-Out PCR amplification could be utilized to amplify a region within the first In-Out PCR amplicon. The subsequent PCR amplification further increased specificity and detection of donor targeting and integration within the genomic locus. During the design and implementation of the nested PCR reaction, another novel improvement for reducing non-specific amplification was identified. Due to the presence of the large quantities of donor plasmid DNA, it was suspected that the "In" primers that bind to the donor DNA could have a major contribution to false positives. By reducing the concentrations of the "In" primer as compared to the concentration of the "Out" primers, false positives were significantly reduced. The resulting asymmetric nested In-Out (ANIO) PCR was used to demonstrate targeting of a donor polynucleotide at the *Zea mays* E32 locus in protoplast cells. All PCR primers were designed based on a positive control plasmid constructed to simulate targeted insertion at the E32 locus (Table 9).

TABLE 9

List of primers for the ANIO PCR are shown in the Table below.

| First PCR: | 5'-end | E32-5F1 | SEQ ID NO: 210 | ACA AAC ACG TCC TCC AAG GCT |
|---|---|---|---|---|
| | | NJ-AAD1-Pri2 | SEQ ID NO: 211 | GAC CAA GTC CTT GTC TGG GAC A |

TABLE 9-continued

List of primers for the AN1O PCR are shown in the Table below.

|  |  |  |  |  |
|---|---|---|---|---|
| | 3'-end | NJ-E32-2PriF1 | SEQ ID NO: 212 | GCT TTC CGT GTC ATT CGC TCG |
| | | NJ-665-PriR1 | SEQ ID NO: 213 | AAA TGT ACG GCC AGC AAC GTC |
| Nested PCR: | 5'-end | NJ-E32-5PriF2 | SEQ ID NO: 214 | TGG CTT TAG CCT TTT GCG AGT G |
| | | NJ-AAD1-nstPri1 | SEQ ID NO: 215 | CTT GAC TCG CAC CAC AGT TGG |
| | 3'-end | NJ-E32-2nstPriF1 | SEQ ID NO: 216 | CGT TTA TTC GCG TGT GTT GCC T |
| | | NJ-665-nstPriR1 | SEQ ID NO: 217 | CAG TTG CCA GGC GGT AAA GG |

Specifically, the first In-Out PCR was conducted in a 20 μL final reaction volume that contained 1×TaKaRa Ex Taq HS Buffer™, 0.2 mM dNTPs, 0.2 μM "Out" primer, 0.05 μM "In" primer, 0.75 unit of TaKaRa Ex Taq HS™ polymerase, and 10 ng extracted maize protoplast DNA. The PCR reaction was completed using a PCR program that consisted of 94° C. for 2 min, 20 cycles of 98° C. for 12 sec and 68° C. for 2 min, followed by 72° C. for 10 mM and held at 4° C.

The nested (or second) In-Out PCR was conducted in 20 μL final reaction volume that contained 1×TaKaRa Ex Taq HS Buffer™, 0.2 mM dNTPs, 0.2 μM "Out" primer, 0.1 μM "In" primer, 0.75 unit of TaKaRa Ex Taq HS Polymerase™, and 1 μL of the first PCR product. The reaction was completed using a PCR program that consisted of 94° C. for 2 min, 31 cycles of 98° C. for 12 sec, 66° C. for 30 sec and 68° C. for 45 sec, followed by 72° C. for 10 mM and held at 4° C. Final PCR products were run on an agarose gel along with 1 Kb Plus DNA Ladder™ (Life Technologies, Grand Island, N.Y.) for visualization.

The Rapid Targeting Analysis detected donor polynucleotide insertion within the E32 genome target locus in a reverse orientation. Of the samples that were treated with the ZFN and donor combination, six out of six reactions resulted in amplicons of expected sizes for both the 5' and 3' ends (as compared to the controls which did not result in site specific integration of a donor polynucleotide sequence). For the amplifications of the 3' ends, low amounts of smearing or laddering were observed on the agarose gel. This observation is likely due to processing of ends of DNA breaks produced prior to NHEJ repair. In addition, the amplification of a non-specific amplicon was seen in control samples consisting of "donor alone" for amplifications of the 3'-ends. This non-specific amplicon was a smaller molecular weight size as compared to the expected size amplicon of positive control. Nevertheless, the donor polynucleotide donor was successfully integrated within the E32 genomic target locus, and the Rapid Targeting Analysis was deployed to efficiently identify and detect site specific integrants.

Example 8: Targeting Analysis of a Donor Polynucleotide Integrated within an Endogenous Soybean Loci Designed ZFNs were transformed into soybean protoplasts using the above described transformation methodology. The cleavage efficiency for the FAD2 locus was assessed for the various ZFNs via a locus disruption assay as described in US Patent Publication No. 2014/0173783. In addition, zinc finger nuclease-mediated integration of a donor sequence within the FAD2 loci was assessed using an In-Out PCR assay and the resulting PCR amplicons were sequenced to characterize the donor integration within the soybean genome.

Figure 23:
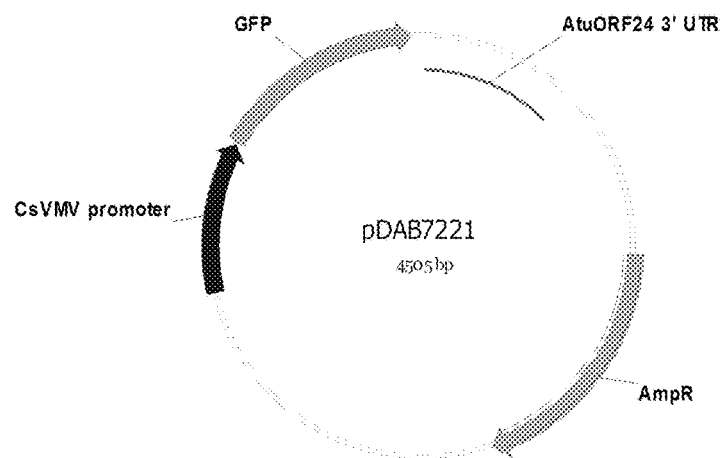
FIG. 23 illustrates a plasmid map of pDAB7221.

The experiments were comprised of treatment groups containing donor vector alone, ZFN vector alone or ZFN and donor vectors combined (Table 10). In addition, the experiments included negative control treatment groups of untransformed cells or cells transformed with a control vector, pDAB7221 (FIG. 23), comprising a Green Fluorescent Protein expression cassette driven by the CsVMV promoter and flanked by the AtuORF24 3'-UTR within a high copy number plasmid. The transformed samples were harvested approximately 18-24 hours after transfection. Preliminary data demonstrated high activity of F2, ZFN contained in plasmid, pDAB115601 and, consequently, this ZFN plasmid was used as a positive control in all subsequence experiments.

As detailed in Table 10, the transformation experiments contained a total of 80 μg of DNA, with plasmid pDAB7221 added as necessary to bring the total amount of DNA to 80 μg. The ratio of donor vector to ZFN-expressing plasmid was approximately 10:1. Each experiment or treatment consisted of six experimental replicates which were processed and analyzed independently. Experiments evaluating the ZFNs were done in two sets of experiments.

TABLE 10

Experimental design. The ZFN plasmids were evaluated in two sets (F2 ZFNs 1-3 and F2 ZFNs 4-7). Donor vectors appropriate for the ZFN plasmids were used for the targeting experiments. Six replicates were done for each treatment.

| Sample IDs | Donor Plasmid | Amount of Donor Plasmid (μg) | ZFN Plasmid | Amount of ZFN Plasmid (μg) | Amount of pDAB7221 (GFP) |
|---|---|---|---|---|---|
| untreated | — | — | — | — | — |
| GFP control | — | — | — | — | 80 |
| donor 1 alone | pDAB115620 | 36 | — | — | 44 |
| donor 2 alone | pDAB115622 | 36 | — | — | 44 |
| F2 ZFN1_WT alone | — | — | pDAB115600 | 4 | 76 |
| F2 ZFN2_WT alone | — | — | pDAB115601 | 4 | 76 |
| F2 ZFN3_WT alone | — | — | pDAB115602 | 4 | 76 |
| F2 ZFN1_HF alone | — | — | pDAB115603 | 4 | 76 |
| F2 ZFN2_HF alone | — | — | pDAB115605 | 4 | 76 |
| F2 ZFN3_HF alone | — | — | pDAB115607 | — | — |
| donor1 + F2 ZFN1_WT | pDAB115620 | 36 | pDAB115600 | 4 | 40 |

TABLE 10-continued

Experimental design. The ZFN plasmids were evaluated in two sets (F2 ZFNs 1-3 and F2 ZFNs 4-7). Donor vectors appropriate for the ZFN plasmids were used for the targeting experiments. Six replicates were done for each treatment.

| Sample IDs | Donor Plasmid | Amount of Donor Plasmid (μg) | ZFN Plasmid | Amount of ZFN Plasmid (μg) | Amount of pDAB7221 (GFP) |
|---|---|---|---|---|---|
| donor1 + F2 ZFN2_WT | pDAB115620 | 36 | pDAB115601 | 4 | 40 |
| donor2 + F2 ZFN3_WT | pDAB115622 | 36 | pDAB115602 | 4 | 40 |
| donor1 + F2 ZFN1_HF | pDAB115620 | 36 | pDAB115603 | 4 | 40 |
| donor1 + F2 ZFN2_HF | pDAB115620 | 36 | pDAB115605 | 4 | 40 |
| donor2 + F2 ZFN3_HF | pDAB115622 | 36 | pDAB115607 | 4 | 40 |
| untreated | — | — | — | — | — |
| GFP control | — | — | — | — | 80 |
| donor 1 alone | pDAB115620 | 36 | — | — | 44 |
| donor 2 alone | pDAB115622 | 36 | — | — | 44 |
| F2 ZFN2_WT alone | — | — | pDAB115601 | 4 | 76 |
| F2 ZFN4_HF alone | — | — | pDAB115609 | 4 | 76 |
| F2 ZFN5_HF alone | — | — | pDAB115608 | 4 | 76 |
| F2 ZFN6_HF alone | — | — | pDAB115606 | 4 | 76 |
| F2 ZFN7_HF alone | — | — | pDAB115604 | 4 | 76 |
| donor1 + F2 ZFN2_WT | pDAB115620 | 36 | pDAB115601 | 4 | 40 |
| donor2 + F2 ZFN4_HF | pDAB115622 | 36 | pDAB115609 | 4 | 40 |
| donor2 + F2 ZFN5_HF | pDAB115622 | 36 | pDAB115608 | 4 | 40 |
| donor1 + F2 ZFN6_HF | pDAB115620 | 36 | pDAB115606 | 4 | 40 |
| donor1 + F2 ZFN7_HF | pDAB115620 | 36 | pDAB115604 | 4 | 40 |

Figure 24:
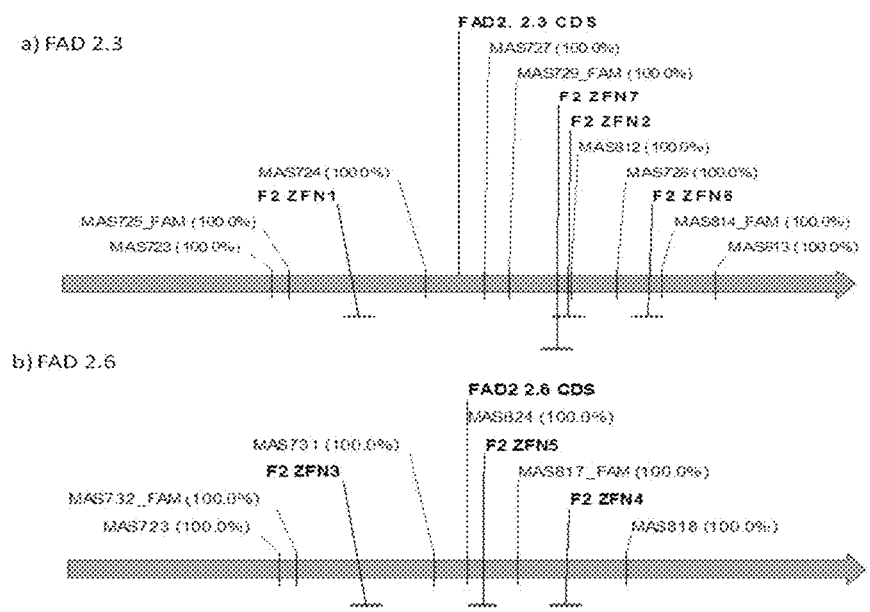
FIG. 24 illustrates a schematic of probe/primers for the locus disruption assay. The F2 ZFN binding sites for the FAD2 2.3 and 2.6 genes and primers used for the disruption assay are indicated.

Analysis of Targeting: DNA samples from the targeting experiments were analyzed using a locus disruption assay to detect modifications at the FAD2 ZFN cleavage sites and assess targeting by NHEJ. The qPCR assay was designed to measure intact ZFN binding sites in the FAD2 targets. The ZFN mediated donor insertion or cleavage followed by NHEJ repair results in loss of the ZFN binding site and subsequent reduction in detectable qPCR signal. ZFNs that possesses significant cleavage activity resulted in the production of amplicons with a reduced signal compared to the donor alone treatment. The primers and probes used in the locus disruption assay are shown in Table 11, and their relative positions on the FAD2 loci are shown in FIG. 24.

Treatment of protoplasts with the FAD2 2.3 ZFN2_WT ZFN (both experiments) and FAD2 2.6 ZFNs ZFN4_HF (one experiment) and F2 ZFN5_HF (both experiments) in the presence of the appropriate donor vectors resulted in a statistically significant lower signal compared to that obtained from an intact sequence (donor alone).

TABLE 11

Primers and probes for disruption PCR

| Primer Name | Sequence | Probe (fluorophore/quencher) | Target ZFN |
|---|---|---|---|
| GMS116 SOY F | SEQ ID NO: 218 GTAATATGGGCTCAGAGGAATGGT | — | — |
| GMS116 SOY R | SEQ ID NO: 219 ATGGAGAAGAACATTGGAATTGC | — | — |
| GMS116 SOY | SEQ ID NO: 220 CCATGGCCCGGTACCATCTGGTC | HEX | — |
| MAS723 | SEQ ID NO: 221 CACGAGTGTGGTCACCATGCCTT | — | ZFN1 |
| MAS724 | SEQ ID NO: 222 TGAGTGTGACGAGAAGAGAAACAGCC | — | ZFN1 |
| MAS725_FAM | SEQ ID NO: 223 AGCAAGTACCAATGGGTTGATGATGTTGTG | FAM | ZFN1 |
| MAS727 | SEQ ID NO: 224 TGCAAGCCACTACCACCCTTATGC | — | ZFN2/ZFN7 |
| MAS728 | SEQ ID NO: 225 GGCAAAGTGTGTGTGCTGCAAATATG | — | ZFN2/ZFN7 |
| MAS729_FAM | SEQ ID NO: 226 CTAACCGTGAGAGGCTTCTGATCTATGTCTCTGA | FAM | ZFN2/ZFN7 |
| MAS731 | SEQ ID NO: 227 TGAGTGTGATGAGAAGAGAAGCAGCC | — | ZFN3 |

TABLE 11-continued

Primers and probes for disruption PCR

| Primer Name | Sequence | Probe (fluorophore/ quencher) | Target ZFN |
|---|---|---|---|
| MAS732_FAM | SEQ ID NO: 228 AGCAAGTACCCATGGGTTGATGATGTTATG | FAM | ZFN3 |
| MAS723 | SEQ ID NO: 229 CACGAGTGTGGTCACCATGCCTT | — | ZFN3 |
| MAS812 | SEQ ID NO: 230 TTGGTTTGGCTGCTATGTGTTTATGG | — | ZFN6 |
| MAS813 | SEQ ID NO: 231 TGTGGCATTGTAGAGAAGAGATGGTGAG | — | ZFN6 |
| MAS814_FAM | SEQ ID NO: 232 AGGGAGCTTTGGCAACTATGGACAGAGATTAT | FAM | ZFN6 |
| MAS824 | SEQ ID NO: 233 AGCCTTCAATGTCTCTGGCAGACCCT | — | ZFN4/ZFN5 |
| MAS818 | SEQ ID NO: 234 GGCATAGTGTGTGTGCTGCAGATATG | — | ZFN4/ZFN5 |
| MAS817_FAM | SEQ ID NO: 235 CAAATCGTGAGAGGCTTTTGATCTATGTCTCTGA | FAM | ZFN4/ZFN5 |

Locus Specific In-Out PCR: To confirm targeted donor insertion, DNA from all treatments was subjected to a locus-specific In-Out PCR assay. The donor vector in the experiments was designed to contain binding sites for all ZFNs that were being tested for targeted integration within the FAD2 locus. Co-delivery of the ZFN and donor into soybean cells results in cleavage of the ZFN binding sites at the target and in the donor vector and subsequent integration of the donor into the cleaved FAD2 locus via non-homologous end-joining mechanism. The ends of the FAD2 chromosome site and the linearized donor vector that are generated by ZFN cleavage undergo processing prior to integration within the FAD2 locus, and may result in imperfect end joining products. Confirmation of targeted integration at the target was performed based on an "In-Out" PCR strategy, where the "Out" primer recognizes sequence at the native genomic locus and the "In" primer binds to sequence within the donor DNA. The In-Out PCR assay was performed on both the 5'- and 3'-ends of the insertion junction.

All of the tested ZFNs showed some evidence of targeting and integration of a donor fragment into the FAD2 soybean locus in at least one experiment as determined by a PCR product in the donor and ZFN samples. Results of donor integrated targeting using the following ZFNs; F2 ZFN2_WT, F2 ZFN2_HF and F2 ZFN4_HF were reproducible as PCR products were produced in at least 2 out of 6 experimental replicates at both the 5' and 3' ends (Table 12).

TABLE 12

Summary of NHEJ targeting at the FAD2 locus in soybean protoplasts. The number of replicates positive for In-Out PCR in independent targeting experiments is shown for the experiments or treatments.

| ZFN ID | F2 ZFN1-3A | F2 ZFN1-3B | F2 ZFN4-7A | F2 ZFN4-7B |
|---|---|---|---|---|
| ZFN 1 WT | 1/6 | 0/6 | — | — |
| ZFN 1 HF | 1/6 | 4/6 | — | — |
| ZFN 2 WT | 3/6 | 5/6 | 5/6 | 5/6 |
| ZFN 2 HF | 4/6 | 3/6 | — | — |
| ZFN 3 WT | 0/6 | 0/6 | — | — |
| ZFN 3 HF | 0/6 | 0/6 | — | — |
| ZFN 4 HF | — | — | 2/6 | 2/6 |
| ZFN 5 HF | — | — | 0/6 | 0/6 |
| ZFN 6 HF | — | — | 0/6 | 0/6 |
| ZFN 7 HF | — | — | 4/6 | 0/6 |

Sequencing of the In-Out PCR Products: Two of the amplicons (of expected size) from each of the In-Out PCR targeting experiments completed with pDAB1115620 and F2 ZFN2_WT or pDAB1115620 and F2 ZFN2_HF were cloned into a plasmid. The resulting plasmid was sequenced using the Sanger sequencing method. Sequences were aligned to a reference sequence in which the single-stranded 4 bp ends that are predicted to result from Fold cleavage were duplicated to represent all possible combinations of the ends. Ten unique sequence patterns were found from the 23 cloned sequences obtained (FIG. 25). All sequence patterns retained a portion of the FAD2 genomic reference sequence located between the ZFN binding sites (GAAATTTC), but the sequence patterns also possessed deletions relative to the FAD2 genomic reference sequence. Sequences 4WT1 and 4WT4 contained deletions that extended into the ZFN binding site on the 3' end of the GAAATTTC sequence. Two sequences, 1HF4 and 6HF4, had single-base insertions. The DNA sequence patterns observed demonstrate that targeting of the donor DNA into the soybean FAD2 locus occurred.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. A method for detecting site specific integration of a polynucleotide donor sequence within a genomic target site, the method comprising:

amplifying a genomic DNA with a first round of PCR to produce a first amplicon using a first Out-PCR primer designed to bind to the genomic DNA target site and a first In-PCR primer designed to bind the integrated polynucleotide donor sequence, wherein the first In-PCR primer is provided at a lower concentration than the first Out-PCR primer and said first Out-PCR primer and said first In-PCR primer pair are selected to amplify reverse orientation inserted polynucleotide donor sequences, wherein the reverse orientation is relative to the orientation of the original transformation vector;

amplifying the first amplicon with a second round of PCR using primers specific to sequences located within the first amplicon to produce a second amplicon; and, detecting the presence of the second amplicon, wherein the production of the second amplicon indicates the presence of the site specific integration event.

2. The method of claim 1, wherein the genomic target site comprises an endogenous or an engineered genomic target site.

3. The method of claim 1, wherein the first round of PCR is conducted using a relative concentration of first Out-PCR primer to first In-PCR primer of about 4:1, 3:1 or 2:1.

4. The method of claim 1, wherein the first In-PCR primer comprises a concentration of 0.05-0.09 µM, and the first Out-PCR primer comprises a concentration of at least 0.1 µM.

5. The method of any one of claim 1, 2, 3, or 4, wherein the second round of PCR comprises a second Out-PCR primer designed to bind to the genomic DNA target site of the first amplicon and a second In-PCR primer designed to bind the integrated polynucleotide donor sequence of the first amplicon.

6. The method of claim 5, wherein the second In-PCR primer is provided at a lower concentration than the second Out-PCR primer.

7. The method of claim 5, wherein the second round of PCR is conducted using a relative concentration of second Out-PCR primer to second In-PCR primer of about 4:1, 3:1 or 2:1.

8. The method of claim 5, wherein the second In-PCR primer comprises a concentration of 0.05-0.1 µM, and the second Out-PCR primer comprises a concentration of 0.2 µM.

9. The method of claim 1, wherein the genomic DNA comprising the site specific integration of the polynucleotide donor sequence within the genomic target site is a plant genomic DNA.

10. The method of claim 9, wherein the plant genomic DNA is isolated from a monocotyledonous plant.

11. The method of claim 9, wherein the plant genomic DNA is isolated from a dicotyledonous plant.

12. The method of claim 9, wherein the site specific integration of the polynucleotide donor sequence within the genomic target site is produced by cleavage of the genomic DNA target site with a site specific nuclease.

13. The method of claim 12, wherein the site specific nuclease is selected from the group consisting of a Zinc Finger nuclease, a CRISPR nuclease, a TALEN nuclease, and a meganuclease.

14. The method of claim 12, wherein the site specific integration of the polynucleotide donor sequence within the genomic target site occurs via a Non Homologous End Joining mechanism.

15. The method of claim 1, wherein the detecting step comprises electrophoresis of the second amplicon in a gel.

16. The method of claim 1, wherein the detecting step comprises sequencing the second amplicon.

17. A method for detecting site specific integration of a polynucleotide donor sequence within a genomic target site of transfected plant cells, said method comprising
   amplifying a genomic DNA with a first round of PCR to produce a first amplicon, wherein said PCR is conducted using a first Out-PCR primer designed to bind to the genomic target site and a first In-PCR primer designed to bind the polynucleotide donor sequence, further wherein said first In-PCR primer is provided at a lower concentration than the first Out-PCR primer and said first Out-PCR primer and said first In-PCR primer pair are selected to amplify reverse orientation inserted polynucleotide donor sequences, wherein the reverse orientation is relative to the orientation of the original transformation vector;
   amplifying the first amplicon with a second round of PCR using a second Out-PCR primer designed to bind to the genomic DNA target site of said first amplicon and a second In-PCR primer designed to bind the integrated polynucleotide donor sequence of said first amplicon; and,
   detecting the presence of a second amplicon, wherein the production of a second amplicon indicates the presence of a site specific integration event.

* * * * *